(12) United States Patent
Cai et al.

(10) Patent No.: US 8,722,703 B2
(45) Date of Patent: May 13, 2014

(54) FUSED AMINO PYRIDINES FOR THE TREATMENT OF BRAIN TUMORS

(75) Inventors: Xiong Cai, Bedford, MA (US); Changgeng Qian, Wayland, MA (US)

(73) Assignee: Curis, Inc., Lexington, MA (US)

( * ) Notice: Subject to any disclaimer, the term of this patent is extended or adjusted under 35 U.S.C. 154(b) by 454 days.

(21) Appl. No.: 12/688,312

(22) Filed: Jan. 15, 2010

(65) Prior Publication Data
US 2010/0184801 A1    Jul. 22, 2010

Related U.S. Application Data

(60) Provisional application No. 61/145,297, filed on Jan. 16, 2009, provisional application No. 61/150,402, filed on Feb. 6, 2009.

(51) Int. Cl.
*A61K 31/437* (2006.01)
*C07D 471/04* (2006.01)

(52) U.S. Cl.
CPC .................................. *A61K 31/437* (2013.01)
USPC .......................................... 514/303; 546/118

(58) Field of Classification Search
CPC .................................................... A61K 31/437
See application file for complete search history.

(56) References Cited

U.S. PATENT DOCUMENTS

| | | | |
|---|---|---|---|
| 6,723,727 | B1 | 4/2004 | Peyman et al. |
| 7,138,401 | B2 | 11/2006 | Kasibhatla et al. |
| 7,138,402 | B2 | 11/2006 | Kasibhatla et al. |
| 7,160,885 | B2 | 1/2007 | Currie et al. |
| 7,169,801 | B2 | 1/2007 | Bressi et al. |
| 7,241,890 | B2 | 7/2007 | Kasibhatla et al. |
| 2004/0102458 | A1 | 5/2004 | Chiosis et al. |
| 2005/0049263 | A1 | 3/2005 | Kasibhatla et al. |
| 2006/0148805 | A1 | 7/2006 | Chen et al. |
| 2007/0105874 | A1 | 5/2007 | Zhang et al. |
| 2007/0253896 | A1 | 11/2007 | LeBrazidec et al. |
| 2007/0275984 | A1 | 11/2007 | Imogai et al. |
| 2008/0221132 | A1 | 9/2008 | Cai et al. |
| 2008/0234297 | A1 | 9/2008 | Qian et al. |

FOREIGN PATENT DOCUMENTS

| | | |
|---|---|---|
| WO | 2005028434 A2 | 3/2005 |
| WO | 2005028438 A1 | 3/2005 |
| WO | 2006029115 A2 | 3/2006 |
| WO | 2006084030 A2 | 8/2006 |
| WO | 2007075572 A2 | 7/2007 |
| WO | 2008055068 A2 | 5/2008 |
| WO | 2008115719 A1 | 9/2008 |

OTHER PUBLICATIONS

Kasibhatla, et. al., "Rationally Designed High-Affinity 2-Amino-6-halopurine Heat Shock Protein 90 Inhibitors That Exhibit Potent Antitumor Activity," J. Med. Chem., 50: 2767-2778 (2007).
Budillon, et. al, "Multiple-Target Drugs: Inhibitors of Heat Shock Protein 90 and of Histone Deacetylase," Current Drug Targets, 6: 337-351 (2005).
Dymock, B. et. al., "Adenine derived inhibitors of the molecular chaperone HSP9O—SAR explained through multiple X-ray structures," Bioorganic & Medicinal Chemistry Letters, 14: 325-328 (2004).
Chiosis, G., et. al., "A small molecule designed to bind to the adenine nucleotide pocket of Hsp90 causes Her2 degradation and the growth arrest and differentiation of breast cancer cells," Chemistry & Biology, 8: 289-299 (2001).
Llaugher, L, et. al., "Evaluation of 8-Arylsulfanyl, 8-Arylsulfoxyl, and 8-Arylsulfonyl Adenine Derivatives as Inhibitors of the Heat Shock Protein 90," J. Med. Chem., 48: 2892-2905 (2005).
Stebbins, C.E., et. al., "Crystal Structure of an Hsp9O—Geldanamycin Complex: Targeting of a Protein Chaperone by an Antitumor Agent," Cell, 89: 239-250 (1997).
Biamonte, Marco A., et al., "Orally Active Purine-Based Inhibitors of the Heat Shock Protein 90," J. Med. Chem., 49: 817-828 (2006).
Kotera, C., et. al., "Synthesis of 3-deaza-3-nitro-2'-deoxyadenosine," Bioorganic & Medicinal Chemistry, 14: 1935-1941 (2006).
Yun, Bo-Geon, et. al., "Novobiocin Induces a Distinct Conformation of Hsp90 and Alters Hsp90-Cochaperone-Client Interactions," Biochemistry, 43: 8217-8229 (2004).
Chiosis, G., et. al., "Development of a Purine-Scaffold Novel Class of Hsp90 Binders that Inhibit the Proliferation of Cancer Cells and Induce the Degradation of Her2 Tyrosine Kinase," Bioorganic & Medicinal Chemistry,10: 3555-3564 (2002).
He, H., et. al., "Identification of Potent Water Soluble Purine-Scaffold Inhibitors of the Heat Shock Protein 90," J. Med. Chem., 49, 381-390 (2006).
Sawai, Ayana, et al., "Inhibition of Hsp90-Down-regulates Mutant Epidermal Growth Factor Receptor (EGFR) Expression and Sensitizes EGFR Mutant Tumors to Paclitaxel," Cancer Res. 68:(2), 589-591 (2008).
Sos, Martin L., "Expression of Signaling Mediators Downsstream of EGF-Receptor Predict Sensitivity to Small Molecule Inhibitors Directed Against the EGF-Receptor Pathway," Journal of Thoracic Oncology, 3(2), 170-173 (2008).
Bao, Rudi et al., "Targeting heat shock protein 90 with CUDC-305 overcomes erlotinib resistance in non-small cell lung cancer," Molecular Cancer Therapeutics, 8(12)3296-3306 (2009).
Bao, R et al., "CUDC-305, a Novel Synthetic HSP90 INhibitor with Unique Pharmacologic Properties for Cancer Therapy", Clinical Cancer Research, The American Association for Cancer Research, 15(12):4056-4057, Jun. 15, 2009.

*Primary Examiner* — James D Anderson
(74) *Attorney, Agent, or Firm* — Elmore Patent Law Group, P.C.; Roy P. Issac; Carolyn S. Elmore, Esq.

(57) ABSTRACT

The present invention relates to the use of compounds with fused amino pyridine core for the treatment of malignancies associated with brain and lung. The oral administration of compounds of the instant application results in effective brain penetration and provides for non-intrusive treatment of brain and lung tumors.

5 Claims, 34 Drawing Sheets

Figure 1A:
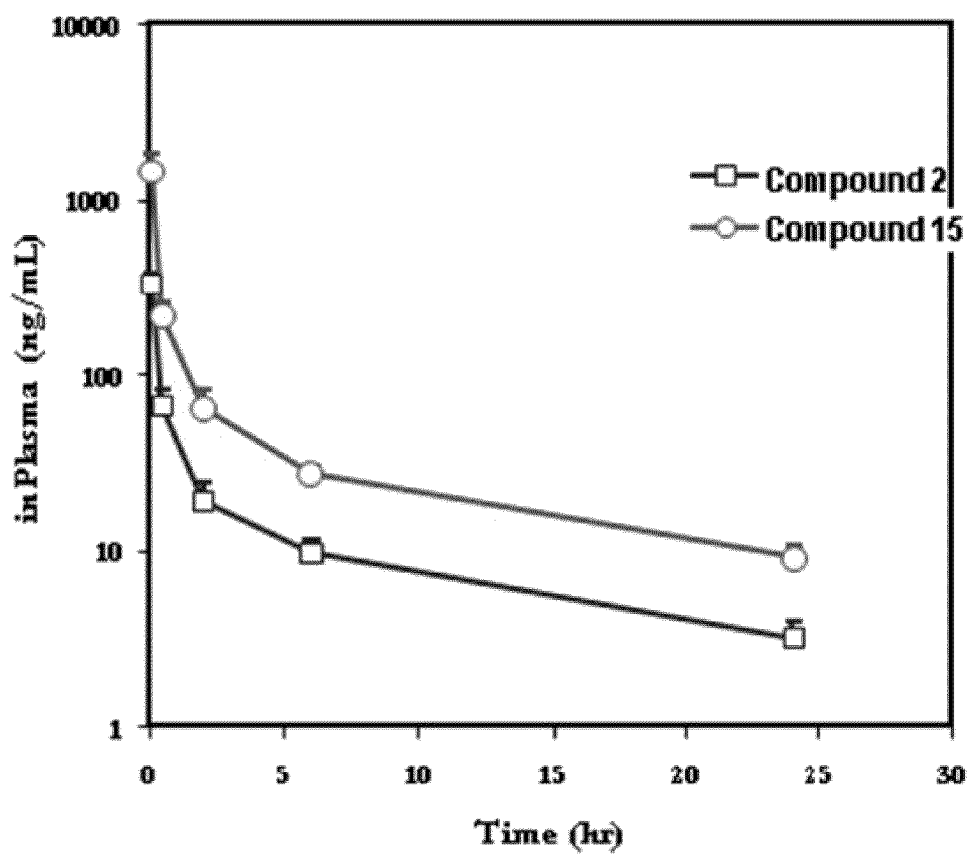

|  |  | Compound 2 | Compound 15 |
|---|---|---|---|
| AUC iv | hr*ng/ml | 320 | 1069 |
| AUC po | hr*ng/ml | 316 | 1339 |
| F | % | 49.5% | 62.6% |

|  |  | Compound 2 | Compound 15 |
|---|---|---|---|
| AUC $_{0-24h}$iv | hr*ng/g | 25337 | 40034 |
| AUC $_{0-24h}$po | hr*ng/g | 18783 | 21998 |
| F | % | 37.1% | 27.5% |

FIG. 2C

|  |  | Compound 2 | Compound 15 |
|---|---|---|---|
| AUC $_{0-24h}$iv | hr*ng/ml | 11705 | 6380 |
| AUC $_{0-24h}$po | hr*ng/ml | 11575 | 3214 |
| F | % | 49.4% | 25.2% |

| | Compound 15, 30 mg/kg, oral | | | |
|---|---|---|---|---|
| PK Parameters | Plasma | Tumor | Brain | Lung |
| K10　　　　1/hr | 0.109 | 0.0339 | 0.210 | 0.262 |
| $T_{1/2}$　　　hr | 6.4 | 20.5 | 3.3 | 4.6 |
| $T_{max}$　　　hr | 0.8 | 2.0 | 2.0 | 2.0 |
| $C_{max}$　　　ng/mL | 460 | 1630 | 1378 | 40615.7 |
| $AUC_{0-24}$　hr*ng/mL | 3135 | 26730 | 10414 | 276356.0 |
| $AUC_{inf}$　hr*ng/mL | 3192 | 51154 | 10480 | 279212.8 |

| PK Parameters | | iv @10 mg/kg |
|---|---|---|
| K10 | 1/hr | 1.589172 |
| Half-Life | hr | 4.405216 |
| MRT | hr | 2.921971 |
| Cmax | ng/mL | 1523.112888 |
| AUC | hr*ng/mL | 958.431591 |
| Vss | L/kg | 30.487 |
| CL | L/hr/kg | 10.433 |

| PK Parameters | | po @30 mg/kg | po @160 mg/kg |
|---|---|---|---|
| K10 | 1/hr | 0.254 | 0.280 |
| Half-Life | hr | 7.75661 | 7.2 |
| Tmax | hr | 1.0 | 0.2 |
| Cmax | ng/mL | 560.3 | 4844.1 |
| AUC | hr*ng/mL | 2761.1 | 18867.6 |
| CL_F | L/hr/kg | 5.8 | 8.5 |
| Bioavailability % | | 96.0 | 123.0 |

| PK Parameters | | iv @10 mg/kg |
|---|---|---|
| K10 | 1/hr | 0.051 |
| Half-Life | hr | 18.3 |
| Cmax | ng/g | 3967.6 |
| Tmax | hr | 0.3 |
| AUC | hr*ng/g | 79149.5 |
| Tumor/Plasma Ratio (fold) | | 82.6 |

| PK Parameters | | po @30 mg/kg | po @160 mg/kg |
|---|---|---|---|
| K10 | 1/hr | 0.065 | 0.039 |
| Half-Life | hr | 20.4 | 17.6 |
| Tmax | hr | 3.2 | 4.2 |
| Cmax | ng/g | 2084.9 | 16573.0 |
| AUC | hr*ng/g | 50849.4 | 498110.4 |
| Tumor/Plasma Ratio (fold) | | 18.4 | 26.4 |

FUSED AMINO PYRIDINES FOR THE TREATMENT OF BRAIN TUMORS

RELATED APPLICATIONS

This application claims the benefit of U.S. Provisional Application Nos. 61/145,297, filed Jan. 16, 2009, and 61/150,402, filed Feb. 6, 2009. The entire teachings of the above applications are incorporated herein by reference.

BACKGROUND OF THE INVENTION

Despite scientific advances in understanding the causes and treatment of human malignancy, a persistent challenge facing basic and clinical investigators is how to adequately treat primary and metastatic brain tumors. The blood-brain barrier is a physiologic obstruction to the delivery of systemic chemotherapy to the brain parenchyma and central nervous system (CNS). (Deeken et. al., *Clin Cancer Res* 2007; 13(6) 2007, 1663-1674). Brain tumors are protected from systemic chemotherapy by the blood-brain barrier (BBB) and by intrinsic properties of the tumors. Pharmacologic studies of delivery of conventional chemotherapeutics and novel therapeutics showing actual tumor concentrations and biologic effect are lacking (Muldoon et. al. *J Clin Oncol.* 2007, 25(16): 2295-305. Glioblastoma is the most frequent and most malignant human brain tumor. The prognosis remains very poor, with most patients dying within 1 year after diagnosis. (Ohgaki et. al. *American Journal of Pathology,* 170(5), 2007, 1445-1453). Thus, there remains a need to develop treatments for brain related disorders that can cross the blood brain barrier.

Patients with secondary brain tumors also have poor treatment prognosis due to the difficulty in delivering drugs across the blood brain barrier. Metastatic brain tumors are the most common intracranial neoplasm in adults, and although the exact incidence is unknown, it has been estimated to be as high as 200,000 cases per year in the U.S. alone. The frequency of metastatic brain tumors appears to be rising as a result of superior imaging modalities and earlier detection as well as longer survival after a primary cancer diagnosis because of more effective treatment of systemic disease. (Eichler et. al. *The Oncologist,* 12 (7), 884-898, 2007).

Patients with lung cancer account for approximately 50% of brain metastasis cases. The majority of active cytotoxic agents (like taxanes) in lung cancer treatment, are unable to effectively penetrate blood brain barrier (BBB). (Zarogoulidis et. al., *Journal of Clinical Oncology,* 2006 ASCO Annual Meeting Proceedings Part I, 24(18S) 2006. Considering the challenge in BBB penetration and the brain metastasis of lung cancer anti-cancer agents that can highly distribute to lung and cross blood brain barriers are highly sought after in cancer treatment of brain cancer and lung cancer with brain metastasis.

HSP90s are ubiquitous chaperone proteins that are involved in proper protein folding and stabilization of a wide range of proteins, including key proteins involved in signal transduction, cell cycle control and transcriptional regulation. Researchers have reported that HSP90 chaperone proteins are associated with important signaling proteins, such as steroid hormone receptors and protein kinases, including, e.g., Raf-1, EGFR, v-Src family kinases, Cdk4, and ErbB-2, many of which are overexpressed or mutated in various cancers (Buchner J. *TIBS,* 1999, 24, 136 141; Stepanova, L. et al. *Genes Dev.* 1996, 10, 1491 502; Dai, K. et al. *J. Biol. Chem.* 1996, 271, 22030-4). Studies further indicate that certain co-chaperones, e.g., HSP70, p60/Hop/Stil, Hip, Bag1, HSP40/Hdj2/Hsj1, immunophilins, p23, and p50, may assist HSP90 in its function (Caplan, A. *Trends in Cell Biol.* 1999, 9, 262 68). HSP90 is overexpressed in many cancers and has become a target for cancer therapy. HSP90 inhibitors possess potent anti-proliferative activity, usually at low nanomolar ranges, owing to their pharmacological characteristics of binding tightly to heat shock protein 90, coupled with a slow dissociation rate. (Newcomb et. al. *Anticancer Drugs* 2007 18(8):875-82). HSP90 has been shown to be present in a variety of primary and metastatic intracranial tumors including glioblastomas and medulloblastomas (Kato et. al., *Acta Neuropathol.* 1995; 89(2):184-8).

Recent studies also suggest that heat shock proteins (HSPs) play an important role in neurodegenerative disorders such as Parkinson's disease (PD), Alzheimer's disease (AD), amyotropic lateral sclerosis (ALS), Huntington disease (HD) (Luo, G-R. *Int. J. Biol. Sci.,* 2007, 3(1), 20-26; Dickey, C., *J. Clin. Invest.,* 2007, 117(3), p. 648-658). It has been shown that manipulation of HSPs, such as down regulation of HSP90 or up regulation of HSP70, affords beneficial effects in several neurodegenerative disorders either by reducing protein aggregation or facilitating proper folding of proteins to restore their function. Neurodegenerative diseases such as Alzheimer's disease (AD) and Huntington's disease (polyglutamine disease) are typical diseases likely caused by the abnormal accumulation of misfolded and aggregated proteins, and these diseases are thought to be inhibited by the action of Hsp70 as a chaperone. Apoptosis is one of the ways neurons die after ischemia. It has been shown that overexpression of Hsp70 in hippocampal CA1 neurons reduces evidence of protein aggregation under conditions where neuronal survival is increased (Giffard, R. G., et al., *J. Exp. Biol.* 207:3213-3220 (2004)).

A growing body of evidence supports the hypothesis that HSP90 inhibition affords neuroprotection in various animal models of neurological disease. HSP90 has been shown by mutational analysis to be necessary for the survival of normal eukaryotic cells. However, HSP90 is overexpressed in many tumor types indicating that it may play a significant role in the survival of cancer cells and that cancer cells may be more sensitive to inhibition of HSP90 than normal cells. For example, cancer cells typically have a large number of mutated and over expressed oncoproteins that are dependent on HSP90 for folding. In addition, because the environment of a tumor is typically hostile due to hypoxia, nutrient deprivation, acidosis, etc., tumor cells may be especially dependent on HSP90 for survival. Moreover, inhibition of HSP90 causes simultaneous inhibition of a number of client oncoproteins, as well as hormone receptors and transcription factors making it an attractive target for an anti-cancer agent. In fact, benzoquinone ansamycins, a family of natural products that inhibit HSP90, has shown evidence of therapeutic activity in clinical trials. Several promising ansamycin related HSP90 inhibitors are currently in clinical trial namely, 17-allylamino 17-demethoxygeldanamycin (17-AAG), 17-dimethylaminoethylamino-17-demethoxygeldanamycin (17-DMAG) and IPI-504. Another class of the HSP90 inhibitor is the synthetic small molecule purine-scaffold. Currently, many of the purine-scaffold HSP90 inhibitors are showing positive preclinical results; with the front runner being CNF-2024, which is currently in phase 1 clinical trial.

In recent years, molecularly targeted therapies, such as epidermal growth factor receptor (EGFR) inhibitors, have gained tremendous attention for their potential to improve patient survival and reduce toxic side effects, in particular for the treatment of lung cancer. Yet, early clinical trials of these inhibitors, such as gefitinib and erlotinib, were modestly encouraging, with a response in only ~10% of patients who carry genetic mutations of EGFR (Bao et. al., *Mol. Cancer. Ther.* 2009; 8(12) 2009). In addition, resistance almost invariably develops in these non-small cell lung cancer (NSCLC) patients although they respond to these receptor tyrosine kinase (RTK) inhibitors initially. Of these instances of so-called "acquired" resistance, it is estimated that ~50% are due to the emergence of an additional EGFR mutation in exon 20 (EGFRT790M), the "gatekeeper" residue within the kinase domain (Kobayashi et. al., *N. Engl. J. Med.* 2005; 352: 786-92; *Proc. Natl. Acad. Sci.* 2005, 102 11011-6). Structural analysis suggests that the T790M mutation sterically hinders the binding of erlotinib to the EGFR kinase domain by introducing a bulky methionine residue, thereby conferring erlotinib resistance (8, 9). There is also evidence to suggest that T790M mutation causes drug resistance by increasing the affinity of EGFR for ATP (Yun et. al., *Proc. Natl. Acad. Sci.* 2008, 105, 2070-5). To overcome such EGFRT790M-mediated resistance, several irreversible EGFR inhibitors able to form covalent bonds with Cys-797 at the edge of the ATP binding site are actively being tested in clinical trials. However, only modest efficacy has been reported, believed to be in part due to persistent PI3K/AKT/mTOR signaling following treatment (Bao et. al.).

Drugs targeting the protein HSP90 are quite new in cancer and neurodegenerative disease therapies. Their presence in many of the tumors associated with CNS point to a need for HSP-related drugs capable of crossing the blood brain barrier. As such, a promising therapy for brain related disorders would be HSP90 inhibitors that are efficient in crossing the blood brain barrier. This invention relates to fused amino pyridine compounds useful as HSP90 inhibitors for the treatment of brain related disorders. This invention further relates to treatment of cancers that are resistant to other epidermal growth factor receptor inhibitors. This invention further relates to the inhibition of HSP70 and the treatment of diseases related to HSP70.

SUMMARY OF THE INVENTION

The present invention relates to the unexpected discovery that certain HSP90 inhibitors containing fused amino pyridine core have good to excellent brain tissue deposition. The discovery supports the use of such compounds in the treatment of HSP90 related diseases and disorders such as cancer associated with brain and lung.

Accordingly, the present invention provides a method of treating brain and lung related disorders using a compound having the general formula I:

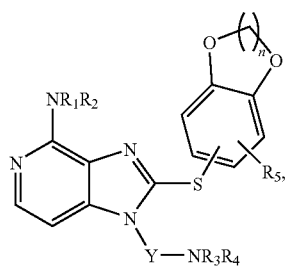

(I)

or its pharmaceutically acceptable salts thereof, wherein;
n is 1 or 2;
$R_1$ and $R_2$ are independently H, $C_1$-$C_8$ alkyl, $C_1$-$C_8$ substituted alkyl;

$R_3$ and $R_4$ are independently H, $C_1$-$C_8$ alkyl, $C_1$-$C_8$ substituted alkyl; $R_5$ is halogen, —$SR_6$ or —$NR_6R_7$ wherein $R_6$ and $R_7$ are independently H, $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, $C_2$-$C_8$ substituted alkynyl or $C_3$-$C_8$ cycloalkyl; and, Y is $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, $C_2$-$C_8$ substituted alkynyl, $C_3$-$C_8$ cycloalkyl or $C_3$-$C_8$ substituted cycloalkyl.

The invention also relates to the use of such compounds in the manufacture of a medicament for the treatment of brain related disorders, such as glioblastoma multiforme, neurodegenerative diseases such as Alzheimer's disease, and lung related disorders such as small cell and non-small cell lung carcinomas.

DETAILED DESCRIPTION OF THE INVENTION

FIG. 1A: Plasma concentrations of compounds 2 and 15 in tumor-bearing mice after IV administration (5 mg/kg), obtained through a cassette dosing study.

Figures 1B, 1C:
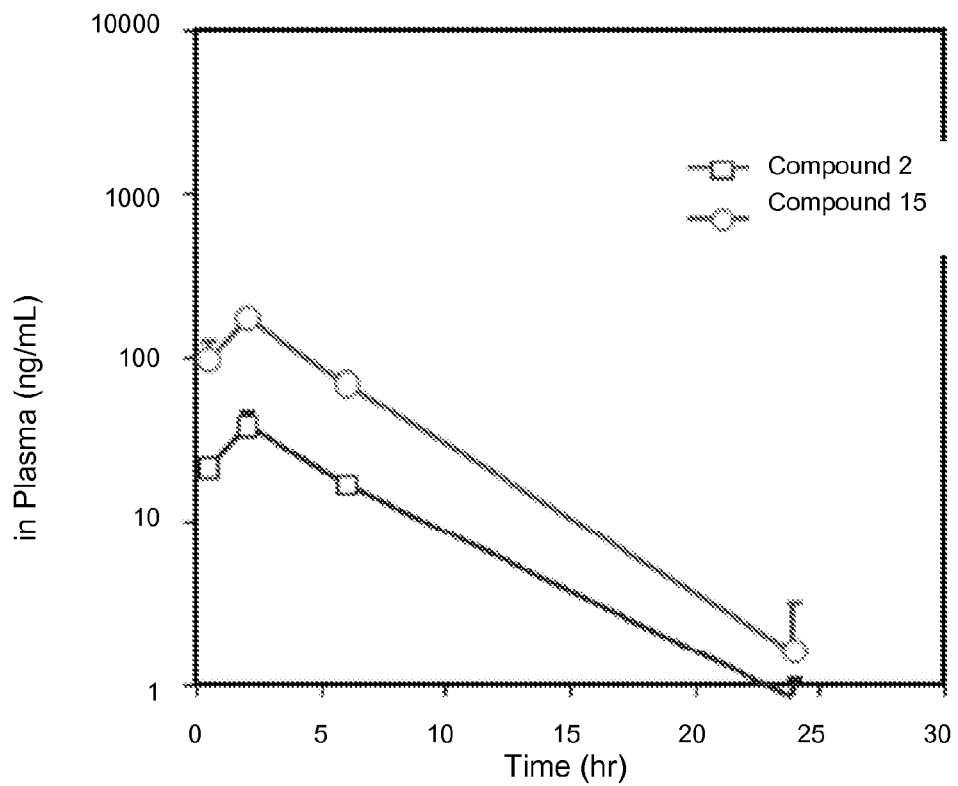

FIG. 1B: Plasma concentrations of compounds 2 and 15 in tumor-bearing mice after oral (10 mg/kg) administration, obtained through a cassette dosing study.

FIG. 1C: Plasma pharmacokinetic values for compounds 2 and 15 after IV (5 mg/kg) and Oral (10 mg/kg) administration.

Figure 2A:
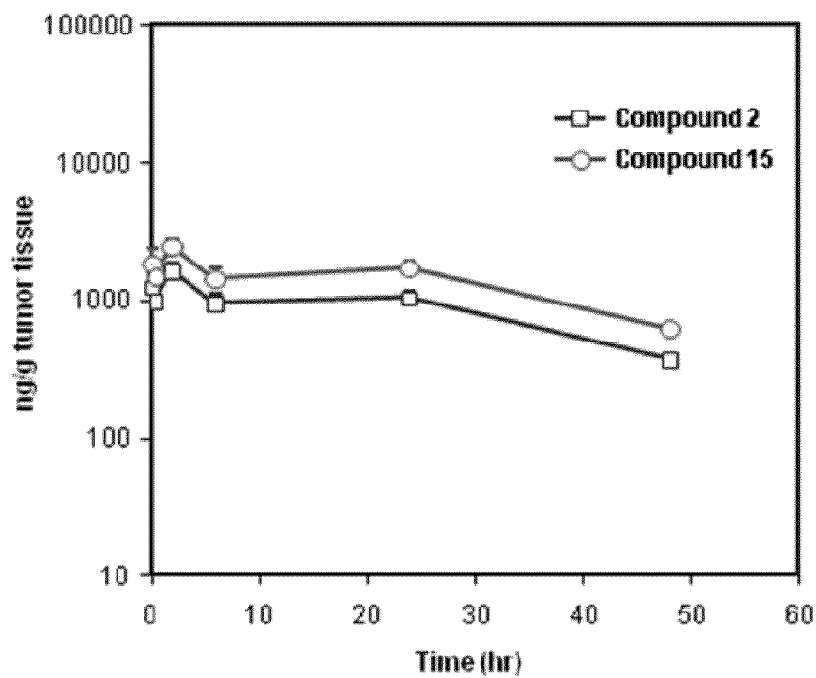

FIG. 2A: Tumor concentrations of compounds 2 and 15 in tumor-bearing mice after IV (5 mg/kg) administration, obtained through a cassette dosing study.

Figure 2B:
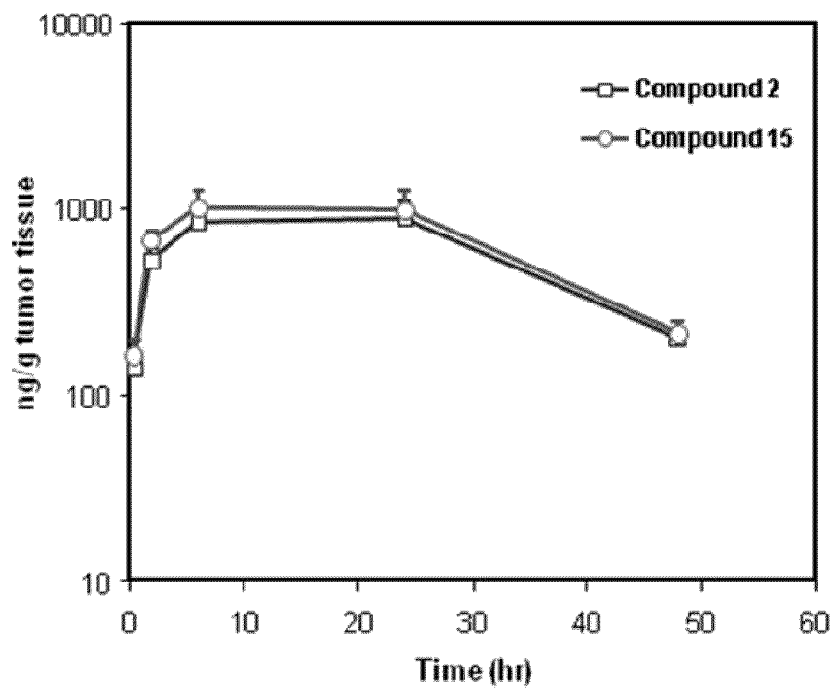

FIG. 2B: Tumor concentrations of compounds 2 and 15 in tumor-bearing mice after oral (10 mg/kg) administration, obtained through a cassette dosing study.

FIG. 2C: Plasma pharmacokinetic values for compounds 2 and 15 after IV (5 mg/kg) and Oral (10 mg/kg) administration.

Figure 3A:
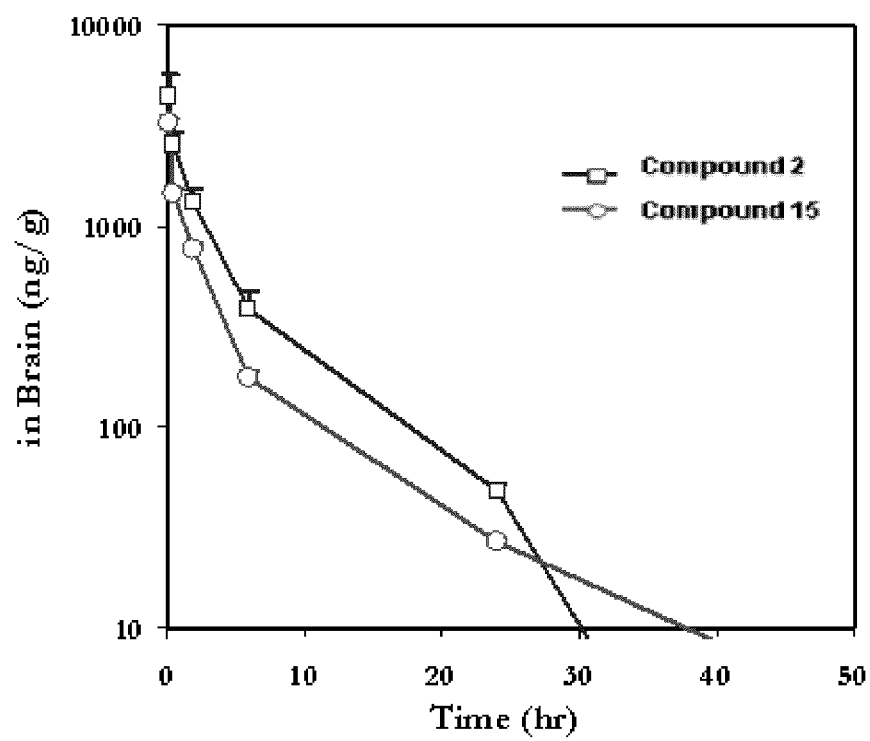

FIG. 3A: Brain concentrations of compounds 2 and 15 in tumor-bearing mice after IV (5 mg/kg).

Figures 3B, 3C:
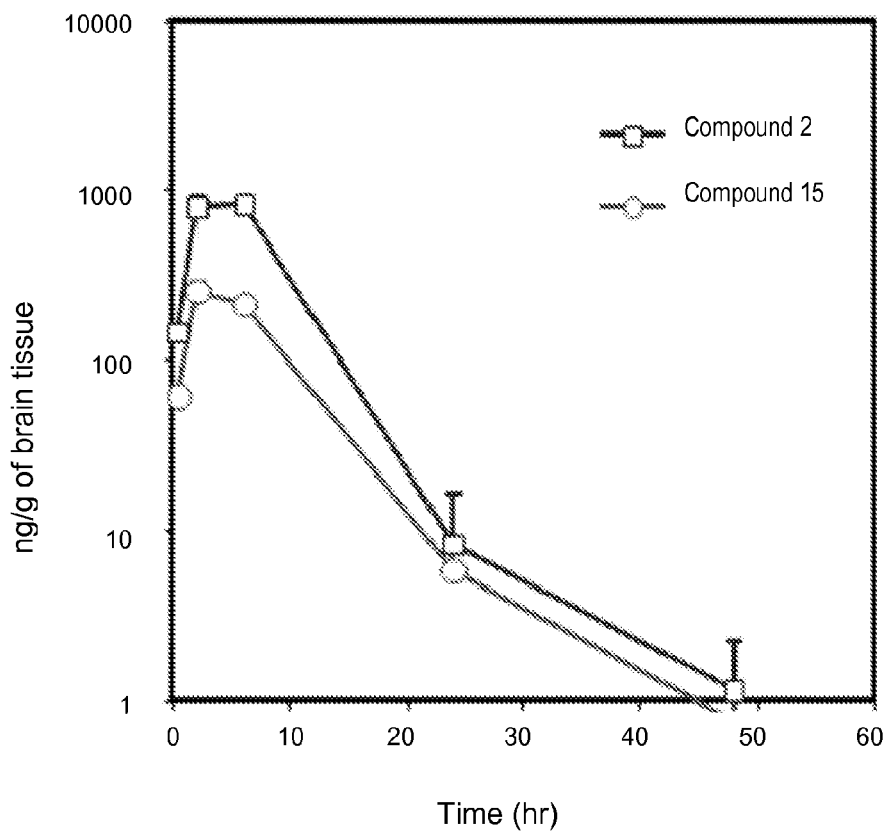
Figure 4A:
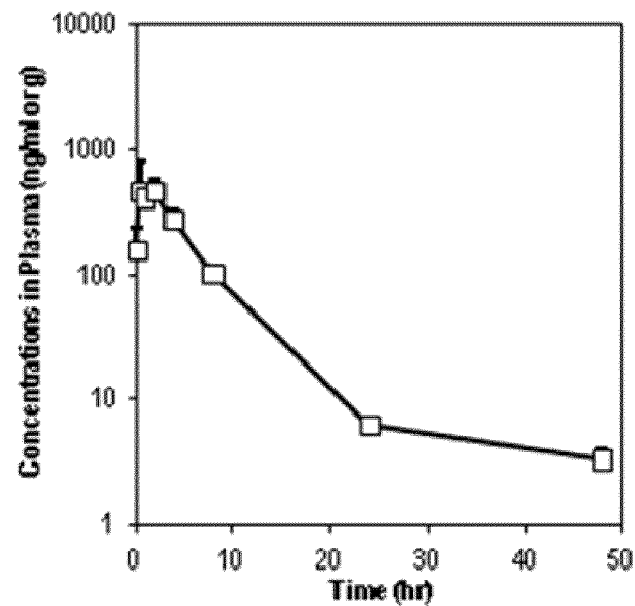
Figure 4B:
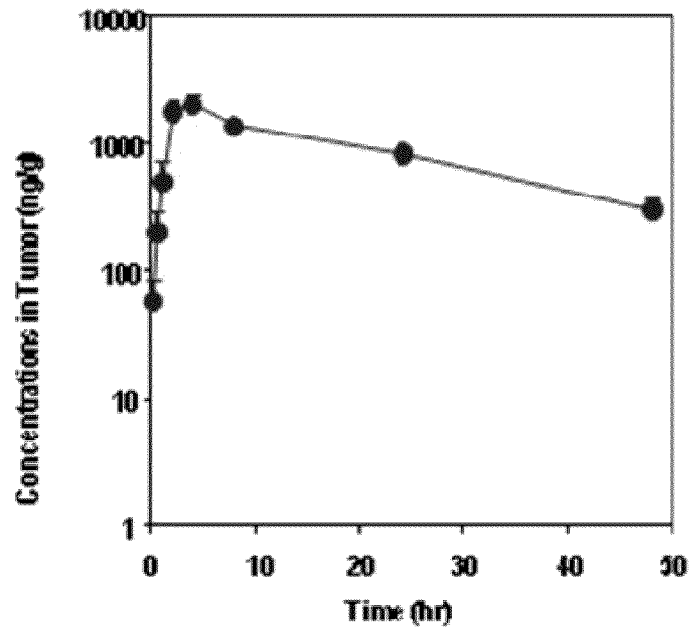
Figure 4C:
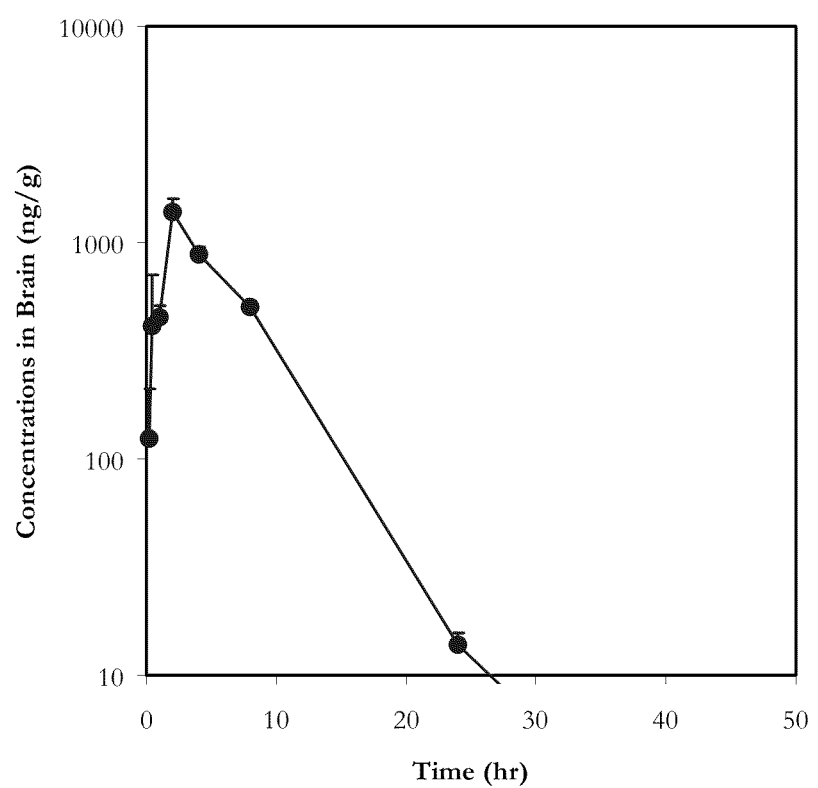
Figures 4D, 4E:
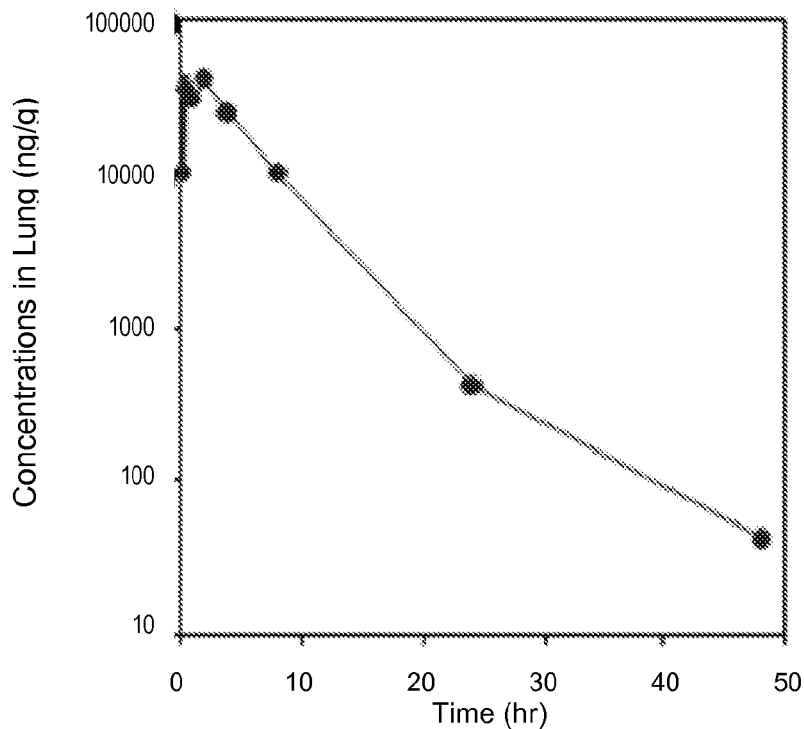

FIG. 3B: Brain concentrations of compounds 2 and 15 in tumor-bearing mice after oral administration (10 mg/kg).

FIG. 3C: Brain AUC values for compounds 2 and 15 after IV (5 mg/kg) and Oral (10 mg/kg) administration.

FIG. 4: Tissue concentrations of compound 15 in (a) plasma, (b) tumor, (c) brain, and (d) lung after oral administration (30 mg/kg), obtained through a single dose study; (e) Pharmacokinetic profile of compound 15 in plasma, tumor, brain and lung tissue after oral administration (30 mg/kg).

Figures 5A, 5B:
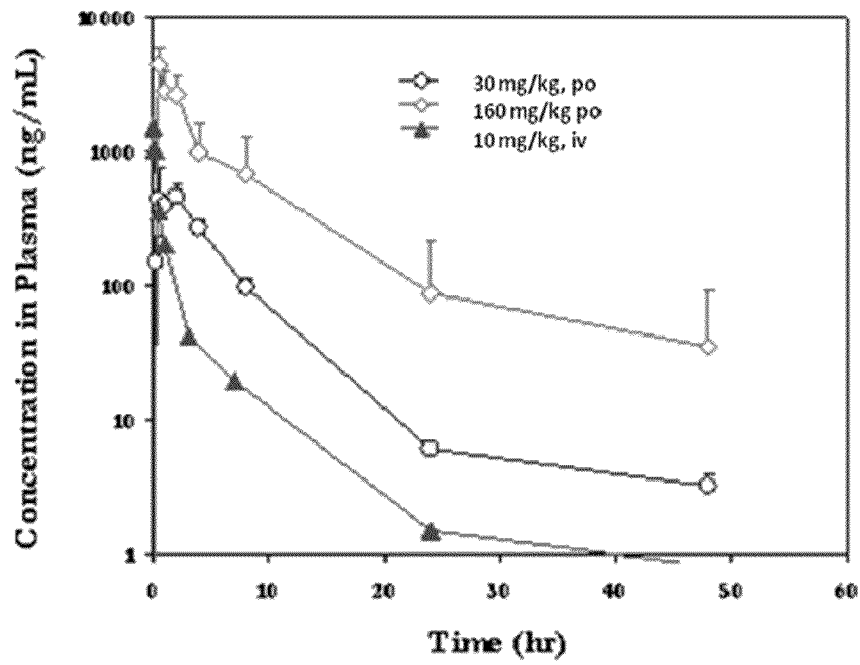

FIG. 5: (a) Plasma concentration and (b) pharmacokinetic profile of compound 15 after administration to tumor bearing mice in 10 mg/kg IV, 30 mg/kg p.o. and 160 mg/kg p.o. dosages showing bioavailability and half-life in plasma.

Figures 6A, 6B:
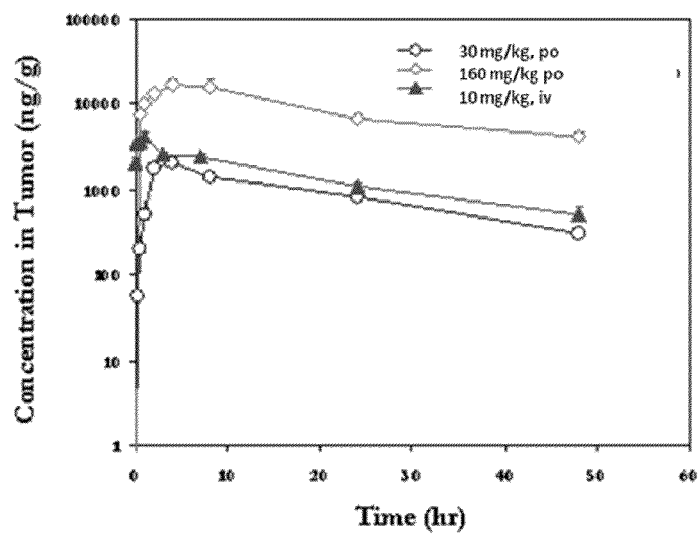

FIG. 6: (a) Tumor concentration and (b) pharmacokinetic profile of compound 15 after administration to tumor bearing mice in 10 mg/kg IV, 30 mg/kg p.o. and 160 mg/kg p.o. dosages showing bioavailability and half-life in tumor.

Figure 7:
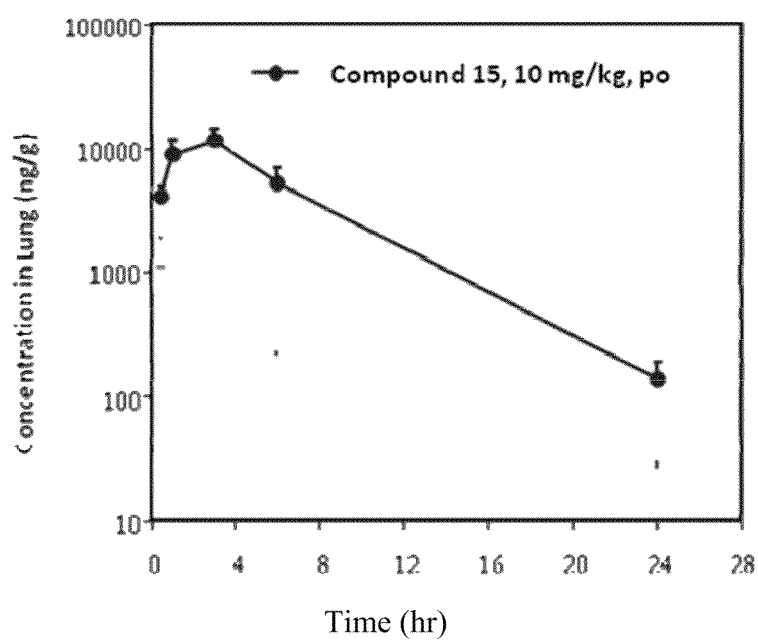

FIG. 7: Lung concentration of compound 15 after oral administration (10 mg/kg).

Figure 8A:
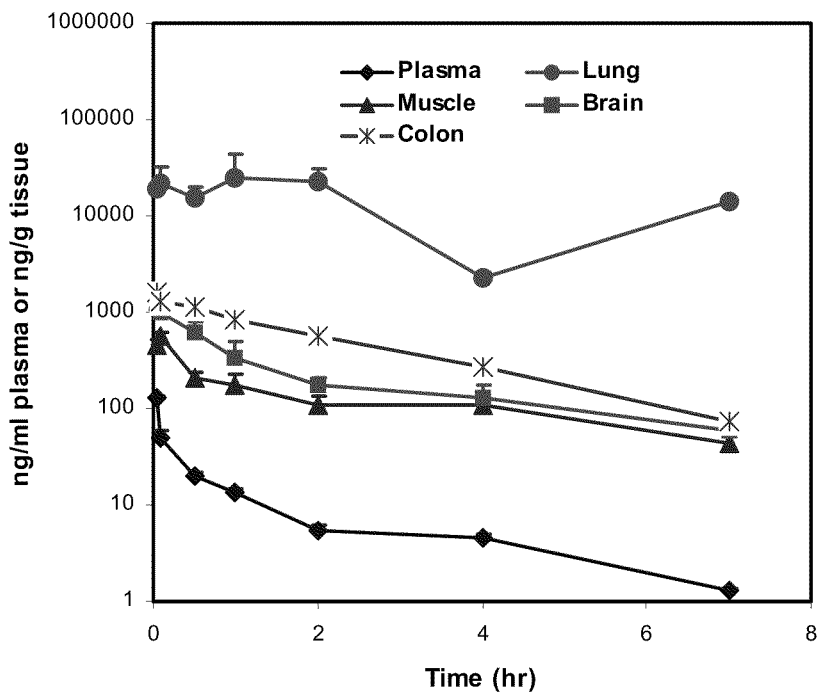

FIG. 8A: Plasma and tissue concentrations of Compound 2 after IV (5 gm/Kg) administration.

Figure 8B:
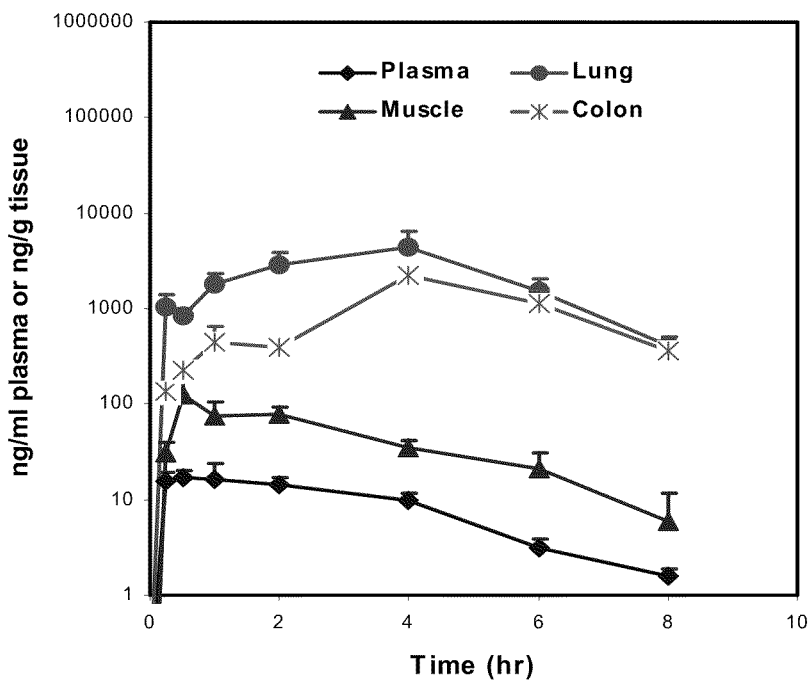

FIG. 8B: Plasma and tissue concentrations of Compound 2 after oral (10 gm/Kg) administration.

Figure 9:
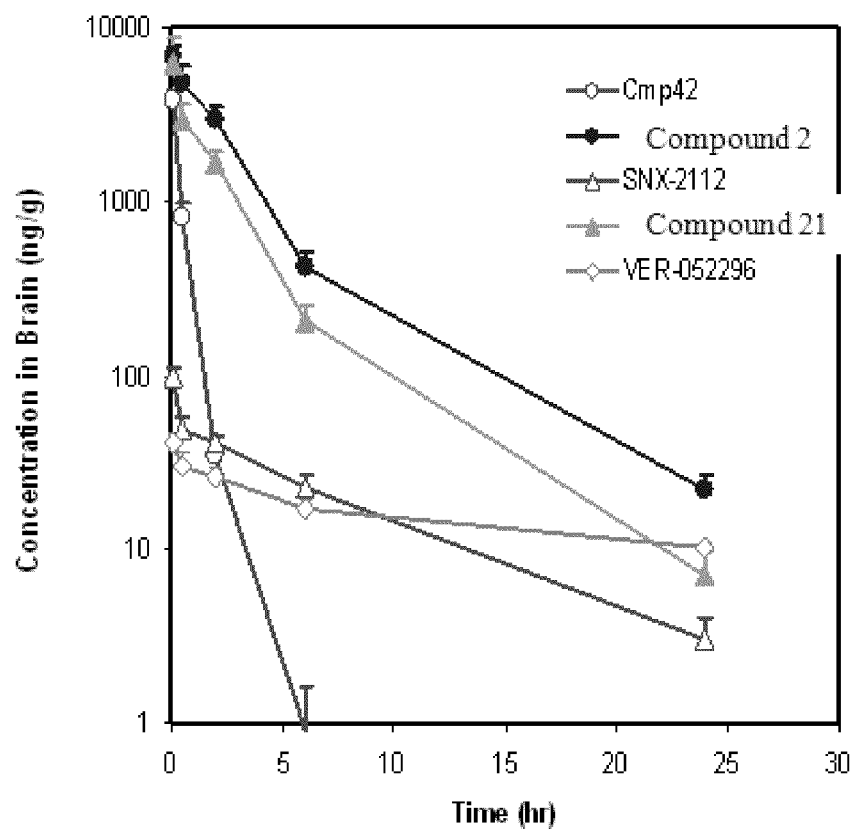

FIG. 9: Comparison of brain penetration of compounds 2 and 21 with reference compounds (VER-052296, Cmp42, SNX-2112) after IV (5 mg/Kg) administration.

Figure 10:
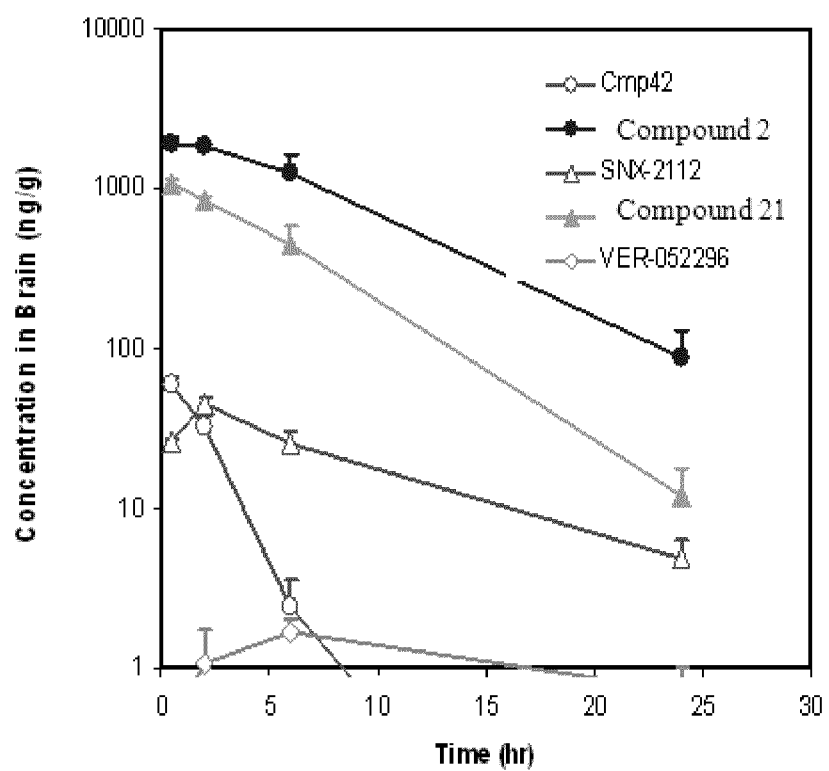

FIG. 10: Comparison of brain penetration of compounds 2 and 21 with reference compounds (VER-052296, Cmp42, SNX-2112) after oral (10 mg/Kg) administration.

Figure 11:
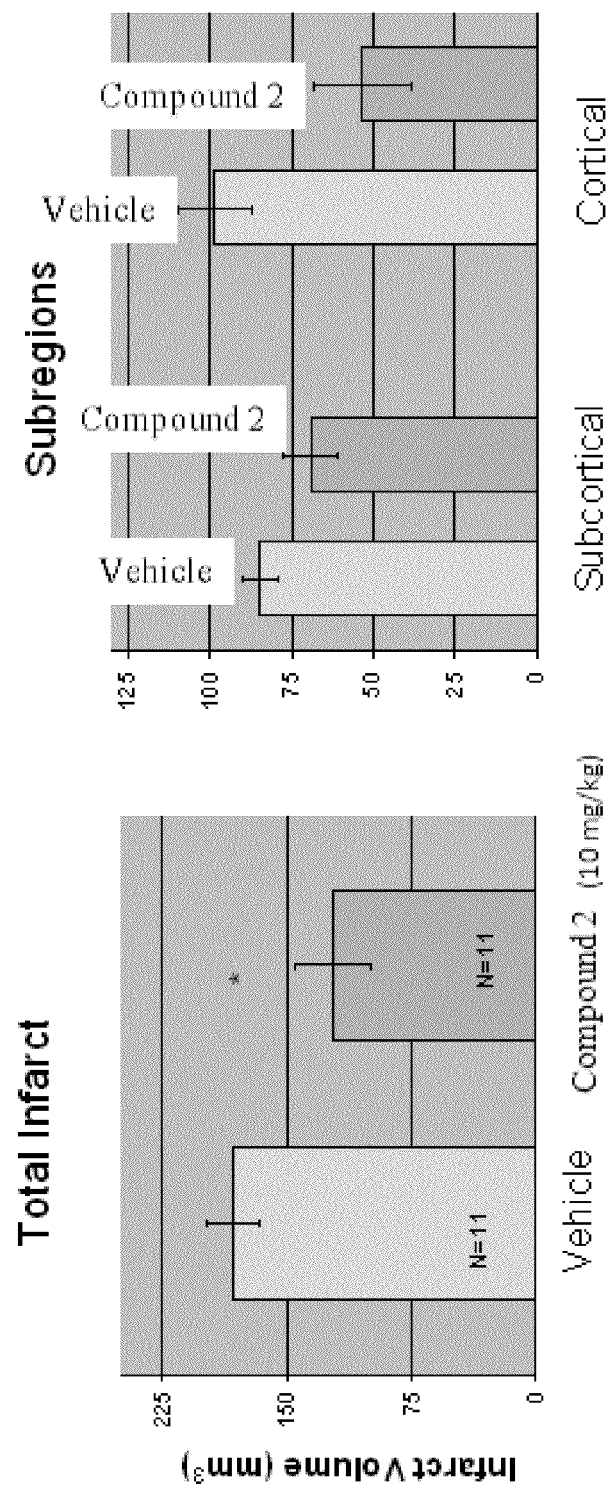

FIG. 11: Efficacy Study of compound 2 in Rat tMCAO Model (Single IV Dose, 4 hrs Post Occlusion).

Figure 12:
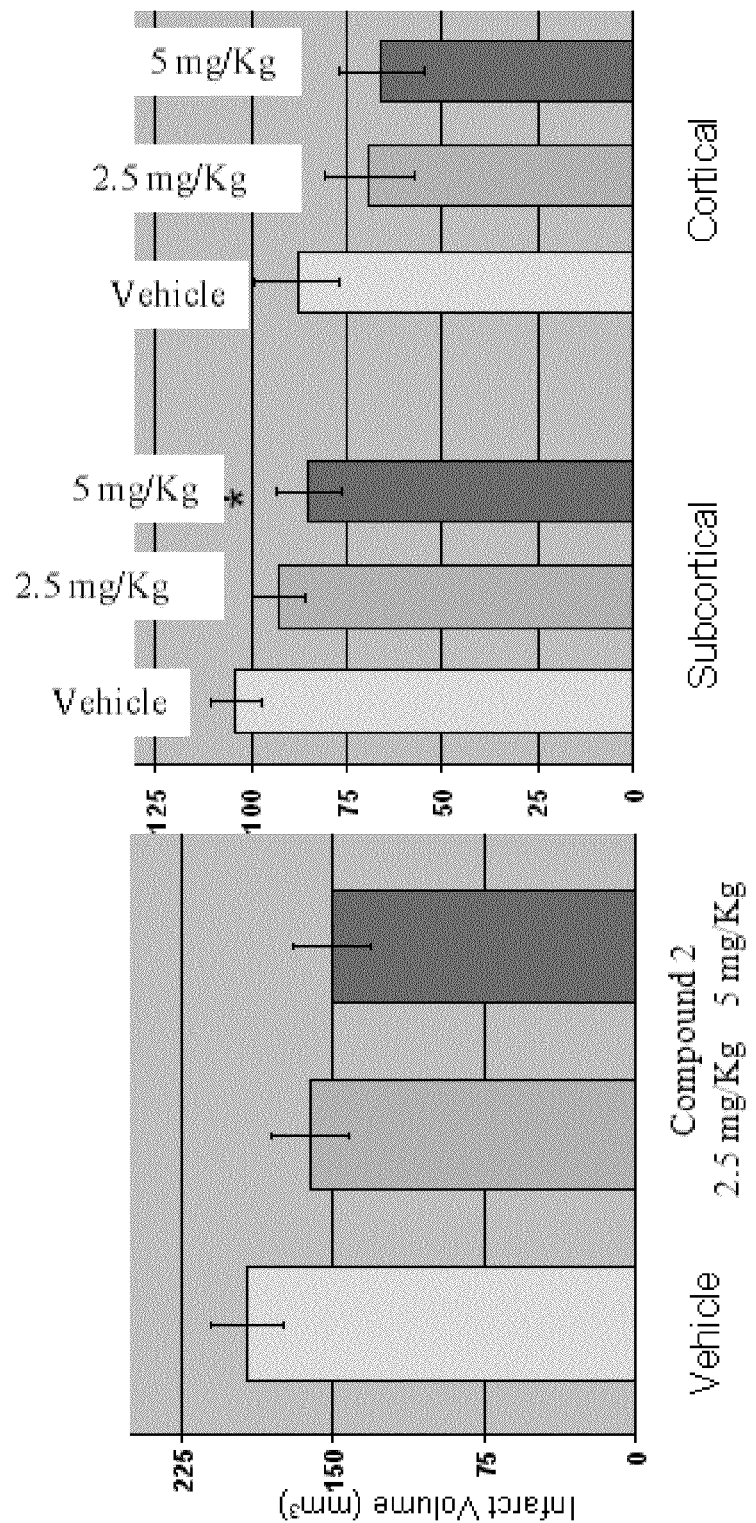

FIG. 12: Efficacy Study of compound 2 in Rat tMCAO Model (Single IV Dose (2.5 mg/Kg or 5 mg/Kg), 4 hrs Post Occlusion).

Figure 13:
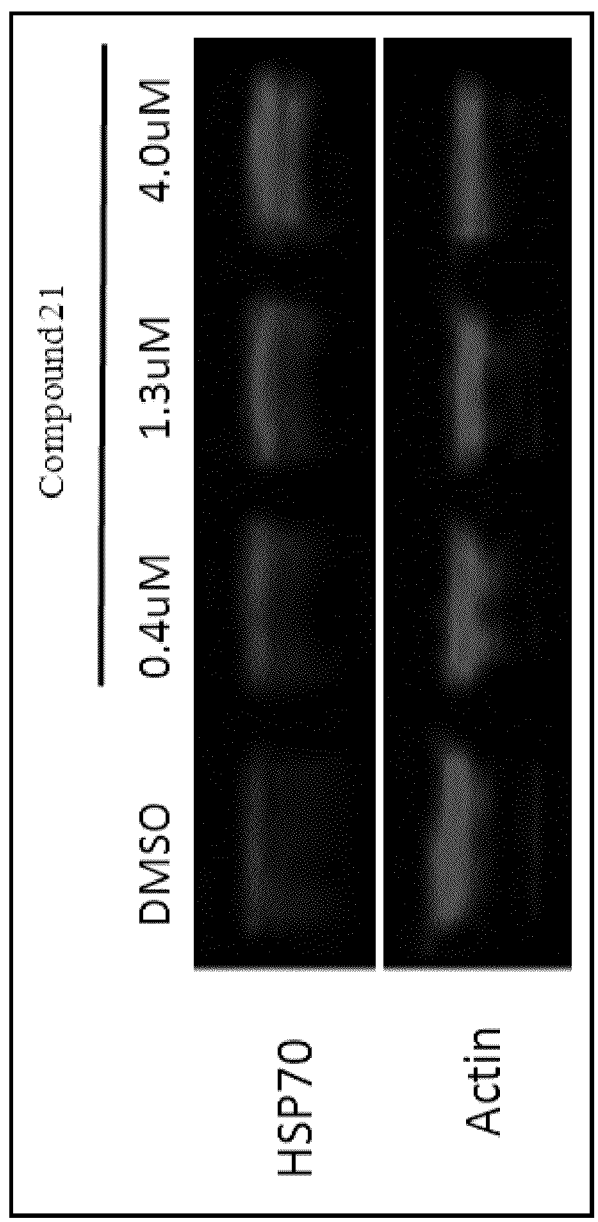

FIG. 13: Compound 21 induces HSP70 up-regulation in primary hippocampal neuron culture.

Figure 14:
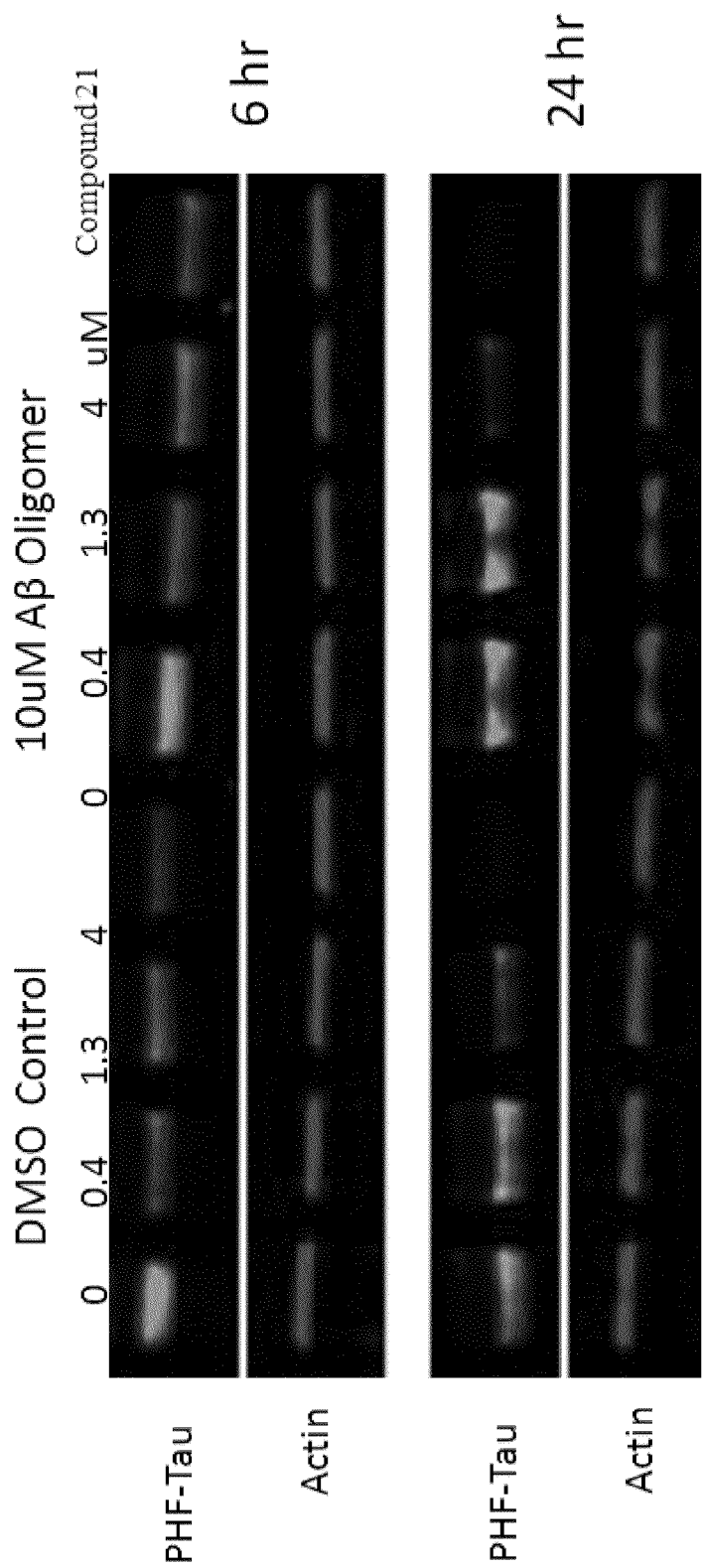

FIG. 14: Compound 21 decreases PHF-tau level in primary hippocampal neuron cultures.

Figure 15A:
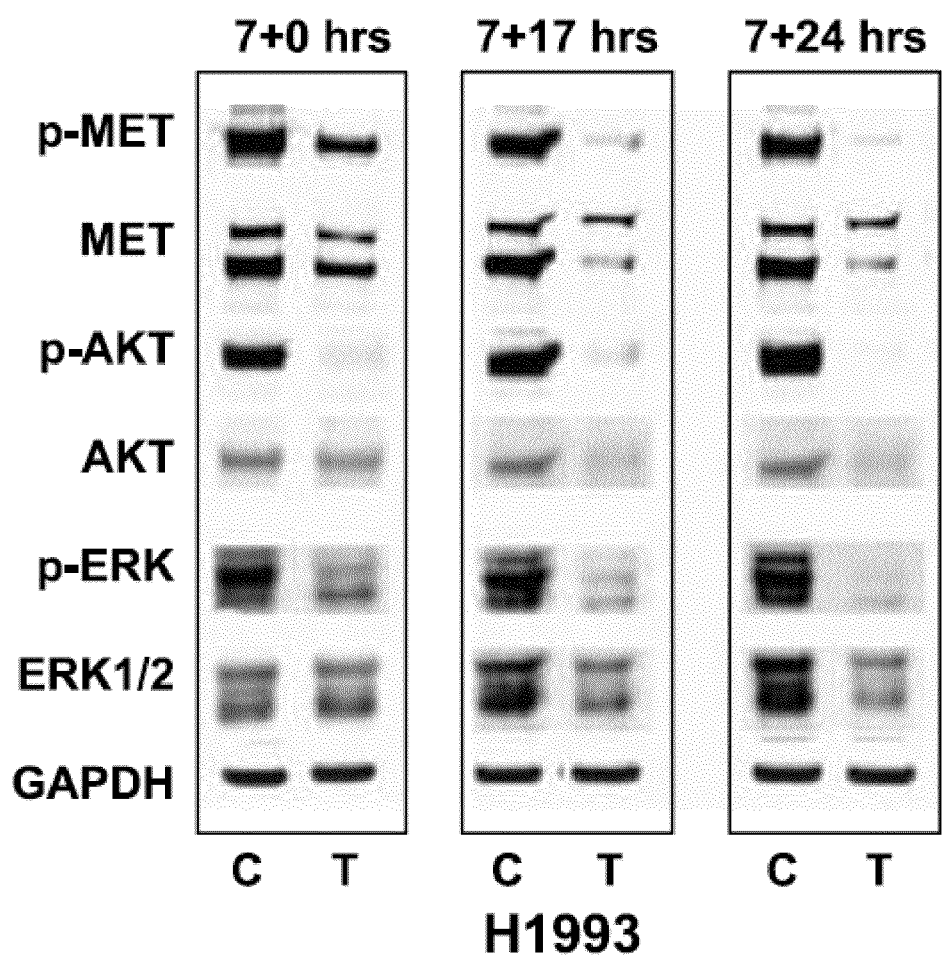

FIG. 15A: Comparison of control (C, DMSO treated) and Compound 15 treated (T) H1993 NSCLC cells. Results indicate that phosphorylated and total EGFR, MET, AKT, and MAPK (ERK) are durably inhibited by a short-term treatment with Compound 15.

Figure 15B:
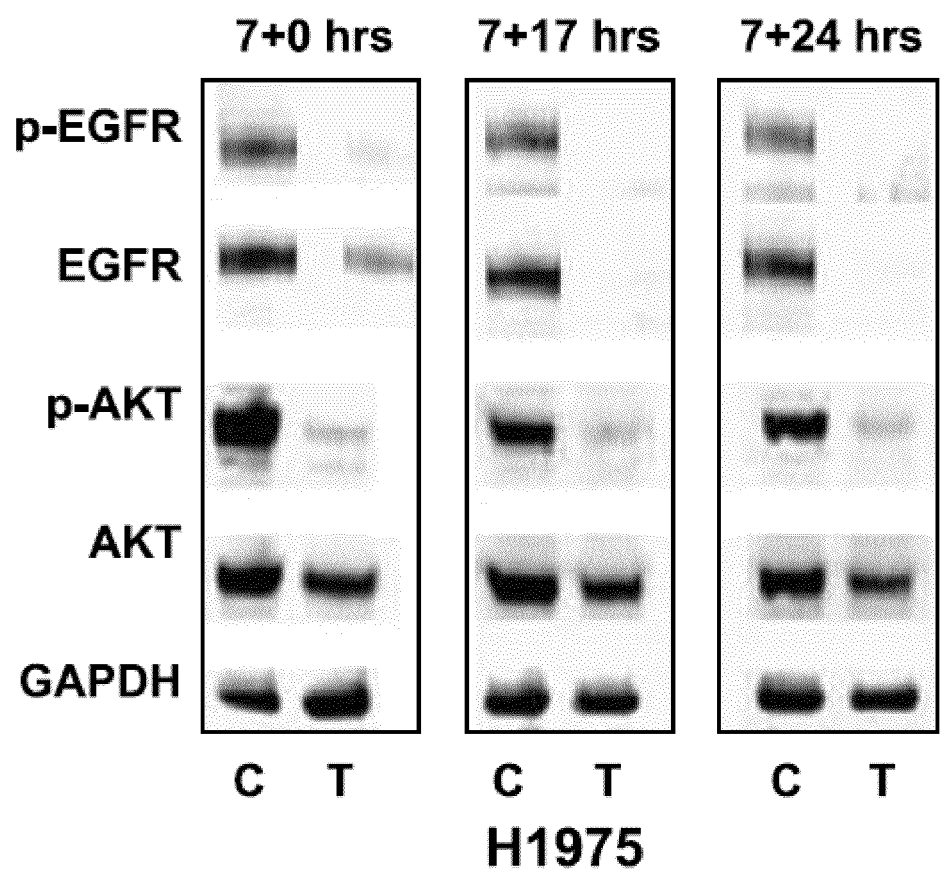

FIG. 15B: Comparison of control (C, DMSO treated) and Compound 15 treated (T) H1975 NSCLC cells. Results indicate that phosphorylated and total EGFR, MET, AKT, and MAPK (ERK) are durably inhibited by a short-term treatment with Compound-15.

Figure 16:
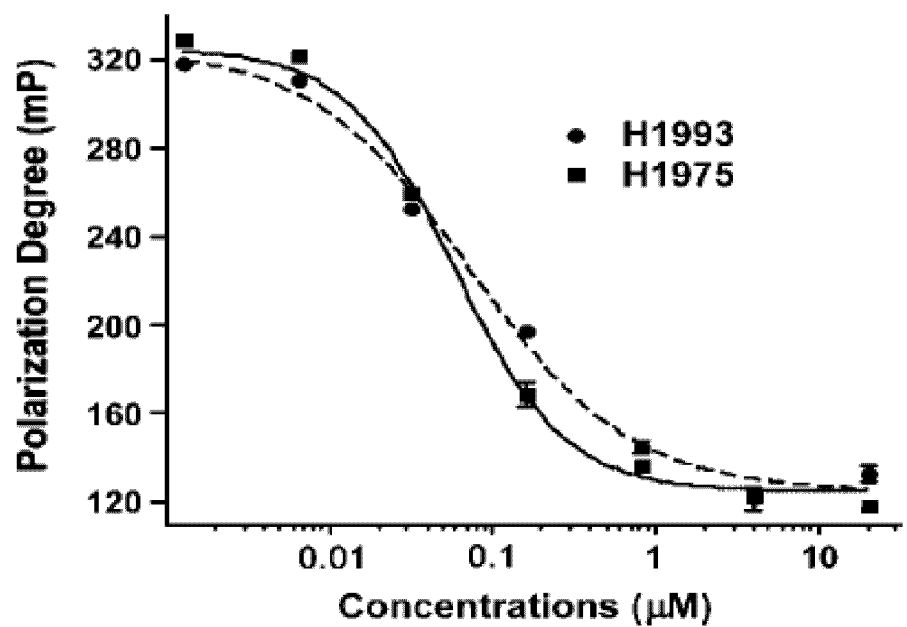

FIG. 16: Fluorescence polarization competition binding assays were done with H1975 and H1993 NSCLC cancer cell extracts with competition from fluorescein isothiocyanate-labeled geldanamycin in the presence of varying concentrations of Compound-15.

Figure 17:
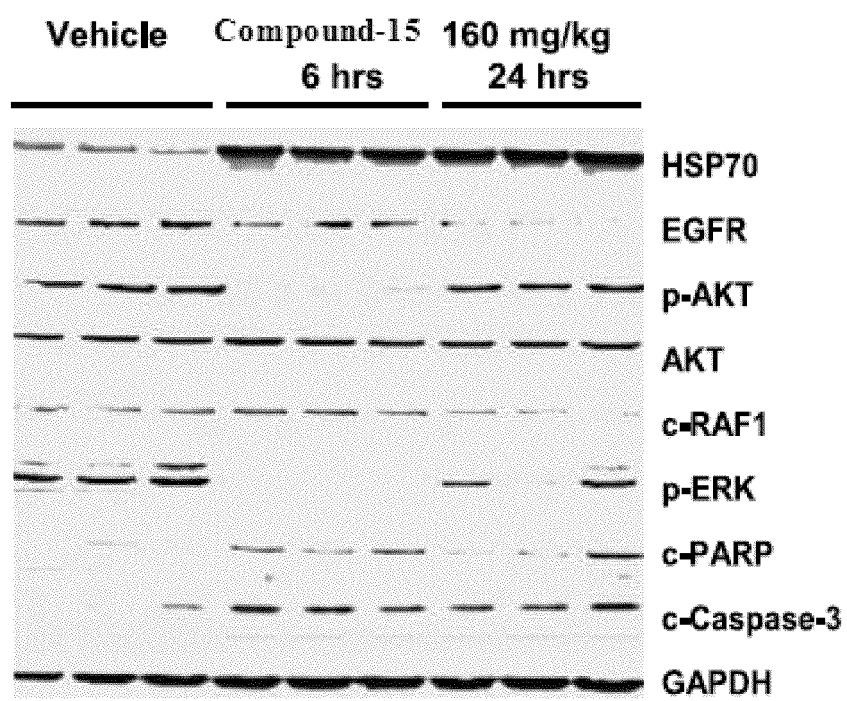

FIG. 17: Inhibition of HSP90 Client Proteins by Compound-15.

Figure 18A:
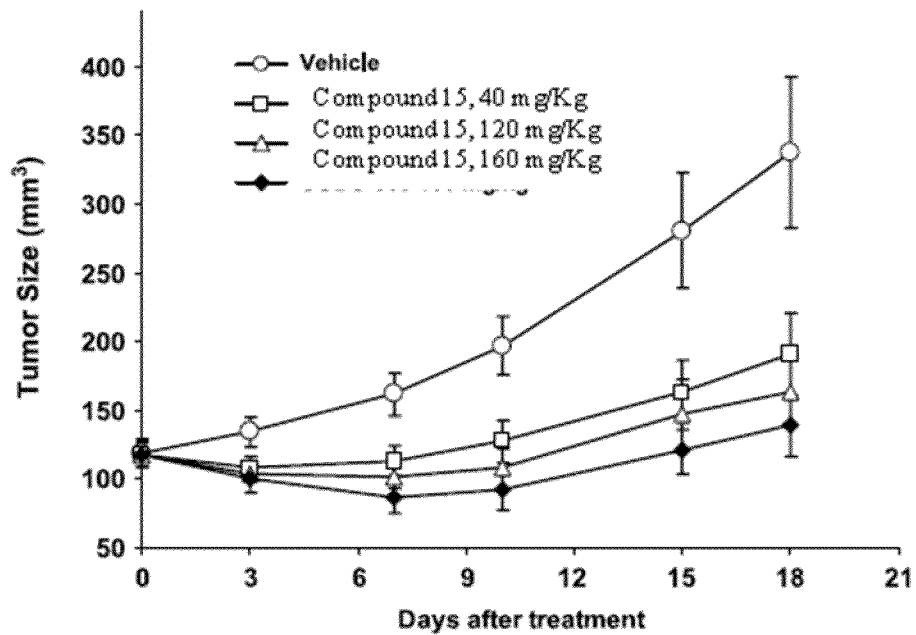

FIG. 18A: Efficacy study of Compound-15 in the H1975 NSCLC subcutaneous tumor model.

Figure 18B:
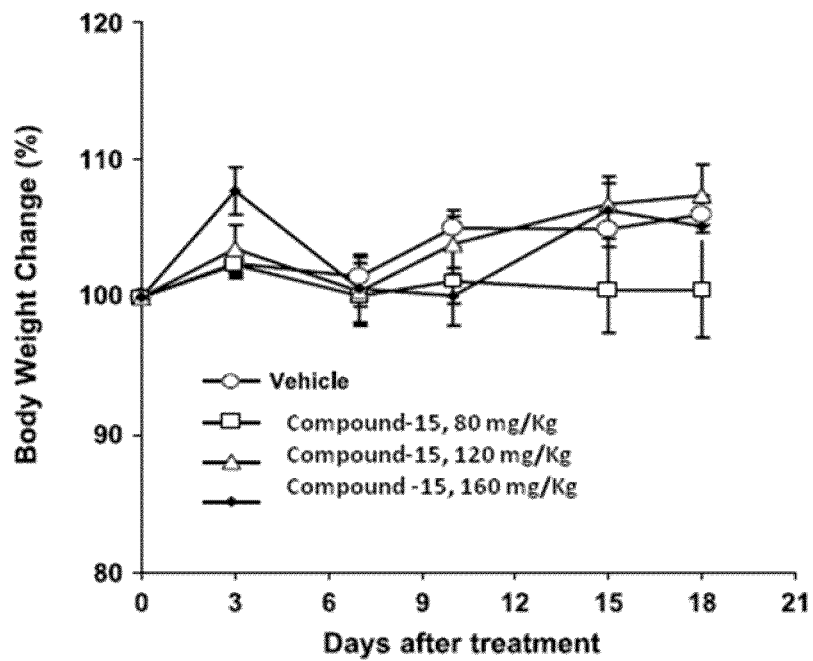

FIG. 18B: Animal body weight changes relative to pre-treatment values in an efficacy study in the H1975 NSCLC subcutaneous tumor model (n=8).

Figure 19A:
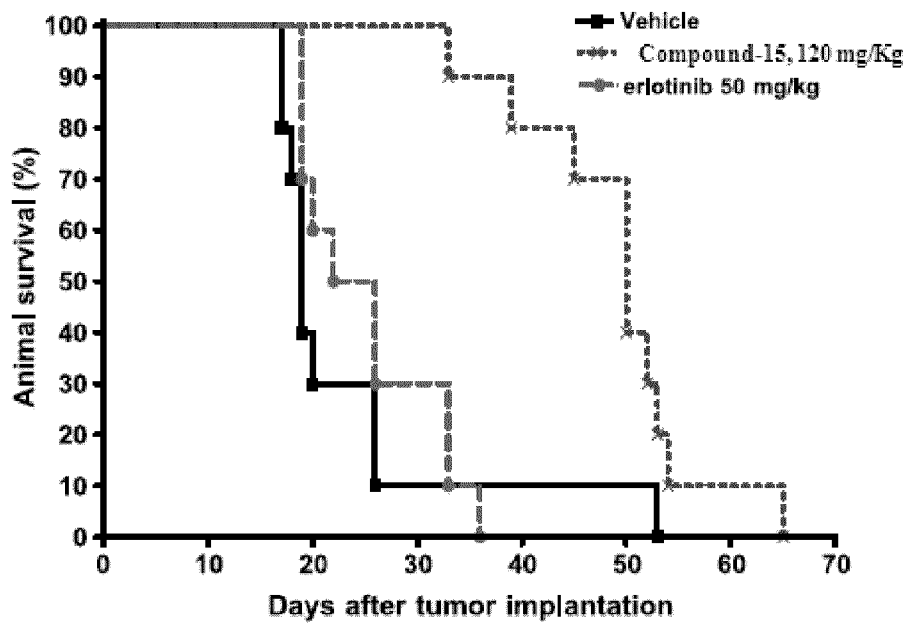

FIG. 19A: Efficacy study of Compound-15 in H1975 NSCLC orthotopic lung tumor model in comparison with erlotinib.

Figure 19B:
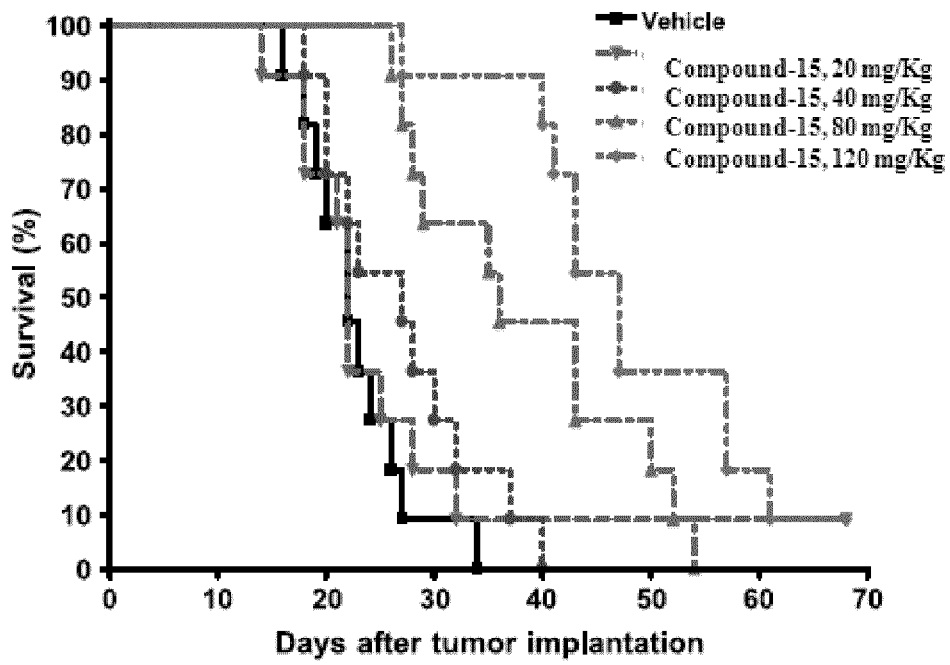

FIG. 19B: Dose-dependent efficacy of Compound-15 in H1975 NSCLC orthotopic lung tumor model.

Figure 19C:
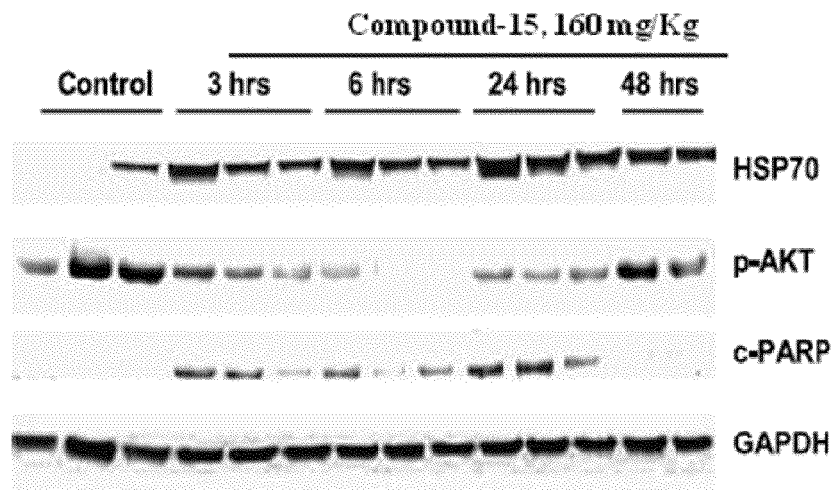

FIG. 19C: Pharmacodynamic study of Compound-15 in H1975 NSCLC orthotopic lung tumor model.

Figure 19D:
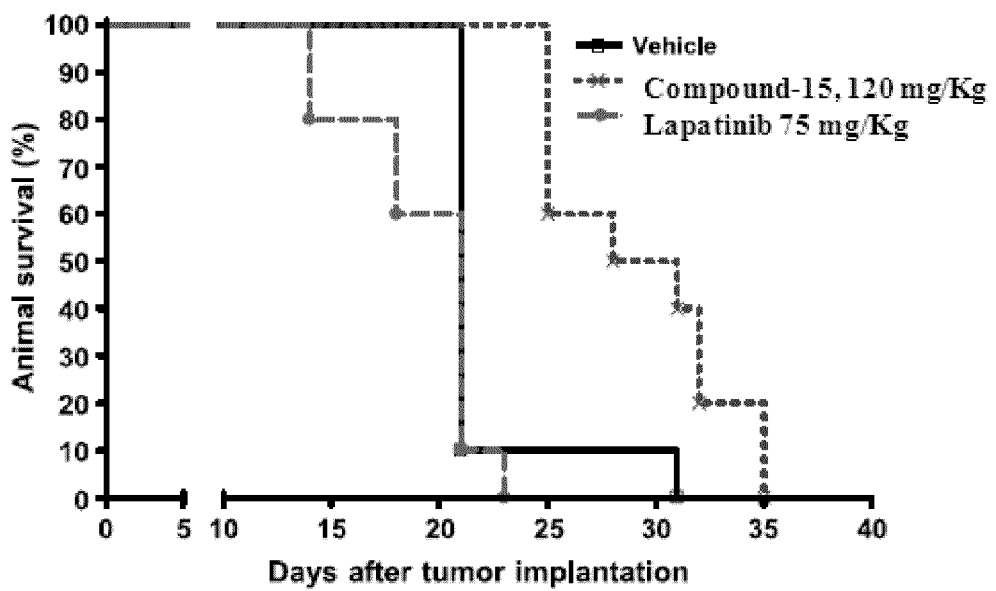

FIG. 19D: Efficacy study of Compound-15 in H1975 NSCLC orthotopic lung tumor model in comparison with lapatinib.

Figure 20A:
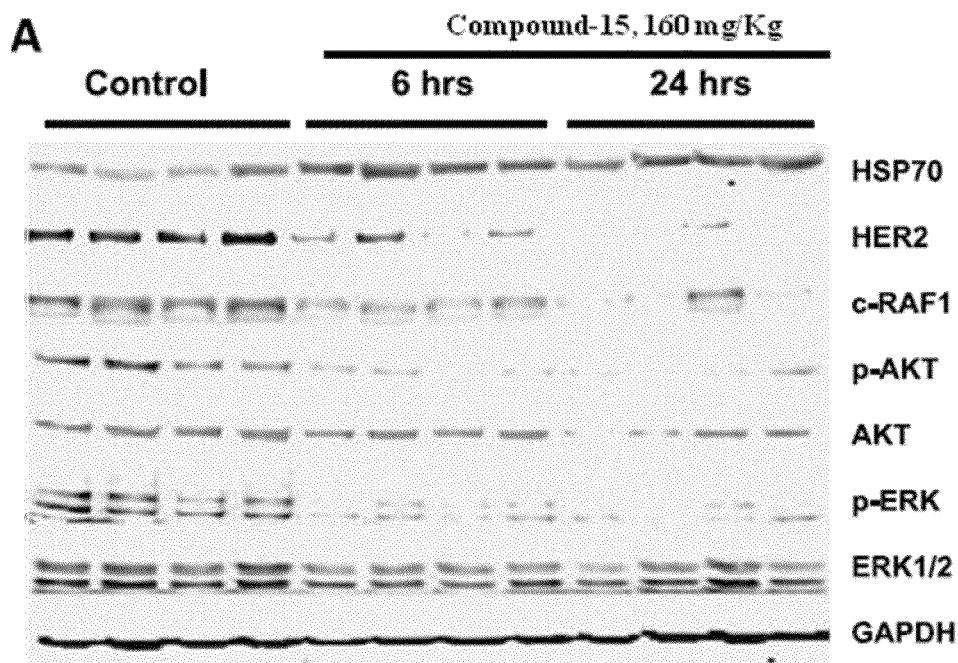

FIG. 20A: Pharmacodynamic study in K-ras-mutated A549 (human lung adenocarcinoma epithelial cell line) subcutaneous tumors.

Figure 20B:
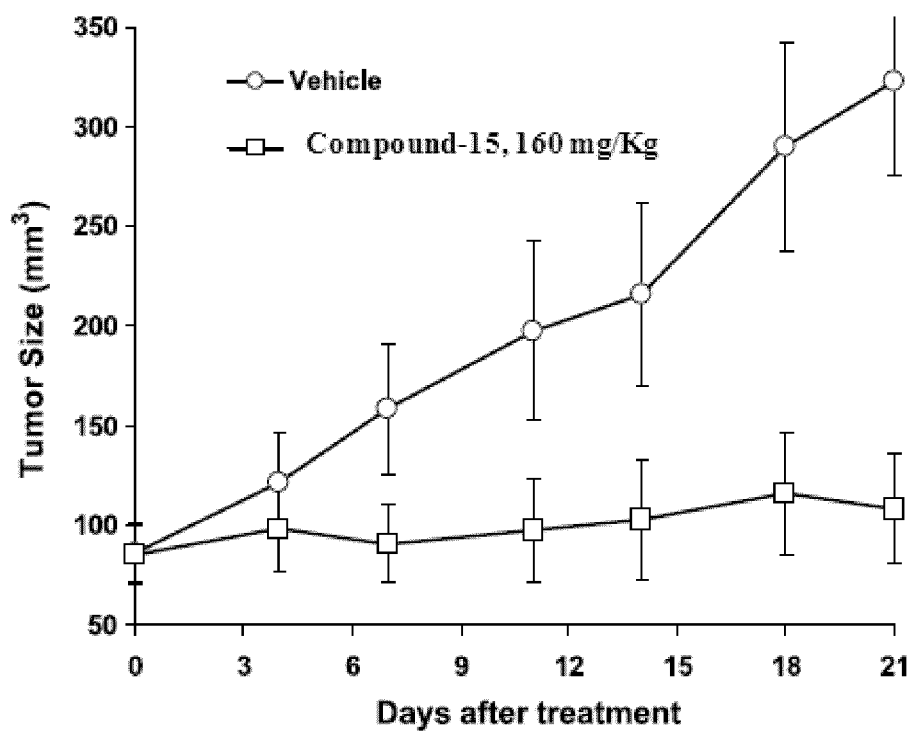

FIG. 20B: Efficacy study of Compound-15 in A549 subcutaneous tumor model.

Figure 20C:
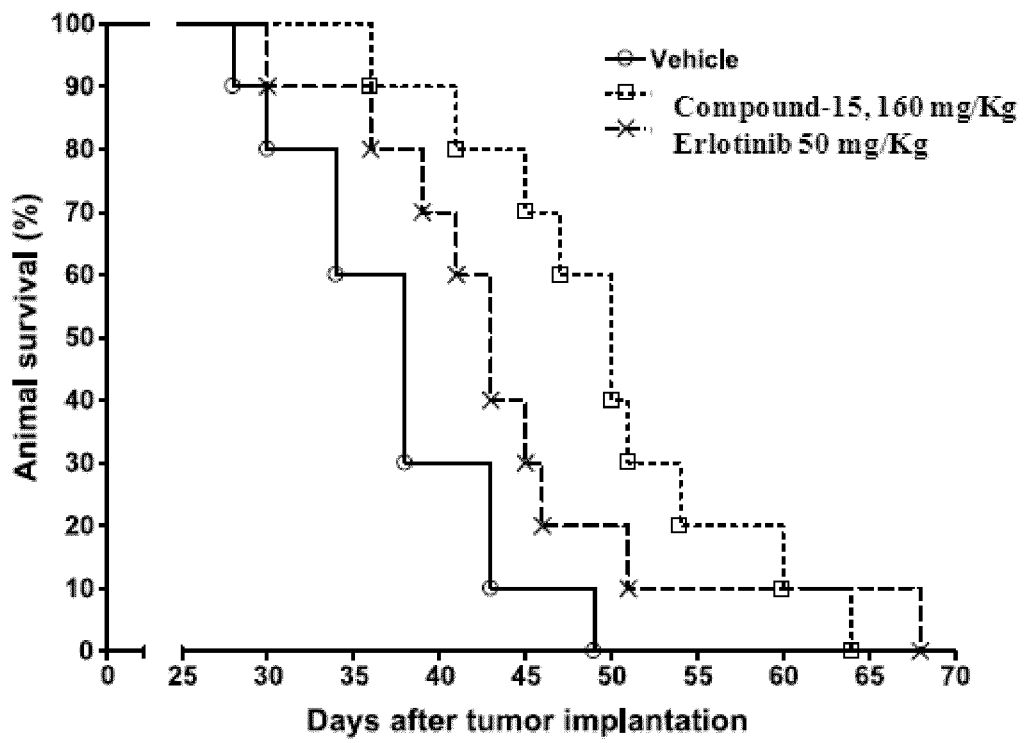

FIG. 20C: Efficacy study in A549 orthotopic lung tumor model.

Figure 20D:
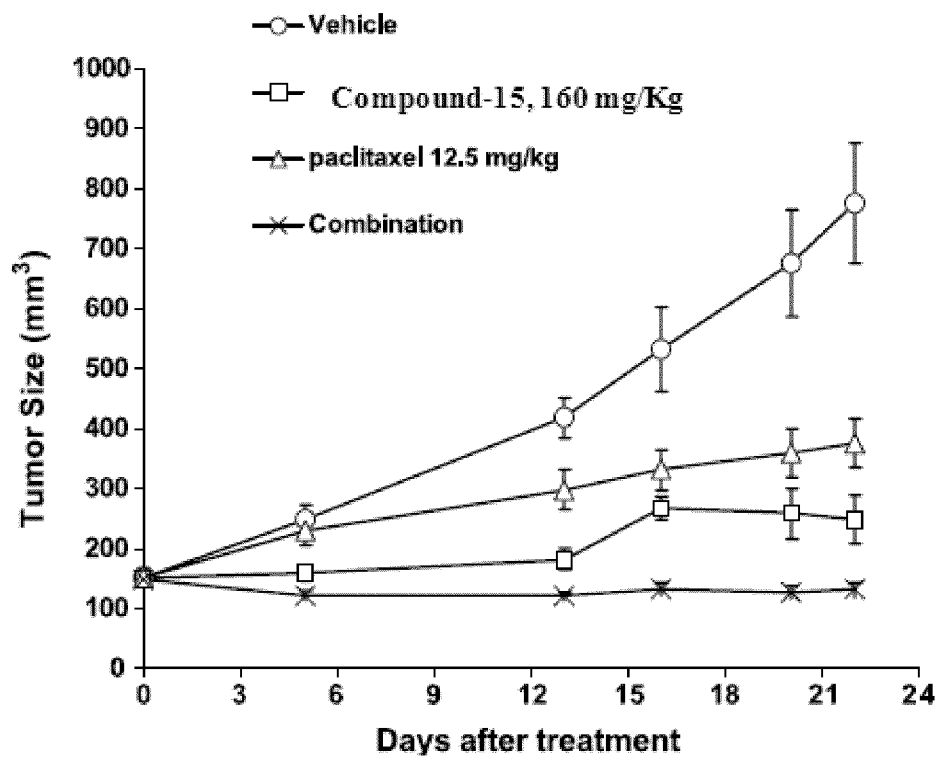

FIG. 20D: Efficacy study of Compound-15 in combination with paclitaxel in A549 orthotopic lung tumor model.

Figure 21A:
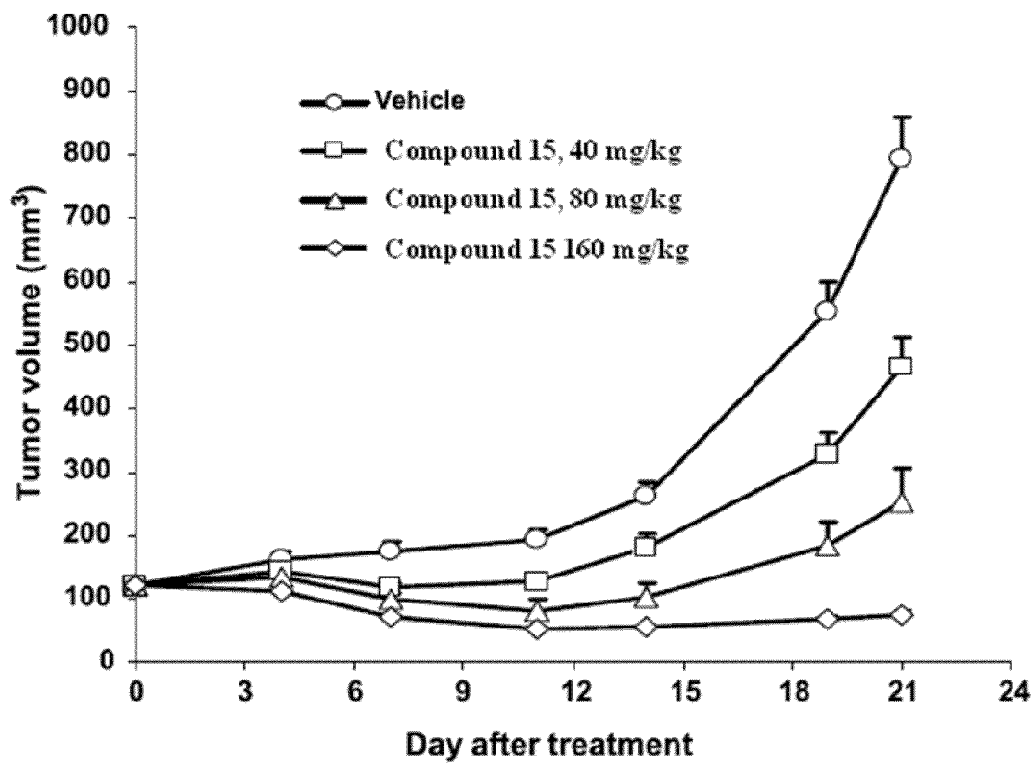

FIG. 21A: Tumor growth after oral delivery of Compound 15 in various doses.

Figure 21B:
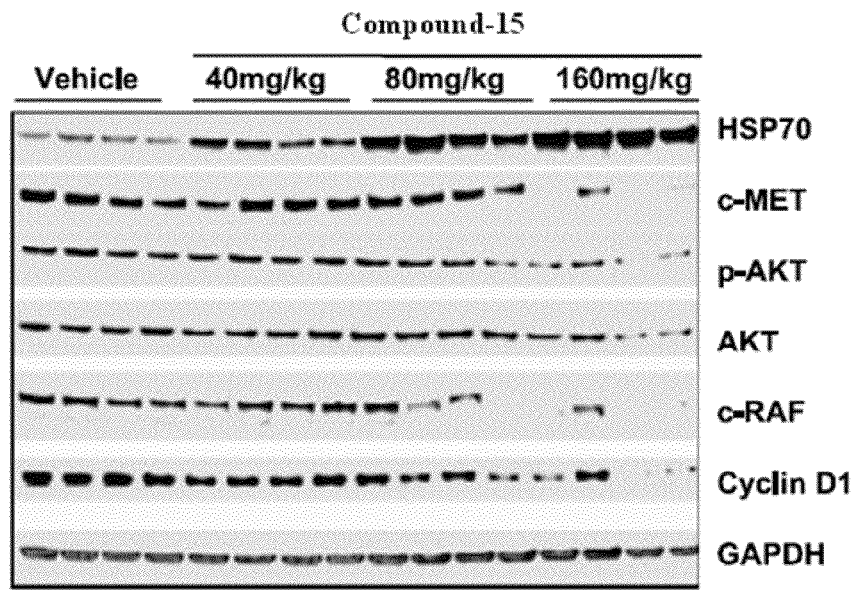

FIG. 21B: Pharmacodynamic analysis (Western Blot) of tumors in mice treated with 40, 80 or 160 mg/kg (q2d).

Figure 22A:
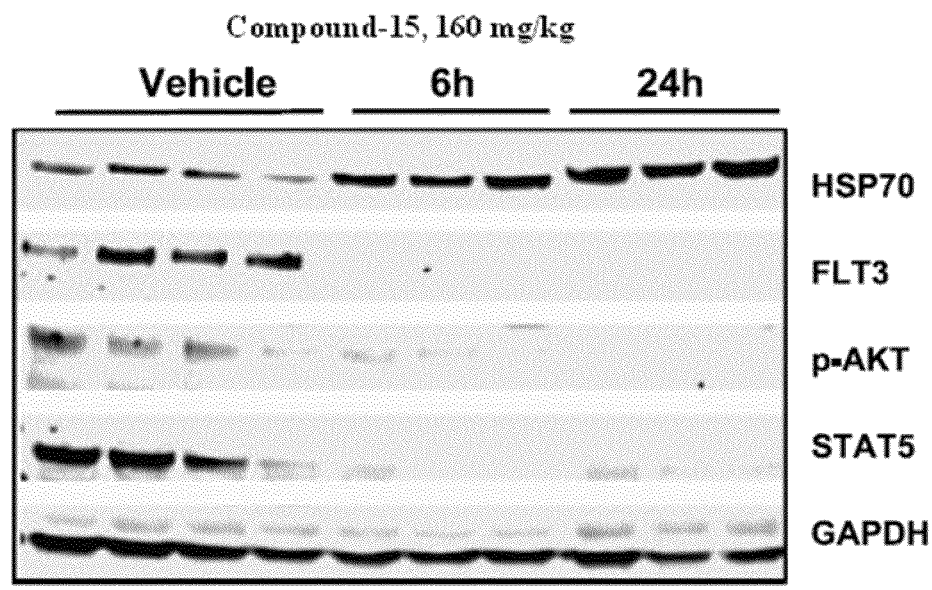

FIG. 22A: Efficacy study of Compound-15 in MV4-11 (human lymphoblast cell line) s.c. tumor model.

Figure 22B:
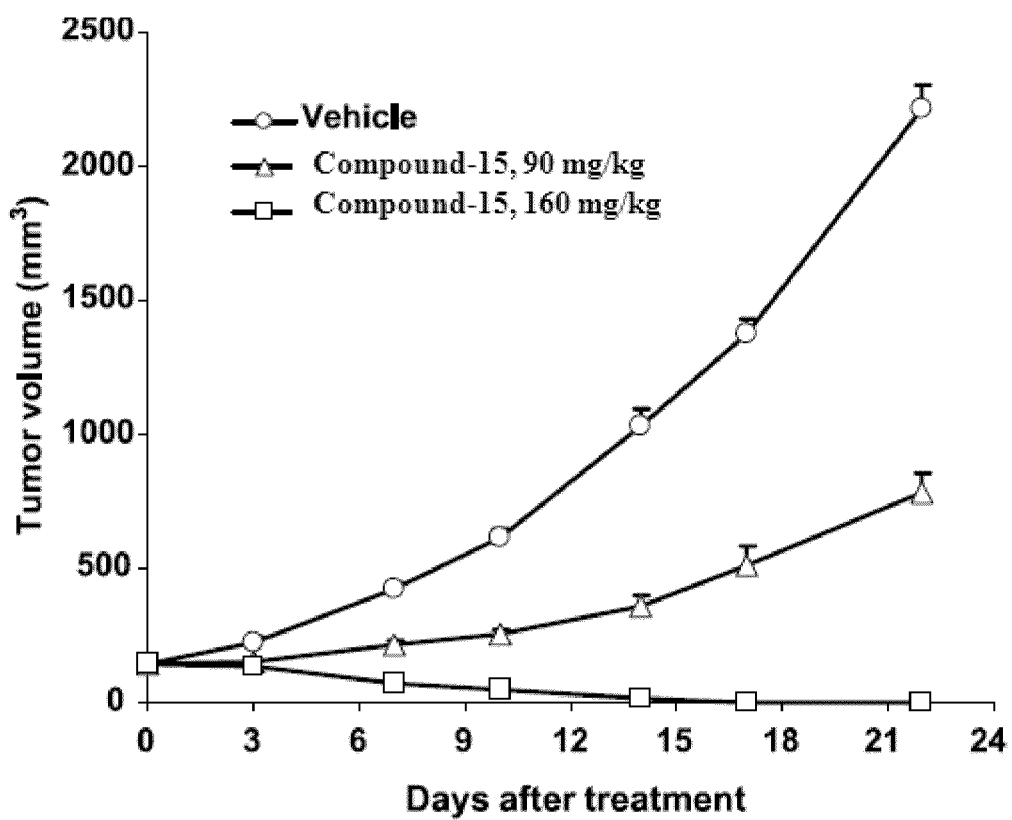

FIG. 22B: Efficacy study of Compound-15 in MV4-11 s.c. tumor model with pretreatment tumor volume of 146 mm$^3$.

Figure 22C:
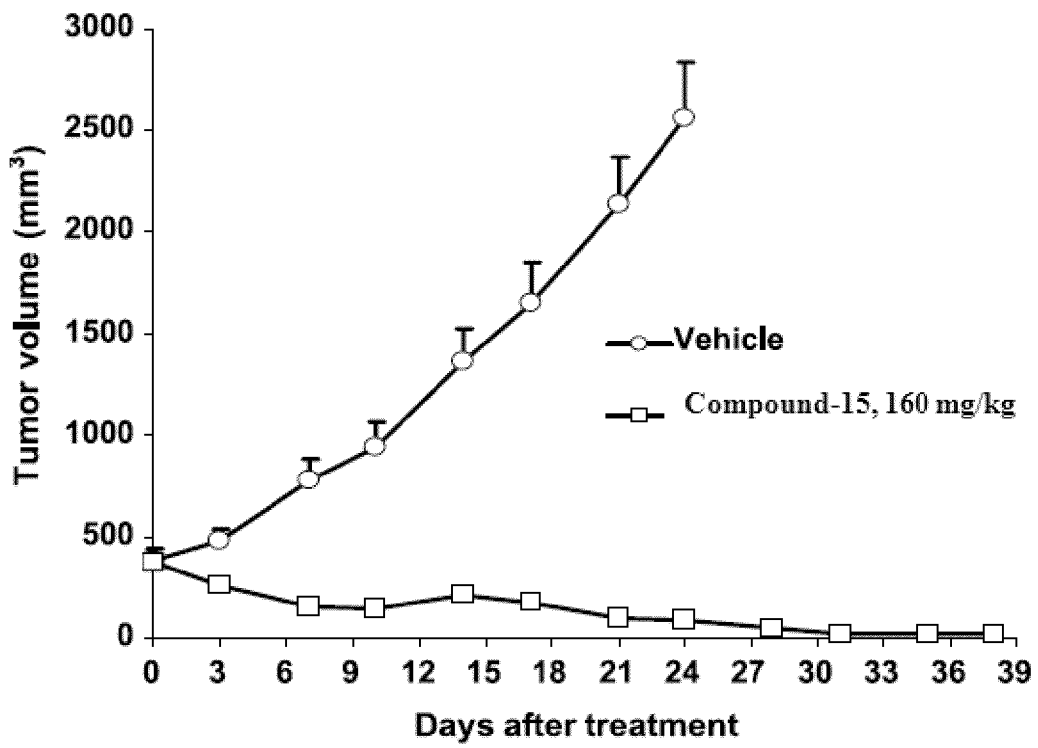

FIG. 22C: Efficacy study of Compound-15 in MV4-11 s.c. tumor model with pretreatment tumor volume of 380 mm$^3$.

Figure 22D:
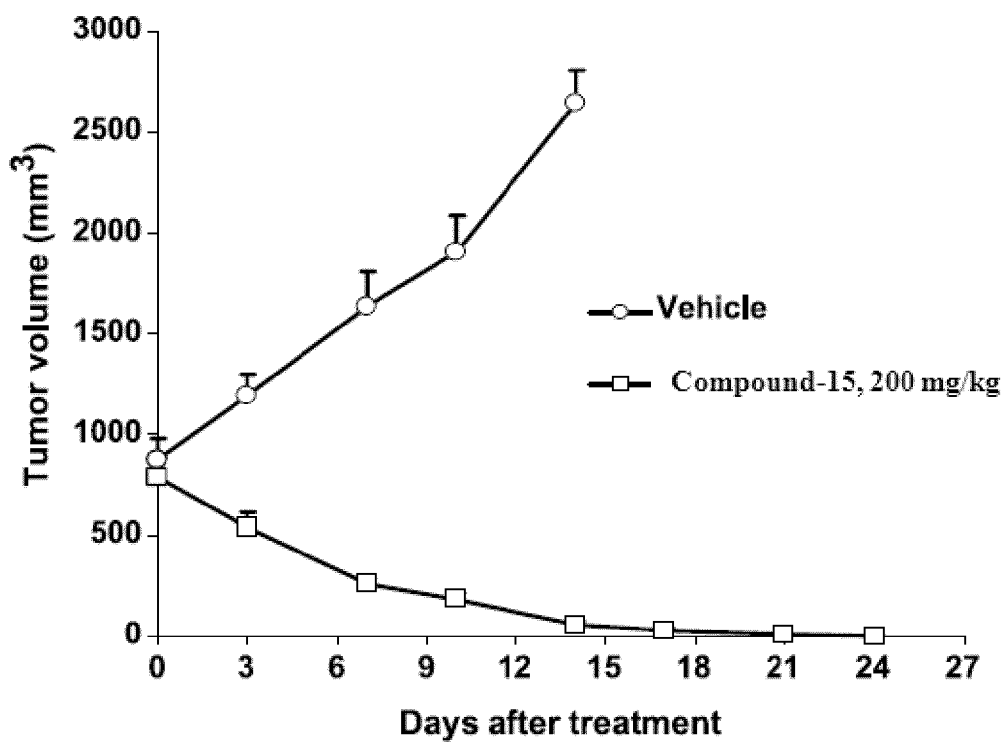

FIG. 22D: Efficacy study of Compound-15 in MV4-11 s.c. tumor model with pretreatment tumor volume of 835 mm$^3$.

Figure 23A:
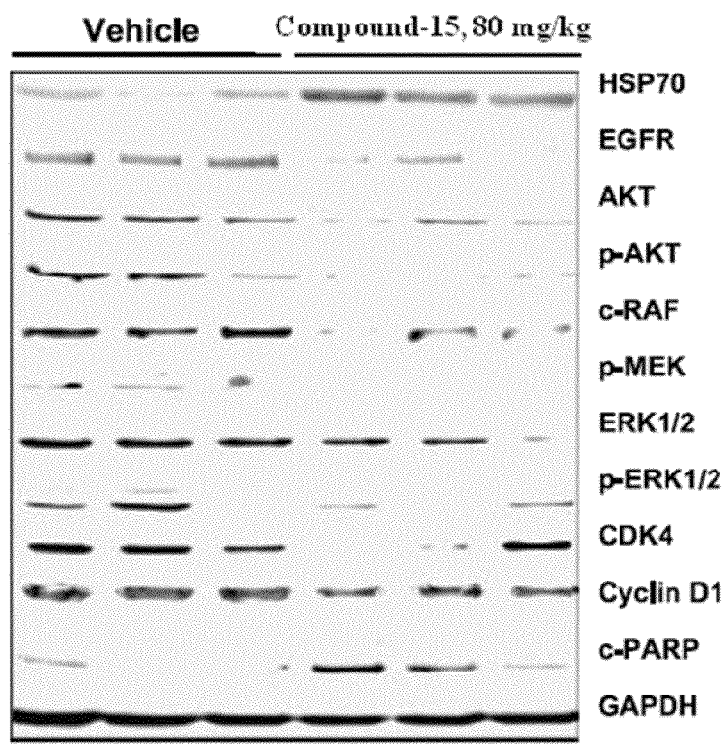

FIG. 23A: Efficacy study of Compound-15 in H1975 NSCLC s.c. tumor model.

Figure 23B:
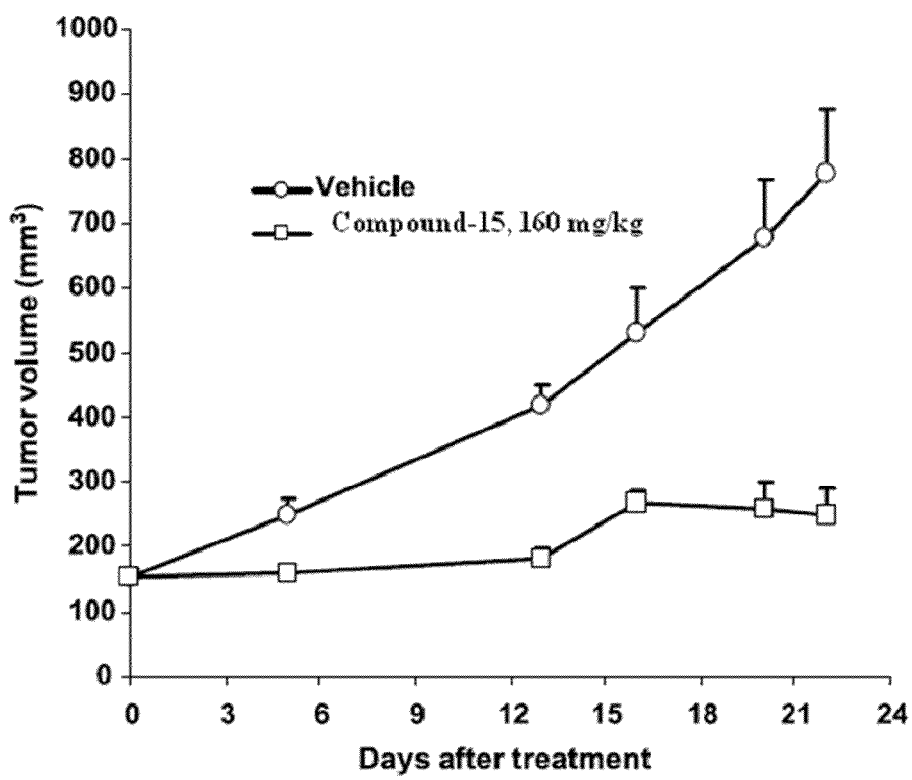

FIG. 23B: Efficacy study of Compound-15 in H1975 NSCLC s.c. tumor model.

Figure 23C:
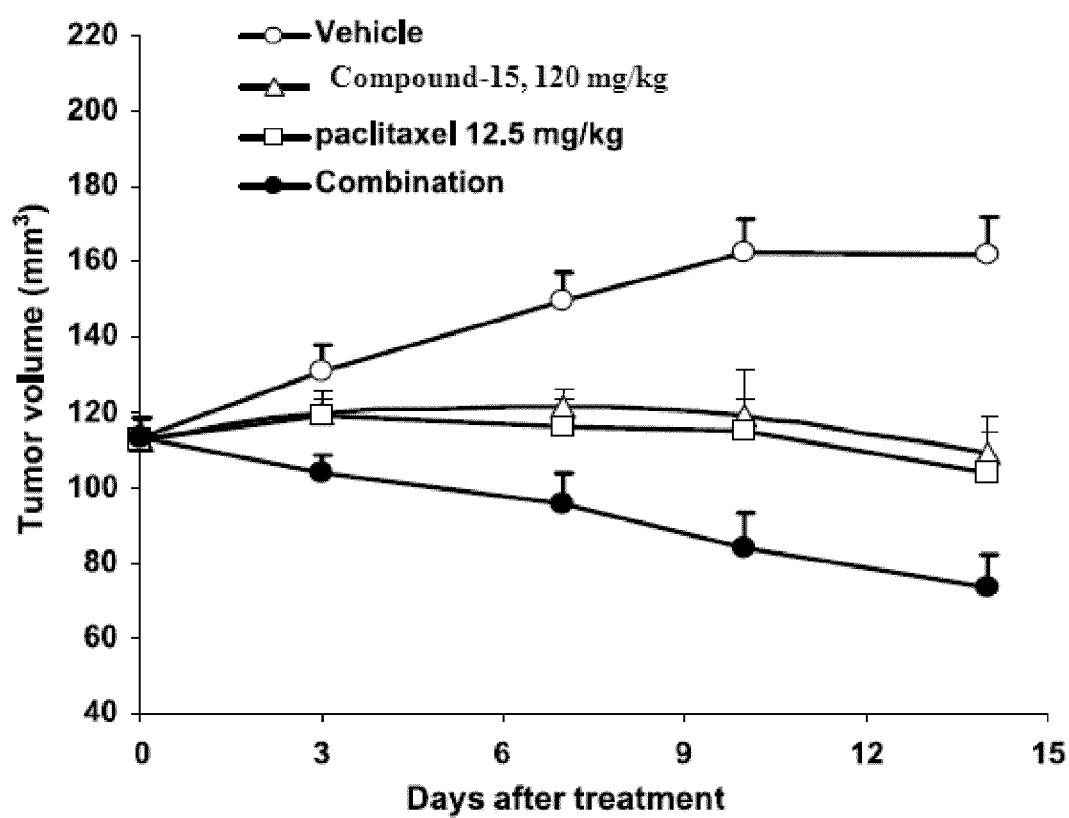

FIG. 23C: Efficacy study of Compound-15 in combination with paclitaxel in H1975 NSCLC s.c. tumor model.

Figure 23D:
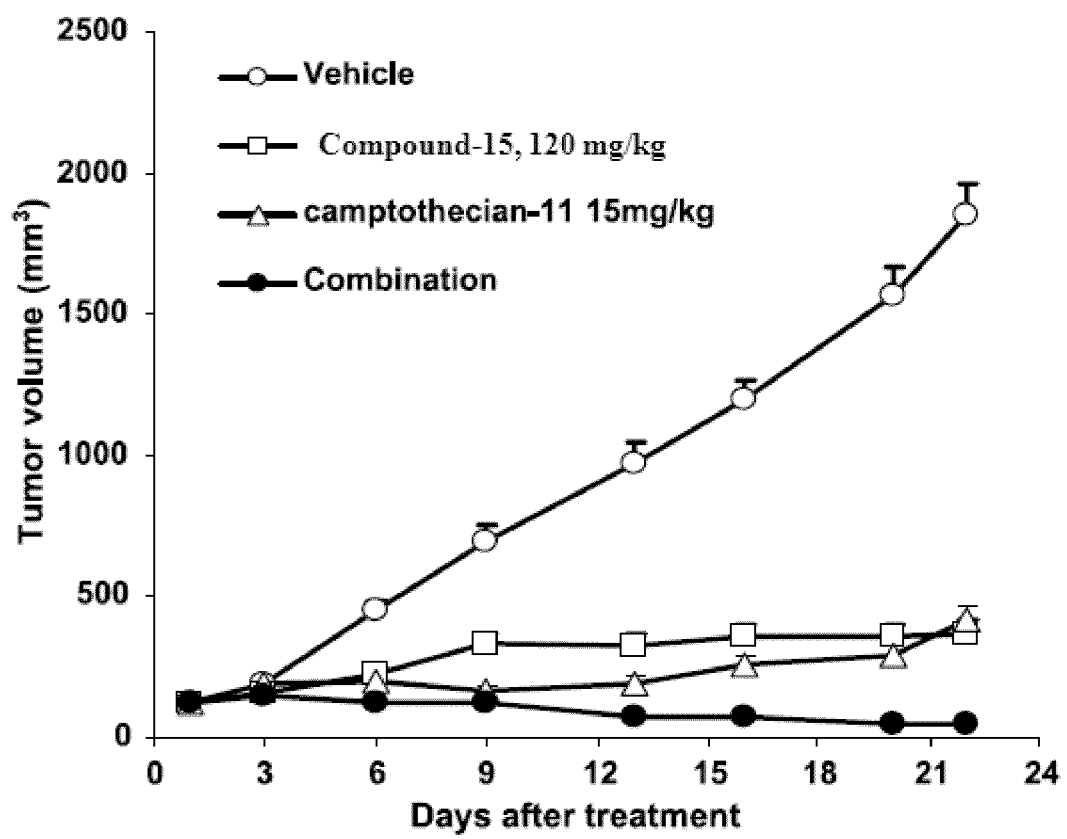

FIG. 23D: Efficacy study of Compound-15 in combination with camptothecin in H1975 NSCLC s.c. tumor model.

The instant invention relates to the use of compounds of Formula I for the treatment of brain related disorders including brain tumors, malignancies, metastases and neurodegenerative diseases, as well as for the treatment of lung related disorders including neoplastic lung disorders such as non-small cell lung cancer. Compounds of the formula I have been described in the co-pending applications No. 12/045,509 (US Patent Application Publication No. 20080234314 A1) and 61/015,288, the entire contents of which are incorporated by reference herein. A first embodiment is the use of the compounds represented by formula (I) as illustrated above, or its geometric isomers, enantiomers, diastereomers, racemates, pharmaceutically acceptable salts, prodrugs and solvates thereof for the treatment of brain related disorders.

Representative compounds according to the invention are in the Table A below or pharmaceutically acceptable salts thereof. Preferred compounds according to the invention are compounds 2, 15 and 21.

TABLE A

| Compound # | Structure |
| --- | --- |
| 1 | 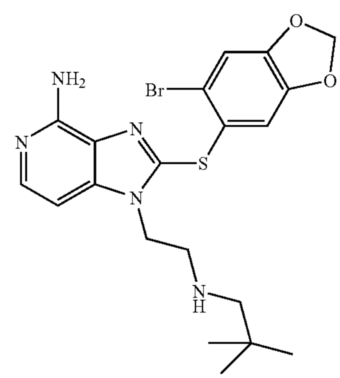 [SMILES: CC(C)(C)CNCCn1c(Sc2cc3c(cc2Br)OCO3)nc2c(N)nccc21] |
| 2 | 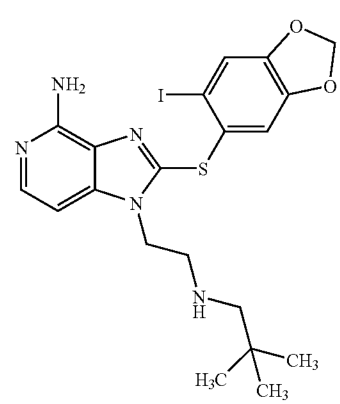 [SMILES: CC(C)(C)CNCCn1c(Sc2cc3c(cc2I)OCO3)nc2c(N)nccc21] |

TABLE A-continued

| Compound # | Structure |
|---|---|
| 3 | (structure) |
| 4 | (structure) |
| 5 | (structure) |
| 6 | (structure) |
| 7 | (structure) |
| 8 | (structure) |
| 9 | (structure) |
| 10 | (structure) |

TABLE A-continued

| Compound # | Structure |
|---|---|
| 11 | (4-amino-imidazo[4,5-c]pyridine with 2-S-(6-iodo-benzo[1,3]dioxol-5-yl) and N1-(3-(neopentylamino)propyl)) |
| 12 | (4-amino-imidazo[4,5-c]pyridine with 2-S-(6-bromo-benzo[1,3]dioxol-5-yl) and N1-(3-(tert-butylamino)propyl)) |
| 13 | (4-amino-imidazo[4,5-c]pyridine with 2-S-(6-iodo-benzo[1,3]dioxol-5-yl) and N1-(3-(tert-butylamino)propyl)) |
| 14 | (4-amino-imidazo[4,5-c]pyridine with 2-S-(6-amino-benzo[1,3]dioxol-5-yl) and N1-(2-(neopentylamino)ethyl)) |
| 15 | (4-amino-imidazo[4,5-c]pyridine with 2-S-(6-dimethylamino-benzo[1,3]dioxol-5-yl) and N1-(2-(neopentylamino)ethyl)) |
| 16 | (4-amino-imidazo[4,5-c]pyridine with 2-S-(6-diethylamino-benzo[1,3]dioxol-5-yl) and N1-(2-(neopentylamino)ethyl)) |
| 17 | (4-amino-imidazo[4,5-c]pyridine with 2-S-(6-methylamino-benzo[1,3]dioxol-5-yl) and N1-(2-(neopentylamino)ethyl)) |
| 18 | (4-amino-imidazo[4,5-c]pyridine with 2-S-(6-ethylamino-benzo[1,3]dioxol-5-yl) and N1-(2-(neopentylamino)ethyl)) |

TABLE A-continued

| Compound # | Structure |
|---|---|
| 19 | (structure) |
| 20 | (structure) |
| 21 | (structure) |
| 22 | (structure) |
| 23 | (structure) |

Compounds of formula I with a cLogP value of about 3.70 or more are considered more effective in crossing the blood brain barrier and, are accordingly, preferred. Preferred compounds have a cLogP value of at least 4.00 and most preferred compounds have a cLogP value of at least 4.20.

The invention further relates to a method of regulating the level of HSP70 in the brain tissue of patient by the oral administration of a compound of formula I to a patient in need thereof.

The invention further relates to a method of treating lung cancer in a patient that fails to respond to treatment by an inhibitor of epidermal growth factor (EGFR). In particular the invention relates to the treatment of lung cancers that have grown resistant to an EGFR inhibitor selected from gefitinib, erlotinib, vandetanib, AEE-788, PKI-166, PTK787/ZK222584, lapatinib, cetuximab, nimotuzumab, matuzumab, panitumumab, trastuzumab and pertuzumab by administration of a compound of formula I. In one embodiment the failure of the EGFR inhibitors refers to decreased effectiveness of an EGFR inhibitor in a patient due to EGFR gene mutations. In one embodiment, the resistance is acquired resistance due to a gene mutation, for example, T790M or D761Y or L858R mutation of the EGFR gene. In one embodiment, the resistance is a primary resistance due to a gene mutation, for example, K-Ras gene mutation.

The term "cancer" refers to any cancer caused by the proliferation of malignant neoplastic cells, such as tumors, neoplasms, carcinomas, sarcomas, leukemias, lymphomas and the like. The present invention is related to treating CNS or brain disorders, in particular cancers of the brain, such as brain tumors (including gliomas such as ependymomas, astrocytomas, gangliogliomas, oligodendrogliomas and glioblastomas), pituitary tumors, neuroblastoma, retinoblastoma, medulloblastoma, and meningioma, and also include metastases of primary tumors from an original site outside of the brain or CNS. The present invention is related to treating lung related disorders such as small cell lunch cancer, non-small cell lung cancers including adenocarcinoma, squamous cell lung carcinoma, large cell lung carcinoma.

It will be appreciated that compound of the inventions can be useful in treating "neurodegenerative diseases" including Huntington's disease, Polyglutamine disease, Parkinson's disease, Alzheimer's disease, Seizures, Striatonigral degeneration, Progressive supranuclear palsy, Torsion dystonia, Spasmodic torticollis and dyskinesis, Familial tremor, Gilles de la Tourette syndrome, Diffuse Lewy body disease, Progressive supranuclear palsy, Pick's disease, intracerebral hemorrhage, Primary lateral sclerosis, Spinal muscular atrophy, Amyotrophic lateral sclerosis, Hypertrophic interstitial polyneuropathy, Hereditary spastic paraplegia, Progressive ataxia and Shy-Drager syndrome.

In one embodiment, the present invention includes the use of one or more compounds of the invention in the manufacture of a medicament that prevents further aberrant proliferation, differentiation, or survival of cells. For example, compounds of the invention may be useful in preventing tumors from increasing in size or from reaching a metastatic state. The subject compounds may be administered to halt the progression or advancement of cancer. In addition, the instant invention includes use of the subject compounds to prevent a recurrence of cancer.

"Combination therapy" includes the administration of the subject compounds in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, preferably compounds that are able to enhance the effect of the compounds of the invention. The compounds of the invention can be administered simultaneously (as a single preparation or separate preparation) or sequentially to the other drug therapy. In general, a combination therapy envisions administration of two or more drugs during a single cycle or course of therapy.

In one aspect of the invention, the subject compounds may be administered in combination with one or more separate agents that modulate protein kinases involved in various disease states. Examples of such kinases may include, but are not limited to: serine/threonine specific kinases, receptor tyrosine specific kinases and non-receptor tyrosine specific kinases. Serine/threonine kinases include mitogen activated protein kinases (MAPK), meiosis specific kinase (MEK), RAF and aurora kinase. Examples of receptor kinase families include epidermal growth factor receptor (EGFR) (e.g. HER2/neu, HER3, HER4, ErbB, ErbB2, ErbB3, ErbB4, Xmrk, DER, Let23); fibroblast growth factor (FGF) receptor (e.g. FGF-R1, GFF-R2/BEK/CEK3, FGF-R3/CEK2, FGF-R4/TKF, KGF-R); hepatocyte growth/scatter factor receptor (HGFR) (e.g., MET, RON, SEA, SEX); insulin receptor (e.g. IGFI-R); Eph (e.g. CEK5, CEK8, EBK, ECK, EEK, EHK-1, EHK-2, ELK, EPH, ERK, HEK, MDK2, MDK5, SEK); Ax1 (e.g. Mer/Nyk, Rse); RET; and platelet-derived growth factor receptor (PDGFR) (e.g. PDGFα-R, PDGFβ-R, CSF1-R/FMS, SCF-R/C-KIT, VEGF-R/FLT, NEK/FLK1, FLT3/FLK2/STK-1). Non-receptor tyrosine kinase families include, but are not limited to, BCR-ABL (e.g. p43$^{abl}$, ARG); BTK (e.g. ITK/EMT, TEC); CSK, FAK, FPS, JAK, SRC, BMX, FER, CDK and SYK.

In another aspect of the invention, the subject compounds may be administered in combination with one or more separate agents that modulate non-kinase biological targets or processes. Such targets include histone deacetylases (HDAC), DNA methyltransferase (DNMT), and proteosomes.

In a preferred embodiment, subject compounds may be combined with antineoplastic agents (e.g. small molecules, monoclonal antibodies, antisense RNA, and fusion proteins) that inhibit one or more biological targets such as Zolinza, Tarceva, Iressa, Tykerb, Gleevec, Sutent, Sprycel, Nexavar, Sorafinib, CNF2024, RG108, BMS387032, Affinitak, Avastin, Herceptin, Erbitux, AG24322, PD325901, ZD6474, PD184322, Obatodax, ABT737 and AEE788. Such combinations may enhance therapeutic efficacy over efficacy achieved by any of the agents alone and may prevent or delay the appearance of resistant mutational variants.

In certain preferred embodiments, the compounds of the invention are administered in combination with a chemotherapeutic agent. Chemotherapeutic agents encompass a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment. Examples of such agents include, but are not limited to, alkylating agents such as mustard gas derivatives (Mechlorethamine, cylophosphamide, chlorambucil, melphalan, ifosfamide), ethylenimines (thiotepa, hexamethylmelanine), Alkylsulfonates (Busulfan), Hydrazines and Triazines (Altretamine, Procarbazine, Dacarbazine and Temozolomide), Nitrosoureas (Carmustine, Lomustine and Streptozocin), Ifosfamide and metal salts (Carboplatin, Cisplatin, and Oxaliplatin); plant alkaloids such as Podophyllotoxins (Etoposide and Tenisopide), Taxanes (Paclitaxel and Docetaxel), Vinca alkaloids (Vincristine, Vinblastine, Vindesine and Vinorelbine), and Camptothecan analogs (Irinotecan and Topotecan); anti-tumor antibiotics such as Chromomycins (Dactinomycin and Plicamycin), Anthracyclines (Doxorubicin, Daunorubicin, Epirubicin, Mitoxantrone, Valrubicin and Idarubicin), and miscellaneous antibiotics such as Mitomycin, Actinomycin and Bleomycin; anti-metabolites such as folic acid antagonists (Methotrexate, Pemetrexed, Raltitrexed, Aminopterin), pyrimidine antagonists (5-Fluorouracil, Floxuridine, Cytarabine, Capecitabine, and Gemcitabine), purine antagonists (6-Mercaptopurine and 6-Thioguanine) and adenosine deaminase inhibitors (Cladribine, Fludarabine, Mercaptopurine, Clofarabine, Thioguanine, Nelarabine and Pentostatin); topoisomerase inhibitors such as topoisomerase I inhibitors (Ironotecan, topotecan) and topoisomerase II inhibitors (Amsacrine, etoposide, etoposide phosphate, teniposide); monoclonal antibodies (Alemtuzumab, Gemtuzumab ozogamicin, Rituximab, Trastuzumab, Ibritumomab Tioxetan, Cetuximab, Panitumumab, Tositumomab, Bevacizumab); and miscellaneous anti-neoplastics such as ribonucleotide reductase inhibitors (Hydroxyurea); adrenocortical steroid inhibitor (Mitotane); enzymes (Asparaginase and Pegaspargase); anti-microtubule agents (Estramustine); and retinoids (Bexarotene, Isotretinoin, Tretinoin (ATRA).

In certain preferred embodiments, the compounds of the invention are administered in combination with a chemoprotective agent. Chemoprotective agents act to protect the body or minimize the side effects of chemotherapy. Examples of such agents include, but are not limited to, amfostine, mesna, and dexrazoxane.

In one aspect of the invention, the subject compounds are administered in combination with radiation therapy. Radiation is commonly delivered internally (implantation of radioactive material near cancer site) or externally from a machine that employs photon (x-ray or gamma-ray) or particle radiation. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

The invention encompasses pharmaceutical compositions comprising pharmaceutically acceptable salts of the compounds of the invention as described above. Preferred salts include hydrochlorates, sulfonates, lower alkylsulfonates (including methylsulfonates), fumarates, maleates, tartrates and citrates. The invention also encompasses pharmaceutical compositions comprising hydrates of the compounds of the invention. The term "hydrate" includes but is not limited to hemihydrate, monohydrate, dihydrate, trihydrate and the like. The invention further encompasses pharmaceutical compositions comprising any solid or liquid physical form of the compound of the invention. For example, the compounds can be in a crystalline form, in amorphous form, and have any particle size. The particles may be micronized, or may be agglomerated, particulate granules, powders, oils, oily suspensions or any other form of solid or liquid physical form.

The compounds of the invention, and derivatives, fragments, analogs, homologs, pharmaceutically acceptable salts or hydrate thereof can be incorporated into pharmaceutical compositions suitable for administration, together with a pharmaceutically acceptable carrier or excipient. Such compositions typically comprise a therapeutically effective amount of any of the compounds above, and a pharmaceutically acceptable carrier. Preferably, the effective amount when treating cancer is an amount effective to selectively induce terminal differentiation of suitable neoplastic cells and less than an amount which causes toxicity in a patient.

It will be appreciated that the compounds of the invention may advantageously be used in conjunction with one or more other therapeutic agents. Examples of suitable agents for adjunctive therapy include a $5HT_1$ agonist, such as a triptan (e.g. sumatriptan or naratriptan); an adenosine A1 agonist; an EP ligand; an NMDA modulator, such as a glycine antagonist; a sodium channel blocker (e.g. lamotrigine); a substance P antagonist (e.g. an $NK_1$ antagonist); a cannabinoid; acetaminophen or phenacetin; a 5-lipoxygenase inhibitor; a leukotriene receptor antagonist; a DMARD (e.g. methotrexate); gabapentin and related compounds; a tricyclic antidepressant (e.g. amitryptilline); a neurone stabilising antiepileptic drug; a mono-aminergic uptake inhibitor (e.g. venlafaxine); a matrix metalloproteinase inhibitor; a nitric oxide synthase (NOS) inhibitor, such as an iNOS or an nNOS inhibitor; an inhibitor of the release, or action, of tumour necrosis factor .alpha.; an antibody therapy, such as a monoclonal antibody therapy; an antiviral agent, such as a nucleoside inhibitor (e.g. lamivudine) or an immune system modulator (e.g. interferon); an opioid analgesic; a local anaesthetic; a stimulant, including caffeine; an $H_2$-antagonist (e.g. ranitidine); a proton pump inhibitor (e.g. omeprazole); an antacid (e.g. aluminum or magnesium hydroxide; an antiflatulent (e.g. simethicone); a decongestant (e.g. phenylephrine, phenylpropanolamine, pseudoephedrine, oxymetazoline, epinephrine, naphazoline, xylometazoline, propylhexedrine, or levo-desoxyephedrine); an antitussive (e.g. codeine, hydrocodone, carmiphen, carbetapentane, or dextramethorphan); a diuretic; or a sedating or non-sedating antihistamine.

In one embodiment, the pharmaceutical compositions are administered orally, and are thus formulated in a form suitable for oral administration, i.e., as a solid or a liquid preparation. Suitable solid oral formulations include tablets, capsules, pills, granules, pellets, sachets and effervescent powders, and the like. Suitable liquid oral formulations include solutions, suspensions, dispersions, emulsions, oils and the like. In one embodiment of the present invention, the composition is formulated in a capsule. In accordance with this embodiment, the compositions of the present invention comprise in addition to the active compound and the inert carrier or diluent, a hard gelatin capsule.

Any inert excipient that is commonly used as a carrier or diluent may be used in the formulations of the present invention, such as for example, a gum, a starch, a sugar, a cellulosic material, an acrylate, or mixtures thereof. A preferred diluent is microcrystalline cellulose. The compositions may further comprise a disintegrating agent (e.g., croscarmellose sodium) and a lubricant (e.g., magnesium stearate), and in addition may comprise one or more additives selected from a binder, a buffer, a protease inhibitor, a surfactant, a solubilizing agent, a plasticizer, an emulsifier, a stabilizing agent, a viscosity increasing agent, a sweetener, a film forming agent, or any combination thereof. Furthermore, the compositions of the present invention may be in the form of controlled release or immediate release formulations.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil. Solutions or suspensions can also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylene diaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide.

In addition, the compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol), a glidant (e.g., colloidal silicon dioxide), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates), cyclodextrins such as alpha- (α), beta- (β) and gamma-(γ) cyclodextrins, preferably beta-cyclodextrins, (e.g., hydroxypropyl beta-cyclodextrins and sulfoalkyl ether beta-cyclodextrins (especially sulfobutyl ether beta-cyclodextrins)) and/or adjuvants.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Daily administration may be repeated continuously for a period of several days to several years. Oral treatment may continue for between one week and the life of the patient. Preferably the administration may take place for five consecutive days after which time the patient can be evaluated to determine if further administration is required. The administration can be continuous or intermittent, e.g., treatment for a number of consecutive days followed by a rest period or on an every-other-day dosing schedule which may be followed by a rest period. The compounds of the present invention may be administered intravenously on the first day of treatment, with oral administration on the second day and all consecutive days thereafter.

The preparation of pharmaceutical compositions that contain an active component is well understood in the art, for example, by mixing, granulating, or tablet-forming processes. The active therapeutic ingredient is often mixed with excipients that are pharmaceutically acceptable and compatible with the active ingredient. For oral administration, the active agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions and the like as detailed above.

The amount of the compound administered to the patient is less than an amount that would cause toxicity in the patient. In certain embodiments, the amount of the compound that is administered to the patient is less than the amount that causes a concentration of the compound in the patient's plasma to equal or exceed the toxic level of the compound. Preferably, the concentration of the compound in the patient's plasma is maintained at about 10 nM. In one embodiment, the concentration of the compound in the patient's plasma is maintained at about 25 nM. In one embodiment, the concentration of the compound in the patient's plasma is maintained at about 50 nM. In one embodiment, the concentration of the compound in the patient's plasma is maintained at about 100 nM. In one embodiment, the concentration of the compound in the patient's plasma is maintained at about 500 nM. In one embodiment, the concentration of the compound in the patient's plasma is maintained at about 1000 nM. In one embodiment, the concentration of the compound in the patient's plasma is maintained at about 2500 nM. In one embodiment, the concentration of the compound in the patient's plasma is maintained at about 5000 nM. The optimal amount of the compound that should be administered to the patient in the practice of the present invention will depend on the particular compound used and the type of cancer being treated.

DEFINITIONS

Listed below are definitions of various terms used to describe this invention. These definitions apply to the terms as they are used throughout this specification and claims, unless otherwise limited in specific instances, either individually or as part of a larger group.

The term "alkyl" embraces linear or branched radicals having one to about eight carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like.

The term "alkenyl" embraces linear or branched radicals having at least one carbon-carbon double bond of two to about eight carbon atoms. Examples of alkenyl radicals include ethenyl, allyl, propenyl, butenyl and 4-methylbutenyl. The terms "alkenyl", and "lower alkenyl", embrace radicals having "cis" and "trans" orientations, or alternatively, "E" and "Z" orientations.

The term "alkynyl" embraces linear or branched radicals having at least one carbon-carbon triple bond of two to about eight carbon atoms. Examples of alkynyl radicals include propargyl, 1-propynyl, 2-propynyl, 1-butyne, 2-butynyl and 1-pentynyl.

The term "cycloalkyl" embraces saturated and unsaturated carbocyclic radicals having three to about eight carbon atoms. Examples of such radicals include cyclopropyl, cyclobutyl, cyclopentyl, cyclohexyl, cyclobutenyl, cyclopentenyl and cyclohexenyl.

The term "substituted" refers to the replacement of one or more hydrogen radicals in a given structure with the radical of a specified substituent including, but not limited to: halo, cyano, nitro, hydroxy, thiol, aliphatic groups (such as alkyl, alkenyl, alkynyl, cycloalkyl, heterocyclyl, alkylthio, arylthio, alkylthioalkyl, arylthioalkyl, alkylamino, alkylaminoalkyl, and aminoalkylamino), and aromatic groups (such as arylamino, arylaminoalkyl, aryl, and heteroaryl). It is understood that the substituent may be further substituted. Preferably, the substituent is not an oxo or acyl group.

For simplicity, chemical moieties are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene."

As used herein, the term "aberrant proliferation" refers to abnormal cell growth.

The phrase "adjunctive therapy" encompasses treatment of a subject with agents that reduce or avoid side effects associated with the combination therapy of the present invention, including, but not limited to, those agents, for example, that reduce the toxic effect of anticancer drugs, e.g., bone resorption inhibitors, cardioprotective agents; prevent or reduce the incidence of nausea and vomiting associated with chemotherapy, radiotherapy or operation; or reduce the incidence of infection associated with the administration of myelosuppressive anticancer drugs.

The term "cancer" as used herein denotes a class of diseases or disorders characterized by uncontrolled division of cells and the ability of these cells to invade other tissues, either by direct growth into adjacent tissue through invasion or by implantation into distant sites by metastasis.

The term "compound" is defined herein to include pharmaceutically acceptable salts, solvates, hydrates, polymorphs, enantiomers, diastereoisomers, racemates and the like of the compounds having a formula as set forth herein.

The term "device" refers to any appliance, usually mechanical or electrical, designed to perform a particular function.

The term "inhibition," in the context of neoplasia, tumor growth or tumor cell growth, may be assessed by delayed appearance of primary or secondary tumors, slowed development of primary or secondary tumors, decreased occurrence of primary or secondary tumors, slowed or decreased severity of secondary effects of disease, arrested tumor growth and regression of tumors, among others. In the extreme, complete inhibition, is referred to herein as prevention or chemoprevention.

The term "metastasis," as used herein, refers to the migration of cancer cells from the original tumor site through the blood and lymph vessels to produce cancers in other tissues. Metastasis also is the term used for a secondary cancer growing at a distant site.

The term "neoplasm," as used herein, refers to an abnormal mass of tissue that results from excessive cell division. Neoplasms may be benign (not cancerous), or malignant (cancerous) and may also be called a tumor. The term "neoplasia" is the pathological process that results in tumor formation.

As used herein, the term "pre-cancerous" refers to a condition that is not malignant, but is likely to become malignant if left untreated.

The term "proliferation" refers to cells undergoing mitosis.

The phrase a "radio therapeutic agent" refers to the use of electromagnetic or particulate radiation in the treatment of neoplasia.

The term "recurrence" as used herein refers to the return of cancer after a period of remission. This may be due to incomplete removal of cells from the initial cancer and may occur locally (the same site of initial cancer), regionally (in vicinity of initial cancer, possibly in the lymph nodes or tissue), and/or distally as a result of metastasis.

The term "treatment" refers to any process, action, application, therapy, or the like, wherein a mammal, including a human being, is subject to medical aid with the object of improving the mammal's condition, directly or indirectly.

As used herein, the term "effective amount of the subject compounds," with respect to the subject method of treatment, refers to an amount of the subject compound which, when delivered as part of desired dose regimen, brings about, e.g. a change in the rate of cell proliferation and/or state of differentiation and/or rate of survival of a cell to clinically acceptable standards. This amount may further relieve to some extent one or more of the symptoms of a neoplasia disorder, including, but is not limited to: 1) reduction in the number of cancer cells; 2) reduction in tumor size; 3) inhibition (i.e., slowing to some extent, preferably stopping) of cancer cell infiltration into peripheral organs; 4) inhibition (i.e., slowing to some extent, preferably stopping) of tumor metastasis; 5) inhibition, to some extent, of tumor growth; 6) relieving or reducing to some extent one or more of the symptoms associated with the disorder; and/or 7) relieving or reducing the side effects associated with the administration of anticancer agents.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical *Sciences*, 66: 1-19 (1977). The salts can be prepared in situ during the final isolation and purification of the compounds of the invention, or separately by reacting the free base function with a suitable organic acid or inorganic acid. Examples of pharmaceutically acceptable nontoxic acid addition salts include, but are not limited to, salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid, lactobionic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, sulfonate and aryl sulfonate.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of the invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38 (1992);

Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

As used herein, "pharmaceutically acceptable carrier" is intended to include any and all solvents, dispersion media, coatings, antibacterial and antifungal agents, isotonic and absorption delaying agents, and the like, compatible with pharmaceutical administration, such as sterile pyrogen-free water. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

As used herein, the term "pre-cancerous" refers to a condition that is not malignant, but is likely to become malignant if left untreated.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds described herein may contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers and/or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; cyclodextrins such as alpha- ($\alpha$), beta- (B) and gamma- ($\gamma$) cyclodextrins; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43650 by Montgomery, all of which are incorporated herein by reference). A discussion of pulmonary delivery of antibiotics is also found in U.S. Pat. No. 6,014,969, incorporated herein by reference.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Synthetic Methods

The compounds of the invention, or a pharmaceutically-acceptable salt thereof, may be prepared by any process known to be applicable to the preparation of chemically-related compounds. Suitable processes for making certain intermediates include, for example, those illustrated in PCT publication numbers WO 2008/115719, WO 2002/36075, WO 2003/037860 and WO 2006/084030. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of a chemist.

The compounds and processes of the present invention will be better understood in connection with the following representative synthetic schemes that illustrate the methods by which the compounds of the invention may be prepared, which are intended as an illustration only and not limiting of the scope of the invention.

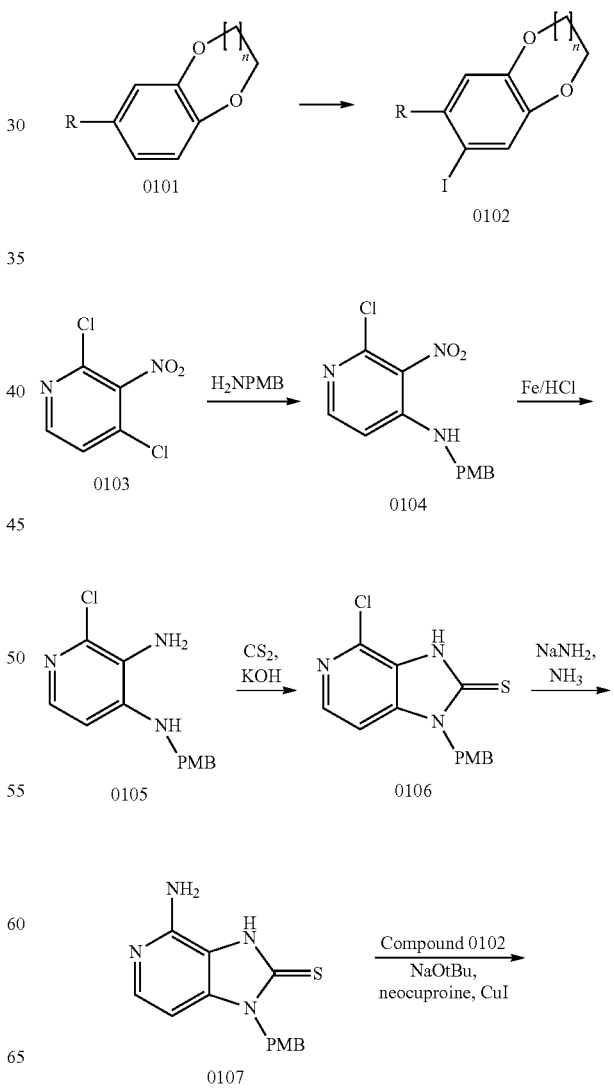

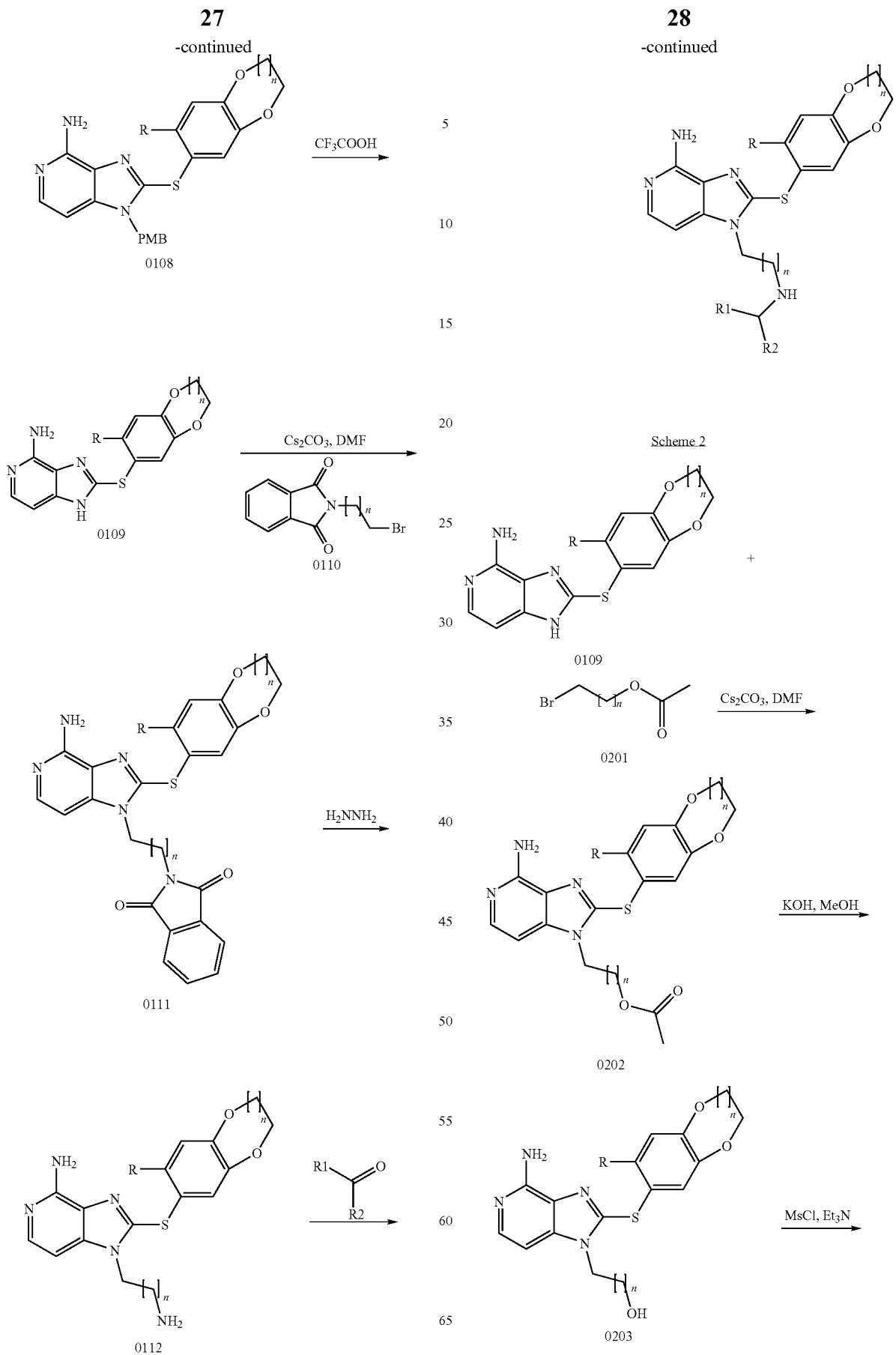

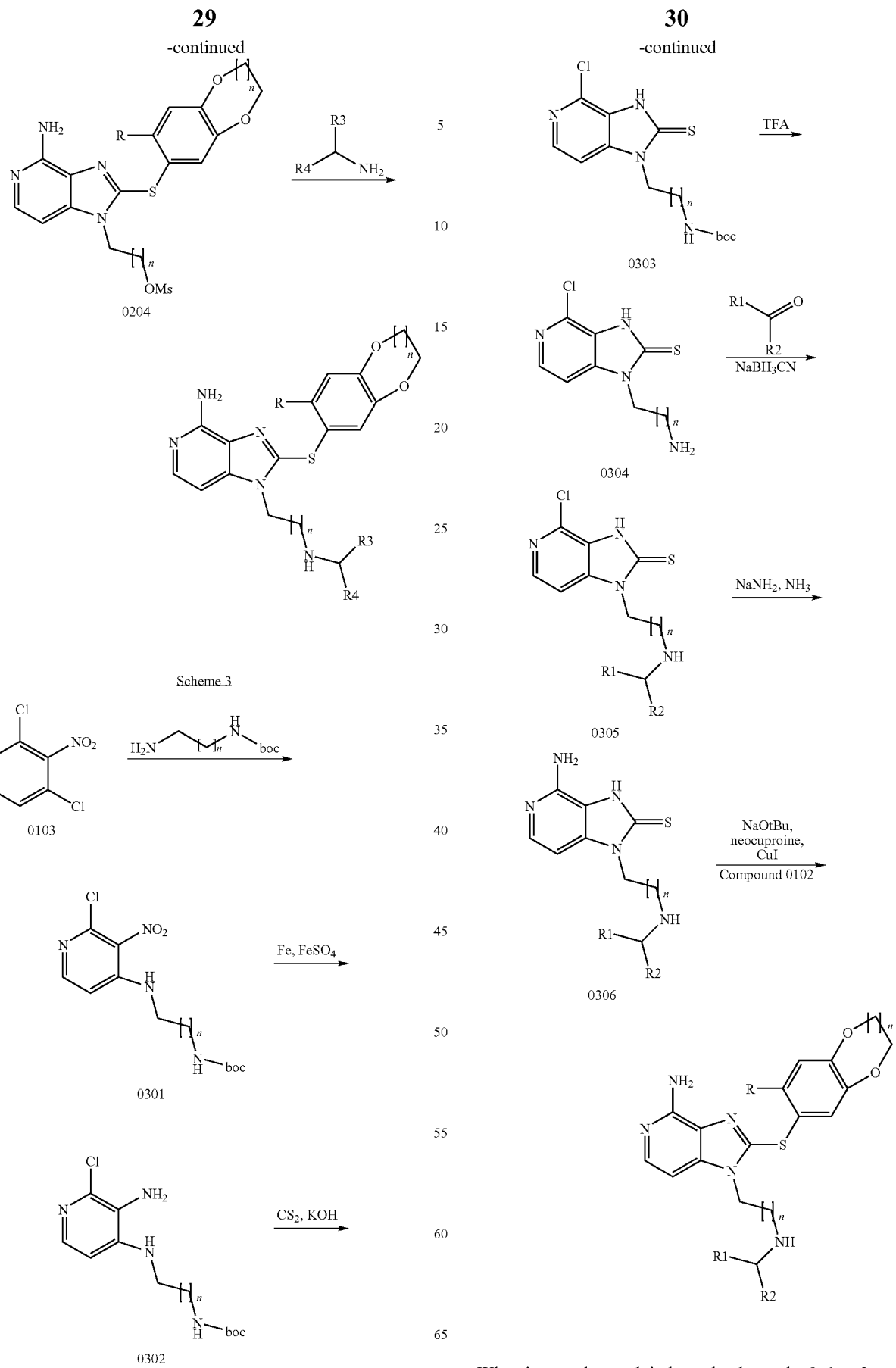
Wherein n, and m each independently can be 0, 1 or 2.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Preparation of 2-(6-bromobenzo[d][1,3]dioxol-5-ylthio)-1-(2-(neopentylamino)ethyl)-1H-imidazo[4,5-c]pyridin-4-amine (Compound 1)

Step 1a. 5-Bromo-6-iodobenzo[d][1,3]dioxole (Compound 0102-1)

A solution of 5-bromobenzo[d][1,3]dioxole (10.0 g, 50.0 mmol), anhydrous acetonitrile (150 mL), TFA (11.4 g, 100.0 mmol) and NIS (33.7 g, 150.0 mmol) was stirred at room temperature for 24 h. The solvent was removed under reduce pressure and the crude purified by column chromatography on silica gel (petroleum) to yield the title compound 0107-1 as a white solid (18.5 g, 91%): $^1$H NMR (DMSO-$d_6$) δ 5.99 (s, 2H), 7.10 (s, 1H), 7.26 (s, 1H).

Step 1b. 2-Chloro-N-(4-methoxybenzyl)-3-nitropyridin-4-amine (Compound 0104)

To a solution of 2,4-dichloro-3-nitropyridine (0103) (1 g, 5.18 mmol) in DMF (8.6 mL) was added (4-methoxyphenyl)methanamine (0.71 g, 5.18 mmol) and triethylamine (0.644 mL). The solution was stirred at room temperature for 2 h. The mixture was evaporated to remove DMF. The resulting mixture was purified by column chromatography on silica gel (EtOAc/petroleum at 10:1) to obtain the title compound 0104 as a yellow solid (1.32 g, 87%): LCMS: 294 [M+1]$^+$; $^1$H NMR (DMSO-$d_6$) δ 3.72 (s, 3H), 4.40 (d, 2H, J=6.3 Hz), 6.81 (d, 1H, J=5.7 Hz), 6.91 (d, 2H, J=9.0 Hz), 7.25 (d, 2H, J=8.4 Hz), 7.95 (d, 1H, J=5.4 Hz), 8.02 (t, 1H, J=5.7 Hz).

Step 1c. 2-Chloro-N$^4$-(4-methoxybenzyl)pyridine-3,4-diamine (Compound 0105)

To a mixture of compound 0104 (1.32 g, 4.49 mmol) in methanol (66 mL) and water (6.6 mL) was added iron powder (2.51 g, 44.9 mmol) and concentrated HCl solution (1 mL). The mixture was stirred at room temperature for 30 min, and then at reflux overnight. The mixture was adjusted to pH 11 with 6N NaOH and filtered. The precipitate was washed with methanol (10 mL). The combined filtrate and wash solution was concentrated and purified by column chromatography on silica gel (EtOAc/petroleum at 2:1) to obtain the title compound 0105 as a light green solid (712 mg, 60%): LCMS: 264 [M+1]$^+$; $^1$H NMR (DMSO-$d_6$) δ 3.73 (s, 3H), 4.31 (d, 2H, J=5.7 Hz), 4.81 (s, 2H), 6.33 (m, 2H), 6.90 (d, 2H, J=8.7 Hz), 7.26 (d, 2H, J=9.0 Hz), 7.34 (d, 1H, J=5.1 Hz).

Step 1d. 4-Chloro-1-(4-methoxybenzyl)-1H-imidazo[4,5-c]pyridine-2(3H)-thione (Compound 0106)

A mixture of 0105 (2 g, 7.6 mmol), carbon disulfide (2.88 g, 37.9 mmol), potassium hydroxide (2.12 g, 37.9 mmol) in ethanol (11.5 mL) and water (1.5 mL) was heated at reflux overnight. Water (100 mL) was added after the mixture was allowed to cool down to room temperature. The mixture was adjusted to pH 7 with acetic acid and then extracted with two portions of methylene chloride. The organic layer was collected and concentrated at reduced pressure to leave an residue which was purified by column chromatography on silica gel (EtOAc/petroleum at 5:1) to obtain the title compound 0106 as a white solid (2 g, 86%): LCMS: 306 [M]$^+$; $^1$H NMR (DMSO-$d_6$) δ 3.68 (s, 3H), 6.41 (s, 2H), 6.86 (d, 2H, J=8.7 Hz), 7.36 (m, 3H), 8.07 (d, 1H, J=5.4 Hz), 13.74 (s, 1H).

Step 1e. 4-Amino-1-(4-methoxybenzyl)-1H-imidazo[4,5-c]pyridine-2(3H)-thione (Compound 0107)

A mixture of 0106 (1 g, 3.25 mmol) and sodium amide (3 g, 77 mmol) in 25 mL liquid ammonia was charged in an air free sealed tube. The mixture was then stirred at room temperature for 30 h. The mixture was cooled to ±40° C. and then tube was opened. Ethanol was added carefully to terminate the reaction until no gas generated. Water (200 mL) was added and the mixture was adjusted to pH 7 with acetic acid. The resulting solid was filtered to obtain crude product which was purified by column chromatography on silica gel (methylene chloride/methanol at 50:1) to obtain the title compound 0107 as a white solid (718 mg, 77%): LCMS: 287 [M]$^+$; $^1$H NMR (DMSO-$d_6$) δ 3.68 (s, 3H), 5.31 (s, 2H), 6.06 (s, 2H), 6.59 (d, 1H, J=6.3 Hz), 6.85 (d, 2H, J=9.0 Hz), 7.33 (d, 2H, J=8.4 Hz), 7.64 (d, 1H, J=5.7 Hz), 12.53 (s, 1H).

Step 1f. 2-(6-Bromobenzo[d][1,3]dioxol-5-ylthio)-1-(4-methoxybenzyl)-1H-imidazo[4,5-c]pyridin-4-amine (Compound 0108-1)

A mixture of 0107 (700 mg, 2.44 mmol), 5-bromo-6-iodobenzo[d][1,3]dioxole (1.20 g, 3.66 mmol), neocuproine hydrate (51 mg, 0.244 mmol), CuI (46 mg, 0.244 mmol) and NaOt-Bu (234 mg, 2.44 mmol) in anhydrous DMF (31 mL) was stirred for 24 h at 110° C. (oil bath) under nitrogen atmosphere. The solvent was removed under high vacuum and the crude purified by column chromatography on silica gel (CH$_2$Cl$_2$/MeOH at 100/1) to obtain the title compound 0108-1 as a brown solid (584 mg, 49%): LCMS: 485 [M+1]$^+$; $^1$H NMR (DMSO-$d_6$) δ 3.69 (s, 3H), 5.35 (s, 2H), 6.04 (s, 2H), 6.54 (s, 1H), 6.81 (m, 4H), 7.06 (d, 2H, J=8.7 Hz), 7.29 (s, 1H).

Step 1g. 2-(6-Bromobenzo[d][1,3]dioxol-5-ylthio)-1H-imidazo[4,5-c]pyridin-4-amine (Compound 0109-1)

A solution of compound 0108-1 (557 mg, 1.15 mmol) and TFA (4 mL) was stirred for 2 h at 80° C. The TFA was then evaporated and the resulting oil was adjusted to pH 7 with saturated NaHCO$_3$. The resulting precipitate was collected by filtration and further purified by column chromatography on silica gel (CH$_2$Cl$_2$/MeOH at 30/1) to give the title compound 0109-1 as a yellow solid (308 mg, 74%): LCMS: 365 [M+1]$^+$; $^1$H NMR (DMSO-$d_6$) δ 6.07 (s, 2H), 6.58 (s, 2H), 6.69 (d, 1H, J=6.0 Hz), 6.98 (s, 1H), 7.34 (s, 1H), 7.47 (d, 1H, J=6.0 Hz).

Step 1h. 2-(2-(4-Amino-2-(6-bromobenzo[d][1,3]dioxol-5-ylthio)-1H-imidazo[4,5-c]pyridin-1-yl)ethyl)isoindoline-1,3-dione (Compound 0111-1)

A mixture of 0109-1 (975 mg, 2.67 mmol), 2-(2-bromoethyl)isoindoline-1,3-dione (1.017 g, 4.00 mmol), Cs$_2$CO$_3$ (1.475 g, 4.54 mmol) in anhydrous DMF (38 mL) was stirred at 50° C. for 4 h. The reaction mixture was cooled to room temperature and filtered. The filtrate was evaporated under high vacuum to give a crude product as an orange solid which was purified by column chromatography on silica gel (CH$_2$Cl$_2$/MeOH=100/1) to provide the title compound 0302-32 as a pale yellow solid (720 mg, 50%): LCMS: 538 [M+1]$^+$.

Step 1i. 1-(2-Aminoethyl)-2-(6-bromobenzo[d][1,3] dioxol-5-ylthio)-1H-imidazo[4,5-c]pyridin-4-amine (Compound 0112-1)

A mixture of compound 0111-1 (720 mg, 1.337 mmol) and N$_2$H$_4$—H$_2$O (886 mg, 14.71 mmol) in CH$_2$Cl$_2$ (27 mL) and EtOH (3 mL) was stirred at 50° C. for 2 h. The solid was removed by filtration and the filtrate was washed with brine (100 mL×2), dried over Na$_2$SO$_4$, filtered and evaporated to give the title compound 0112-1 as a pale yellow solid (495 mg, 91%): LCMS: 408 [M+1]$^+$.

Step 1j. 2-(6-Bromobenzo[d][1,3]dioxol-5-ylthio)-1-(2-(neopentylamino)ethyl)-1H-imidazo[4,5-c]pyridin-4-amine (Compound 1)

To a solution of compound 0112-1 (150 mg, 0.613 mmol) in methanol (10 mL) was added pivalaldehyde (63 mg, 0.736 mmol). After the mixture was stirred for 30 min at room temperature, NaBH$_3$CN (154 mg, 2.452 mmol) was added slowly, and the mixture was stirred for additional 30 min. The reaction was terminated by adding saturated NaHCO$_3$ (10 mL) and the resulting mixture was diluted with water (100 mL) and extracted with dichloromethane (50×2). The combined organic layer was concentrated to leave a residue which was purified by pre-HPLC to give the title compound 1 as a white solid (60 mg, 20%): m.p. 181~187° C. LCMS: 478 [M+1]$^+$; $^1$H NMR (DMSO-d$_6$) δ 0.76 (s, 9H), 1.61 (s, 1H), 2.18 (s, 2H), 2.76 (t, 2H, J=6.3 Hz), 4.24 (t, 2H, J=6.3 Hz), 6.06 (s, 2H), 6.31 (s, 2H), 6.62 (s, 1H), 6.83 (d, 1H, J=5.7 Hz), 7.34 (s, 1H), 7.70 (d, 1H, J=5.7 Hz).

Example 2

Preparation of 2-(6-iodobenzo[d][1,3]dioxol-5-ylthio)-1-(2-(neopentylamino)ethyl)-1H-imidazo[4,5-c]pyridin-4-amine (Compound 2)

Step 2a. 5,6-Diiodobenzo[d][1,3]dioxole (Compound 0102-2)

A solution of 5,6-diiodobenzo[d][1,3]dioxole (1.0 g, 8.19 mmol), acetonitrile (51 mL), TFA (1.867 g) and NIS (4.05 g, 18.02 mmol) was stirred at room temperature for 24 h. The solvent was removed under high vacuum and the crude product purified by column chromatography on silica gel (petroleum) to yield the title compound 0102-2 as a white solid (1.48 g, 48%): $^1$H NMR (DMSO-d$_6$) δ 6.05 (s, 2H), 7.46 (s, 2H).

Step 2b. 2-(6-Iodobenzo[d][1,3]dioxol-5-ylthio)-1-(4-methoxybenzyl)-1H-imidazo[4,5-c]pyridin-4-amine (Compound 0108-2)

A mixture of 0107 (725 mg, 2.53 mmol), 5,6-Diiodobenzo[d][1,3]dioxole (0102-2) (1.89 g, 5.06 mmol), neocuproine hydrate (53 mg, 0.253 mmol), CuI (48 mg, 0.253 mmol) and NaOt-Bu (365 mg, 3.80 mmol) in anhydrous DMF (32 mL) was stirred for 24 h at 110° C. (oil bath) under nitrogen atmosphere. The solvent was removed under high vacuum and the crude purified by column chromatography on silica gel (CH$_2$Cl$_2$/MeOH at 100/1) to obtain the title compound 0108-2 as a brown solid (734 mg, 55%): LCMS: 533 [M+1]$^+$; $^1$H NMR (DMSO-d$_6$) δ 3.69 (s, 3H), 5.35 (s, 2H), 6.01 (s, 2H), 6.47 (s, 1H), 6.80 (d, 2H, J=9.0 Hz), 7.06 (d, 2H, J=8.7 Hz), 7.41 (s, 1H).

Step 2c. 2-(6-Iodobenzo[d][1,3]dioxol-5-ylthio)-1H-imidazo[4,5-c]pyridin-4-amine (Compound 0109-2)

A solution of compound 0108-2 (730 mg, 1.37 mmol) in TFA (4.8 mL) was stirred for 2 h at 80° C. The TFA was then evaporated and the resulting oil was adjusted to pH 7 with saturated NaHCO$_3$. The resulting precipitate was collected by filtration and further purified by column chromatography on silica gel (CH$_2$Cl$_2$/MeOH at 30/1) to give the title compound 00109-2 as a yellow solid (526 mg, 93%): LCMS: 413 [M+1]$^+$; $^1$H NMR (DMSO-d$_6$) δ 6.09 (s, 2H), 6.73 (m, 3H), 7.03 (s, 1H), 7.52 (m, 2H), 12.45 (s, 1H).

Step 2d. 2-(2-(4-Amino-2-(6-iodobenzo[d][1,3]dioxol-5-ylthio)-1H-imidazo[4,5-c]pyridin-1-yl)ethyl)isoindoline-1,3-dione (Compound 0111-2)

A mixture of compound 0109-2 (500 mg, 1.2 mmol), 2-(2-bromoethyl)isoindoline-1,3-dione (0301) (457 mg, 1.8 mmol) and Cs$_2$CO$_3$ (672 mg, 2.1 mmol) in anhydrous DMF (8 mL) was stirred at 50° C. for 4 h. The reaction mixture was cooled to room temperature and filtered. The filtrate was evaporated under high vacuum to give a crude product as an orange solid which was purified by column chromatography on silica gel (CH$_2$Cl$_2$/MeOH=100/1) to provide the title compound 0111-2 as a pale yellow solid (390 mg, 56%): LC-MS: 586 [M+1]$^+$. $^1$H NMR (300 MHz, DMSO-d$_6$) δ 3.92 (t, 2H, J=5.3 Hz), 4.50 (t, 2H, J=5.3 Hz), 6.00 (s, 2H), 6.38 (s, 2H), 6.49 (s, 1H), 6.75 (d, 1H, J=6.0 Hz), 7.19 (s, 1H), 7.64 (d, 1H, J=6.0 Hz), 7.73 (m, 4H).

Step 2e. 1-(2-Aminoethyl)-2-(6-iodobenzo[d][1,3]dioxol-5-ylthio)-1H-imidazo[4,5-c]pyridin-4-amine (Compound 0112-2)

A mixture of compound 0111-2 (5 g, 8.55 mmol) and N$_2$H$_4$—H$_2$O (4.28 g, 85.5 mmol) in CH$_2$Cl$_2$ (150 mL) and EtOH (15 mL) was stirred at 50° C. for 2 h. The solid was removed by filtration and the filtrate was washed with brine (100 mL×2), dried over Na$_2$SO$_4$, filtered and evaporated to give compound 32 as a white solid (3 g, 77%): m. p. 111~121° C. LC-MS: 456 [M+1]$^+$. $^1$H NMR (300 MHz, DMSO-d$_6$) δ 1.46 (s, 2H) 2.80 (t, 2H, J=6.3 Hz), 4.16 (t, 2H, J=6.6 Hz), 6.05 (s, 2H), 6.29 (s, 2H), 6.69 (s, 1H), 6.84 (d, 1H, J=6.0 Hz), 7.46 (s, 1H), 7.70 (d, 1H, J=5.7 Hz).

Step 2f. 2-(6-iodobenzo[d][1,3]dioxol-5-ylthio)-1-(2-(neopentylamino)ethyl)-1H-imidazo[4,5-c]pyridin-4-amine The title compound 2 was prepared as a white solid (2.718 g, 26%) from compound 0112-2 (9.1 g, 19.9 mmol), pivalaldehyde (2.06 g, 24 mmol) and NaBH$_3$CN (5.027 g, 80 mmol) using a procedure similar to that described for compound 1 (Example 1): m.p. 203~207° C. LCMS: 526 [M+1]$^+$; $^1$H NMR (DMSO-d$_6$) δ 0.77 (s, 9H), 1.60 (s, 1H), 2.18 (s, 2H), 2.75 (t, 2H, J=5.7 Hz), 4.23 (t, 2H, J=5.4 Hz), 6.04 (s, 2H), 6.33 (s, 2H), 6.58 (s, 1H), 6.83 (d, 1H, J=6.0 Hz), 7.46 (s, 1H), 7.77 (d, 1H, J=5.7 Hz).

Example 3

Preparation of 2-(7-iodo-2,3-dihydrobenzo[b][1,4]dioxin-6-ylthio)-1-(2-(neopentylamino)ethyl)-1H-imidazo[4,5-c]pyridin-4-amine (Compound 5)

Step 3a. 6,7-Diiodo-2,3-dihydrobenzo[b][1,4]dioxine (Compound 0102-5)

To a solution of 6-iodo-2,3-dihydrobenzo[b][1,4]dioxine (2 g, 14.7 mmol) in acetonitrile (60 ml) was added NIS (9.92 g, 44.1 mmol) followed by $CF_3COOH$ (3.35 g, 29.4 mmol). The mixture was stirred at room temperature overnight. The reaction mixture was concentrated and purified by column chromatography on silica gel (Petroleum ether) to provide the title compound 0102-5 as a white solid (0.7 g, 12%): $^1H$ NMR (DMSO-$d_6$) δ 4.21 (s, 4H), 7.34 (s, 2H).

Step 3b. 2-(7-Iodo-2,3-dihydrobenzo[b][1,4]dioxin-6-ylthio)-1-(4-methoxybenzyl)-1H-imidazo[4,5-c]pyridin-4-amine (Compound 0108-5)

A mixture of compound 0107 (3 g, 10.5 mmol), 6,7-Diiodo-2,3-dihydrobenzo[b][1,4]dioxine (0102-5) (8.1 g, 21 mmol), neocuproine hydrate (0.2 g, 1.05 mmol), CuI (0.2 g, 1.05 mmol) and NaOt-Bu (1.5 g, 15.7 mmol) in dry DMF (100 mL) was stirred at 110° C. overnight. The mixture was concentrated and purified by column chromatography on silica gel ($CH_2Cl_2$/MeOH=100/1) to give the title compound 0108-5 as a brown solid (2.2 g, 38%): LCMS: 547 [M+1]$^+$; $^1H$ NMR (DMSO-$d_6$) δ 3.69 (s, 3H), 4.19 (m, 4H), 5.49 (s, 2H), 6.68 (s, 1H), 6.83 (d, 2H, J=8.4 Hz), 7.11 (d, 2H, J=8.7 Hz), 7.28 (d, 1H, J=7.2 Hz), 7.35 (s, 1H), 7.71 (d, 1H, J=7.2 Hz), 8.42 (s, 2H), 13.36 (s, 1H).

Step 3c. 2-(7-Iodo-2,3-dihydrobenzo[b][1,4]dioxin-6-ylthio)-1H-imidazo[4,5-c]pyridin-4-amine (Compound 0109-5)

A mixture of compound 0108-5 (2.2 g, 4 mmol), trifluoroacetic acid (20 mL) was stirred at reflux for 2 h. The solvent was removed and the residue was suspended in saturated aqueous $NaHCO_3$ solution. The resulting solid was collected and dried to give the title compound 0206-37 as a white solid (1.5 g, 88%): LCMS: 427 [M+1]$^+$; $^1H$ NMR (DMSO-$d_6$) δ 4.29 (m, 4H), 6.96 (d, 1H, J=6.9 Hz), 7.20 (s, 1H), 7.50 (s, 1H), 7.63 (d, 1H, J=6.9 Hz), 8.42 (s, 2H), 13.36 (s, 1H).

Step 3d. 2-(2-(4-Amino-2-(7-iodo-2,3-dihydrobenzo[b][1,4]dioxin-6-ylthio)-1H-imidazo[4,5-c]pyridin-1-yl)ethyl)isoindoline-1,3-dione (Compound 0111-5)

A mixture of compound 0109-5 (1.5 g, 3.5 mmol), 2-(2-bromoethyl)isoindoline-1,3-dione (1.34 g, 5.3 mmol) and $Cs_2CO_3$ (1.94 g, 6.0 mmol) in anhydrous DMF (50 mL) was stirred at 50° C. for 4 h. The reaction mixture was cooled to room temperature and filtered. The filtrate was evaporated under high vacuum to give a crude product as an orange solid which was purified by column chromatography on silica gel ($CH_2Cl_2$/MeOH=100/1) to provide the title compound 0111-5 as a white solid (1.2 g, 57%): LCMS: 600 [M+1]$^+$; $^1H$ NMR (DMSO-$d_6$) δ 3.92 (t, 2H, J=5.7 Hz), 4.16 (m, 4H), 4.48 (t, 2H, J=4.8 Hz), 6.38 (s, 2H), 6.41 (s, 1H), 6.75 (d, 1H, J=6 Hz), 7.15 (s, 1H), 7.64 (d, 1H, J=5.7 Hz), 7.77 (m, 4H).

Step 3e. 1-(2-Aminoethyl)-2-(7-iodo-2,3-dihydrobenzo[b][1,4]dioxin-6-ylthio)-1H-imidazo[4,5-c]pyridin-4-amine (Compound 0112-5)

A mixture of compound 0111-5 (5 g, 8.55 mmol) and $N_2H_4$—$H_2O$ (1 g, 20 mmol) in $CH_2Cl_2$ (28 mL) and EtOH (3 mL) was stirred at 50° C. for 2 h. The solid was removed by filtration and the filtrate was washed with brine (100 mL×2), dried over $Na_2SO_4$, filtered and evaporated to give the compound 0112-5 as a yellow solid (790 mg, 84%): LC-MS: 470 [M+1]$^+$. $^1H$ NMR (300 MHz, DMSO-$d_6$) δ 1.51 (m, 2H), 2.77 (t, 2H, J=6.6 Hz), 4.16 (m, 6H), 6.27 (s, 2H), 6.53 (s, 1H), 6.81 (d, 1H, J=6 Hz), 7.35 (s, 1H), 7.67 (d, 1H, J=5.7 Hz).

Step 3f. 2-(7-Iodo-2,3-dihydrobenzo[b][1,4]dioxin-6-ylthio)-1-(2-(neopentylamino)ethyl)-1H-imidazo[4,5-c]pyridin-4-amine (Compound 5)

The title compound 5 was prepared as a white solid (128 mg, 14%) from compound 0112-5 (790 mg, 1.7 mmol), pivalaldehyde (217 mg, 2.5 mmol) and $NaBH_3CN$ (423 mg, 6.7 mmol) using a procedure similar to that described for compound 1 (Example 1): m.p. 193~200° C. LCMS: 540 [M+1]$^+$; $^1H$ NMR (DMSO-$d_6$) δ 0.793 (s, 9H), 2.32 (s, 2H), 2.88 (t, 2H, J=6.3 Hz), 4.18 (m, 4H), 4.32 (t, 2H, J=6.6 Hz), 6.50 (s, 1H), 6.76 (s, 2H), 6.94 (d, 1H, J=6 Hz), 7.37 (s, 1H), 7.73 (d, 1H, J=6.3 Hz).

Example 4

Preparation of 1-(2-(tert-butylamino)ethyl)-2-(6-iodobenzo[d][1,3]dioxol-5-ylthio)-1H-imidazo[4,5-c]pyridin-4-amine (Compound 8)

Step 4a. 2-(4-Amino-2-(6-iodobenzo[d][1,3]dioxol-5-ylthio)-1H-imidazo[4,5-c]pyridin-1-yl)ethyl acetate (Compound 0202-8)

A mixture of compound 0109-2 (300 mg, 0.728 mmol), 2-bromoethyl acetate (182 mg, 1.092 mmol) and $Cs_2CO_3$ (402 mg, 1.24 mmol) in DMF (10 mL) was stirred at 85° C. for 2 h. DMF was evaporated under vacuum and the residue was purified by column chromatography on silica gel (methylene chloride/methanol at 100:1) to yield the title compound 0202-8 as a white solid (188 mg, 50.4%): LCMS: 499 [M+1]$^+$; $^1H$ NMR (DMSO-$d_6$) δ 1.86 (s, 3H), 4.26 (t, 2H, J=4.8 Hz), 4.45 (t, 2H, J=4.8 Hz), 6.03 (s, 2H), 6.35 (s, 2H), 6.68 (s, 1H), 6.81 (d, 1H, J=6.0 Hz), 7.76 (s, 1H), 7.71 (d, 1H, J=6.0 Hz).

Step 4b. 2-(4-Amino-2-(6-iodobenzo[d][1,3]dioxol-5-ylthio)-1H-imidazo[4,5-c]pyridin-1-yl)ethanol (Compound 0203-8)

A suspension of compound 0202-8 (180 mg, 0.36 mmol) in MeOH (3 mL) was treated with $K_2CO_3$ (60 mg, 0.43 mmol) at 50° C. for 1 h. The mixture was diluted with water (15 mL) and filtered to provide the title compound 0203-8 as a white solid (150 mg, 91%): LCMS: 457 [M+1]$^+$; $^1H$ NMR (DMSO-$d_6$) δ 3.63 (m, 2H), 4.27 (t, 2H, J=5.4 Hz), 4.98 (t, 2H, J=5.7 Hz), 6.05 (s, 2H), 6.31 (s, 2H), 6.69 (s, 1H), 6.80 (d, 1H, J=6.0 Hz), 7.46 (s, 1H), 7.69 (d, 1H, J=5.7 Hz).

Step 4c. 2-(4-Amino-2-(6-iodobenzo[d][1,3]dioxol-5-ylthio)-1H-imidazo[4,5-c]pyridin-1-yl)ethyl methanesulfonate (Compound 0204-8)

Compound 0203-8 (133 mg, 0.292 mmol) was dissolved in hot anhydrous dioxane (4 mL). The solution was cooled to 40° C. and was then treated with NEt₃ (89 mg, 0.876 mmol) and MsCl (50 mg, 0.438 mmol) for 20 min. The mixture was concentrated and purified by column chromatography on silica gel (CH$_2$Cl$_2$/MeOH=50/1) to provide the title compound 0204-8 as a white solid (122 g, 78.3%): LCMS: 535 [M+1]$^+$; $^1$H NMR (DMSO-d$_6$) δ 3.07 (s, 3H), 4.46 (t, 2H, J=4.5 Hz), 4.59 (t, 2H, J=5.1 Hz), 6.05 (s, 2H), 6.59 (s, 2H), 6.71 (s, 1H), 6.90 (d, 1H, J=6.0 Hz), 7.48 (s, 1H), 7.73 (d, 1H, J=6.6 Hz).

Step 4d. 1-(2-(tert-butylamino)ethyl)-2-(6-iodobenzo[d][1,3]dioxol-5-ylthio)-1H-imidazo[4,5-c]pyridin-4-amine (Compound 8)

A solution of compound 0204-8 (250 mg, 0.47 mmol) in tert-butylamine (30 mL) was stirred at 60° C. for 24 h in a pressure vessel. The solvent was removed and the crude was purified by column chromatography on silica gel (CH$_2$Cl$_2$/MeOH=50/1) and followed by pre-HPLC to provide the title compound 8 as a white solid (34 mg, 15%): m.p. 194~197° C. LCMS: 512 [M+1]$^+$; $^1$H NMR (DMSO-d$_6$) δ 0.88 (s, 9H), 1.60 (s, 1H), 2.70 (t, J=6.0 Hz, 2H), 4.20 (t, J=6.0 Hz, 2H), 6.05 (s, 2H), 6.35 (s, 2H), 6.70 (s, 1H), 6.83 (d, J=6.0 Hz, 1H), 7.48 (s, 1H), 7.72 (d, J=6.0 Hz, 1H).

Example 5

Preparation of 2-(6-iodobenzo[d][1,3]dioxol-5-ylthio)-1-(2-(isopropylamino)ethyl)-1H-imidazo[4,5-c]pyridin-4-amine (Compound 9)

The title compound 9 was prepared as a white solid (40 mg, 17%) from compound 0204-8 (252 mg, 0.47 mmol) in isopropylamine (30 mL) using a procedure similar to that described for compound 8 (Example 4): m.p. 170~172° C. LCMS: 498 [M+1]$^+$; $^1$H NMR (DMSO-d$_6$) δ 0.86 (d, J=6.3 Hz, 6H), 1.68 (s, 1H), 2.62 (m, 1H), 2.74 (t, J=6.6 Hz, 2H), 4.21 (t, J=6.6 Hz, 2H), 6.04 (s, 2H), 6.36 (s, 2H), 6.67 (s, 1H), 6.82 (d, J=6.0 Hz, 1H), 7.47 (s, 1H), 7.71 (d, J=6.0 Hz, 1H).

Example 6

Preparation of 2-(6-iodobenzo[d][1,3]dioxol-5-ylthio)-1-(3-(neopentylamino)propyl)-1H-imidazo[4,5-c]pyridin-4-amine (Compound 11)

Step 6a. 2-(3-(4-Amino-2-(6-iodobenzo[d][1,3]dioxol-5-ylthio)-1H-imidazo[4,5-c]pyridin-1-yl)propyl)isoindoline-1,3-dione (Compound 0111-11)

The title compound 0111-11 was prepared as a pale yellow solid (410 mg, 57%) from compound 2-(6-Iodobenzo[d][1,3]dioxol-5-ylthio)-1H-imidazo[4,5-c]pyridin-4-amine (Compound 0109-2) (500 mg, 1.2 mmol), 2-(3-bromopropyl)isoindoline-1,3-dione (610 mg, 2.4 mmol) and Cs$_2$CO$_3$ (652 mg, 2.0 mmol) in anhydrous DMF (8.5 mL) using a procedure similar to that described for compound 0111-2 (Example 2): LC-MS: 599.7 [M+1]$^+$; $^1$H NMR (DMSO-d$_6$): δ 1.93 (m, 2H), 3.61 (t, J=6.6 Hz, 2H), 4.21 (t, J=8.1 Hz, 2H), 6.04 (s, 2H), 6.40 (s, 2H), 6.50 (s, 1H), 6.87 (d, J=6.0 Hz, 1H), 7.21 (s, 1H), 7.70 (d, J=6.0 Hz, 1H), 7.85 (s, 4H).

Step 6b. 1-(3-Aminopropyl)-2-(6-iodobenzo[d][1,3]dioxol-5-ylthio)-1H-imidazo[4,5-c]pyridin-4-amine (Compound 0112-11)

The title compound 0112-11 was prepared as a pale yellow solid (200 mg, 74%) from compound 0111-11 (350 mg, 0.58 mmol) and N$_2$H$_4$—H$_2$O (580 mg, 11.6 mmol) in CH$_2$Cl$_2$ (7.0 mL) and EtOH (0.6 mL) using a procedure similar to that described for compound 0112-2 (Example 2): LC-MS: 469.7 [M+1]$^+$.

Step 6c. 2-(6-Iodobenzo[d][1,3]dioxol-5-ylthio)-1-(3-(neopentylamino)propyl)-1H-imidazo[4,5-c]pyridin-4-amine (Compound 11)

The title compound 11 was prepared as a white solid (110 mg, 37%) from compound 0112-11 (257 mg, 0.55 mmol) and pivalaldehyde (60 mg, 0.70 mmol). Using a procedure similar to that described for compound 1 (Example 1): m.p. 170~174° C. LCMS: 540 [M+1]$^+$; $^1$H NMR (DMSO-d$_6$): δ 0.84 (s, 9H), 1.76 (m, 2H), 2.14 (s, 2H), 2.43 (t, J=6.9 Hz, 2H), 4.23 (t, J=7.2 Hz, 2H), 6.04 (s, 2H), 6.36 (s, 2H), 6.63 (s, 1H), 6.80 (d, J=6.0 Hz, 1H), 7.47 (s, 1H), 7.71 (d, J=6.0 Hz, 1H).

Example 7

Preparation of 2-(6-(dimethylamino)benzo[d][1,3]dioxol-5-ylthio)-1-(2-(neopentylamino)ethyl)-1H-imidazo[4,5-c]pyridin-4-amine (Compound 15)

Step 7a.
6-Iodo-N,N-dimethylbenzo[d][1,3]dioxol-5-amine (Compound 0102-15)

To a solution of 3,4-(Methylenedioxy)aniline (8 g, 58.3 mmol) in AcOH (120 ml) was added Ac2O (48 mL). The mixture was stirred for overnight. After reaction, the mixture was poured into saturated NaHCO$_3$ solution, and then filtered. The filtrate was extracted with ethyl acetate to give N-(benzo[d][1,3]dioxol-5-yl)acetamide (10 g, 95%). LCMS: 180 [M+1]$^+$; $^1$H NMR (DMSO-d$^6$) δ 2.0 (s, 3H), 5.96 (s, 2H), 6.82 (d, 1H, J=8.1 Hz), 6.91 (d, 1H, J=2.1 Hz), 7.30 (d, 1H, J=1.8 Hz), 9.84 (s, 1H).

A 1.0 M solution of iodine monochloride in methylene chloride (72.6 mL) was added dropwise to a solution of N-(benzo[d][1,3]dioxol-5-yl)acetamide (10 g, 55.8 mmol) in methylene chloride (66 mL) and acetic acid (11 mL). The mixture was stirred under nitrogen overnight and then washed with saturated sodium thiosulfate (2×150 mL) and brine (150 mL). The methylene chloride solution was dried (MgSO$_4$) and evaporated, and the residue was purified by column chromatography on silica gel (CH$_2$Cl$_2$/petroleum at 20/1) to obtain N-(6-iodobenzo[d][1,3]dioxol-5-yl)acetamide (3.7 g, 22%) as a white solid. LCMS: 306 [M+1]$^+$; $^1$H NMR (DMSO-d$^6$) δ 2.00 (s, 3H), 6.06 (s, 2H), 6.95 (s, 1H), 7.37 (s, 1H), 9.34 (s, 1H).

A solution of N-(6-iodobenzo[d][1,3]dioxol-5-yl)acetamide (200 mg, 0.656 mmol) and NaOH (1.31 g, 32.8 mmol) in ethanol (26 mL) and water (6 mL) was heated to reflux with stirring for 4 h. The mixture was cooled and the solvent was removed under vacuum. The residue was partitioned between methylene chloride (100 mL) and water (100 mL). The organic layer was washed with water (2×100 mL), dried (MgSO$_4$) and evaporated under vacuum to give 6-iodobenzo[d][1,3]dioxol-5-amine (170 mg, 98%) as orange solid. LCMS: 264 [M+1]$^+$; $^1$H NMR (DMSO-d$^6$) δ 4.88 (s, 2H), 5.87 (s, 2H), 6.47 (s, 1H), 7.07 (s, 1H).

To a solution of 6-iodobenzo[d][1,3]dioxol-5-amine (1 g, 3.8 mmol) and paraformaldehyde (1.14 g, 38 mmol) in methanol (10 mL) was added NaBH$_3$CN (2.39 g, 38 mmol) slowly with stirring. The mixture was heated to 50° C. for 4 h. Water (100 mL) was added and extracted with methylene chloride (100 mL). The organic layer was washed with brine (100 mL), dried (MgSO$_4$) and evaporated under vacuum to give crude title compound 0102-15 (1.16 g) as a brown oil which was used directly to the next step without further purification. LCMS: 292 [M+1]$^+$; $^1$H NMR (DMSO-d$^6$) δ 2.56 (s, 6H), 6.02 (s, 2H), 6.96 (s, 1H), 7.32 (s, 1H).

Step 7b. tert-Butyl 2-(2-chloro-3-nitropyridin-4-ylamino)ethylcarbamate (Compound 0301-15)

A mixture of 2,4-dichloro-3-nitropyridine (0103) (55 g, 0.285 mol), tert-butyl N-(2-aminoethyl)carbamate (59.3 g, 0.37 mol) and Et$_3$N (43.2 g, 0.427 mol) in DMF (450 mL) was heated to 65° C. and stirred for 2.5 h. The DMF was removed under reduced pressure and the residue was poured into brine, extracted with EtOAc, dried and concentrated. The residue was then recrystallized with EtOH-water to provide the title compound 0301-15 (65 g, 72%) as a yellow solid: LCMS: 317 [M+1]$^+$; $^1$H NMR (DMSO-d$^6$) δ 1.36 (s, 9H), 3.10 (q, 2H, J$_1$=8.0 Hz, J$_2$=16 Hz), 3.30 (q, 2H, J$_1$=8.0 Hz, J$_2$=16 Hz), 6.98 (d, 2H, J=8 Hz), 7.38 (t, 1H, J=7.2 Hz), 8.04 (d, 1H, J=8.0 Hz).

Step 7c. tert-Butyl 2-(3-amino-2-chloropyridin-4-ylamino)ethylcarbamate (Compound 0302-15)

A mixture of compound 0301-15 (70 g, 0.221 mol), iron dust (62 g, 1.105 mol) and FeSO$_4$·7H$_2$O (18.5 g, 66 mmol) in saturated NH$_4$Cl aqueous solution (750 mL) and MeOH (1400 mL) was heated to 80° C. for 3 h. The reaction was then filtered and washed with MeOH. The filtrate was concentrated and the residue was dissolved in dichloromethane. The dichloromethane solution was washed with water and concentrated to give the title compound 0302-15 (55 g, 87%) as a red solid. LCMS: 287 [M+1]$^+$; $^1$H NMR (DMSO-d$^6$) δ 1.37 (s, 9H), 3.13 (m, 4H), 4.69 (s, 2H), 5.76 (d, 1H, J=5.2 Hz), 6.45 (d, 1H, J=5.6 Hz), 6.92 (d, 1H, J=5.2 Hz), 7.41 (d, 1H, J=5.2 Hz).

Step 7d. tert-Butyl 2-(4-chloro-2-thioxo-2,3-dihydroimidazo[4,5-c]pyridin-1-yl)ethylcarbamate (Compound 0303-15)

A mixture of compound 0302-15 (55 g, 0.192 mol), KOH (54 g, 0.959 mol), CS$_2$ (73 g, 0.959 mol) in EtOH (500 mL) and H$_2$O (50 mL) was stirred for 12 h at 85° C. Then the mixture was cooled to room temperature and diluted with water. The mixture was adjusted to pH7 with AcOH, filtered to give the title compound 0303-15 (54.5 g, 87%) as a yellow solid: LCMS: 329 [M+1]$^+$; $^1$H NMR (DMSO-d$^6$) δ 1.20 (s, 9H), 3.33 (s, 2H), 4.24 (t, 2H, J=4.8 Hz), 6.89 (t, 1H, J=5.2 Hz), 7.33 (d, 1H, J=5.2 Hz), 8.14 (d, 1H, J=5.2 Hz), 13.59 (s, 1H).

Step 7e. 1-(2-Aminoethyl)-4-chloro-1H-imidazo[4,5-c]pyridine-2(3H)-thione salt (Compound 0304-15)

A mixture of compound 0303-15 (63.8 g, 0.194 mol) and TFA (150 mL, 1.94 mol) in dichloromethane (750 mL) was stirred for 2 h at 25° C. The solvent was removed and dried to give the title compound 0304-15 (163 g) as a yellow solid which was used directly in next step without further purification: LCMS: 229 [M+1]$^+$; $^1$H NMR (DMSO-d$^6$) δ 3.27 (q, 2H, J$_1$=5.2 Hz, J$_2$=11.2 Hz), 4.47 (t, 2H, J=6.0 Hz), 7.55 (d, 1H, J=5.2 Hz), 7.92 (s, 2H), 8.20 (d, 1H, J=5.2 Hz), 12.22 (s, 2H), 13.78 (s, 1H).

Step 7f. 4-Chloro-1-(2-(neopentylamino)ethyl)-1H-imidazo[4,5-c]pyridine-2(3H)-thione (Compound 0305-15)

A suspension of compound 0304-15 (163 g, 0.194 mol) in MeOH (1300 mL) was adjusted to pH 8 with NEt$_3$ (~100 mL) at ice bath. Then pivalaldehyde (33.4 g, 0.388 mol) was added to the mixture and the mixture was stirred for 30 min at room temperature. NaBH$_3$CN (48.76 g, 0.776 mol) was added to the mixture and the mixture was stirred at room temperature overnight. The resulting solid was filtered to give the title compound 0305-15 (38.6 g, total yield of two steps: 67%) as a yellow solid: LCMS: 299 [M+1]$^+$; $^1$H NMR (DMSO-d$^6$) δ 0.79 (s, H), 2.36 (s, 2H) 2.95 (t, 2H, J=6.0 Hz), 4.32 (t, 2H, J=6.0 Hz), 7.49 (d, 1H, J=5.6 Hz), 8.07 (d, 1H, J=5.6 Hz).

Step 7g. 4-Amino-1-(2-(neopentylamino)ethyl)-1H-imidazo[4,5-c]pyridine-2(3H)-thione (Compound 0306-15)

A mixture of compound 0305-15 (11.4 g, 38.2 mmol) and sodium amide (30 g, 769 mmol) in 400 mL liquid ammonia was stirred at 25° C. for 24 h in a autoclave. Ammonia was volatilized before opening the autoclave. Water was added carefully until all solids were dissolved. This solution was adjust pH 7 with acetic acid and filtered to obtain the title compound 0306-15 (9 g, 84%) as a gray solid: LCMS: 280 [M+1]$^+$; $^1$H NMR (DMSO-d$^6$) δ 0.792 (s, 9H), 2.27 (s, 2H), 2.84 (m, 2H), 4.19 (m, 2H), 6.06 (s, 2H), 6.77 (m, 1H), 7.71 (m, 1H).

Step 7h. 2-(6-(Dimethylamino)benzo[d][1,3]dioxol-5-ylthio)-1-(2-(neopentylamino) ethyl)-1H-imidazo[4,5-c]pyridin-4-amine (Compound 15)

A mixture of 0306-15 (100 mg, 0.36 mmol), 0102-15 (200 mg, 0.68 mmol), neocuproine hydrate (14 mg, 0.068 mmol), CuI (12 mg, 0.068 mmol) and NaOt-Bu (66 mg, 0.068 mmol) in anhydrous DMF (6 mL) was stirred for 12 h at 110° C. (oil bath) under nitrogen atmosphere. The solvent was poured into water, the mixture was then extracted with ethyl acetate. Solvents were removed and the crude was purified by prep-TLC (CH$_2$Cl$_2$/MeOH at 20/1) to obtain the title compound 15: LCMS: 443 [M+1]$^+$; $^1$H NMR (DMSO-d$^6$) δ 0.748 (s, 9H), 2.16 (s, 2H), 2.63 (s, 6H), 2.74 (t, 2H, J=6.0 Hz), 4.21 (t, 2H, J=6.0 Hz) 5.94 (s, 2H), 6.16 (s, 1H), 6.38 (s, 2H), 6.84 (d, 1H, J=6.0 Hz), 7.01 (s, 1H), 7.70 (d, 1H, J=5.6 Hz).

Biological Assays:

As stated hereinbefore the derivatives defined in the present invention possess anti-proliferation activity. These properties may be assessed, for example, using one or more of the procedures set out below:

(a) An In Vitro Assay which Determines the Ability of a Test Compound to Inhibit Hsp90 Chaperone Activity.

The Hsp90 chaperone assay was performed to measure the ability of HSP90 protein to refold the heat-denatured luciferase protein. HSP90 was first incubated with different concentrations of test compounds in denaturation buffer (25 mM Tris, pH7.5, 8 mM MgSO$_4$, 0.01% bovine gamma globulin and 10% glycerol) at room temperature for 30 min. Luciferase protein was added to denaturation mix and incubated at 50° C. for 8 min. The final concentration of HSP90 and luciferase in denaturation mixture were 0.375 μM and 0.125 μM respectively. A 5 μl sample of the denatured mix was diluted into 25 μl of renaturation buffer (25 mM Tris, pH7.5, 8 mM MgSO4, 0.01% bovine gamma globulin and 10% glycerol, 0.5 mM ATP, 2 mM DTT, 5 mM KCl, 0.3 μM HSP70 and 0.15 µM HSP40). The renaturation reaction was incubated at room temperature for 150 min, followed by dilution of 10 µl of the renatured sample into 90 µl of luciferin reagent (Luclite, PerkinElmer Life Science). The mixture was incubated at dark for 5 min before reading the luminescence signal on a TopCount plate reader (PerkinElmer Life Science).

(b) HSP90 Competition Binding (Fluorescence Polarization) Assay.

A fluorescein isothiocyanate (FITC) labeled GM was purchase from InvivoGen (ant-fgl-1). The interaction between HSP90 and labeled GM forms the basis for the fluorescence polarization assay. A free and fast-tumbling FITC labeled GM emits random light with respect to the plane of polarization plane of excited light, resulting in a lower polarization degree (mP) value. When GM is bound to HSP90, the complex tumble slower and the emitted light is polarized, resulting in a higher mP value. This competition binding assay was performed in 96-well plate and with each assay contained 10 and 50 nM of labeled GM and purified HSP90 protein (Assay Design, SPP-776F) respectively. The assay buffer contained 20 mM HEPES (pH 7.3), 50 mM KCl, 1 mM DTT, 50 mM $MgCl_2$, 20 mM $Na_2MoO_4$, 0.01% NP40 with 0.1 mg/ml bovine gamma-globulin. Compounds are diluted in DMSO and added to the final assay before labeled GM with concentration range from 20 uM to 2 nM. mP value was determined by BioTek Synergy II with background subtraction after 24 hours of incubation at 4° C.

The following TABLE B lists compounds representative of the invention and their activity in HSP90 assays. In these assays, the following grading was used: I≥10 µM, 10 µM>II>1 µM, 1 µM>III>0.1 µM, and IV≤0.1 µM for $IC_{50}$.

TABLE B

| Compound No. | HSP90 Chaperone ($IC_{50}$) | HSP90 Binding ($IC_{50}$) |
|---|---|---|
| 1 | | III |
| 2 | III | IV |
| 3 | | III |
| 5 | | IV |
| 8 | | III |
| 9 | | III |
| 10 | | III |
| 11 | | III |
| 15 | | IV |

PK in Mouse Blood and Tissues after Oral and Intravenous Administration:

Female athymic nude (CD-1 nu/nu) were obtained from Charles River Laboratories (Wilmington, Mass.). They were housed in ventilated micro-isolator cages in Curis animal facility conditioned at temperature of 23±1° C., humidity of 50-70%, and a 12-hour light/12-hour dark cycle. The animals were fed with irradiated laboratory rodent diet ad libitum and provided with sterilized water. HCT116 human colorectal cancer cells were cultured in RPMI-1640 medium plus 5% FBS (fetal bovine serum) in 5% $CO_2$ incubator. When the cells reached about 70-90% confluent, they were harvested by treatment with trypsin-EDTA (0.25% Trypsin, 1 mM EDTA). The cell pellet was diluted in HBSS (Hank's balanced salt solution) for implantation. For subcutaneous (s.c) tumor implantation, 5 million of cells were injected into the right hind flank region of each mouse. When tumors reached around 200 $mm^3$, mice were dosed orally with a solution containing compounds that need to be evaluated. The concentration for each compound in the solution was kept below 5 mg/ml. The maximum number of compound in one cassette was 6.30% Captisol (Cydex) was used for all formulation. At various time points (3 mice per time point) following compound administration, mice were euthanized with $CO_2$, blood and tissues were collected. Blood was collected into tubes containing sodium heparin. The plasma was separated via centrifugation and stored at −40° C. before analysis. Tissues including tumors were homogenized in 0.8 ml water. An internal standard was added into the tissue homogenates. The homogenates were extracted with 1 ml ethyl acetate for three times. After evaporation, the residual was reconstituted in 0.1 ml acetonitrile for LC/MS/MS assay (Agilent HPLC 1100 Series). FIGS. 1-3 shows the tissue concentration and pharmacokinetic profiles from cassette dose studies of compounds 2 and 15 as determined through additional studies.

TABLE C

HSP90 Compounds in Mouse Brain (ng/g) after i.v. delivery (5 mg/g Cassette Study)

| Time (hr) | 21 | 2 | 20 | 15 |
|---|---|---|---|---|
| 0.08333 | 4076.8 | 4405.4s | 588.4 | 3236.8 |
| 0.5 | 1913.2 | 2510.2 | 327.5 | 1449.8 |
| 2 | 968.4 | 1323.0 | 252.4 | 773.3 |
| 6 | 245.9 | 392.0 | 67.6 | 177 |
| 24 | 39.7 | 47.9 | 6.7 | 27.0 |
| 48 | 6.0 | 0.1 | 2.3 | 4.8 |

TABLE D

HSP90 Compounds in Mouse Brain (ng/g) after oral delivery (10 mg/g Cassette Study)

| Time (hr) | 21 | 2 | 20 | 15 |
|---|---|---|---|---|
| 0.5 | 108.9 | 148.0 | 22.2 | 61.2 |
| 2 | 409.0 | 792.7 | 74.9 | 255.6 |
| 6 | 373.6 | 833.9 | 83.9 | 217.9 |
| 24 | 10.8 | 8.2 | 4.0 | 5.9 |
| 48 | 1.4 | 1.1 | 0.8 | 0.7 |

TABLE E

AUC values of HSP90 compounds in the brain

| Compound No. | 21 | 2 | 20 | 15 |
|---|---|---|---|---|
| AUC i.v. (hr*ng/g) | 8956.3 | 12281.1 | 2041.8 | 6761.3 |
| AUC p.o. (hr*ng/g) | 5587.4 | 11686.8 | 1243.7 | 3293.9 |
| F (%) | 31.2% | 47.6% | 30.5% | 24.4% |

PK profile of compound 15 was measured after oral administration of 30 mg/kg dose in a single dose study. A $T_{1/2}$ of 3.30 hours, a $T_{max}$ of 2.00 hours, a $C_{max}$ of 1378 ng/mL, an $AUC_{0-24}$ of 10414 hr*ng/mL, and an $AUC_{inf}$ of 10480 hr*ng/mL were measured. FIGS. 4-7 show the concentrations and pharmacokinetic profiles of compound 15 in plasma, tumor, brain and lung tissues from separate studies.

A similar procedure as above was performed in nude mice with U87MG Xenografts. The study showed good to excellent results for the crossing of all compounds tested with superior results observed for Compound 15 (Table F). A similar procedure as above with U87MG Xenografts were used to study the pharmacodynamic effects of 40 mg/Kg, 80 mg/Kg and 160 mg/Kg oral dosage (every other day) of Compound-15. (FIGS. 21A and B). FIG. 21B shows results analyzed by Western blot in U87MG s.c. tumors treated with Compound-15 for 3 weeks compared with vehicle control (n=4). After a dosing period of 21 days (40, 80 or 160 mg/kg every other day), mice were sacrificed and 4 tumors from each group were collected for Western blot analysis using antibodies as indicated. Results showed dose-dependent inhibition of multiple HSP90 client proteins, correlating with efficacy results. (FIG. 21B)

TABLE F

| HSP90 Compounds in Mouse Brain (ng/g) after oral (30 mg/Kg) delivery | | | | |
|---|---|---|---|---|
| Time (hr) | 22 | 15 | 20 | 23 |
| 0 | 0 | 0 | 0 | 0 |
| 0.5 | 2.5 | 66.4 | 29.3 | 5.4 |
| 1 | 2.2 | 124.1 | 56.6 | 13.6 |
| 3 | 3.7 | 257.1 | 109.3 | 21.5 |
| 6 | 0.9 | 77.8 | 37.9 | 9.1 |
| 24 | 1.3 | 3.2 | 1.8 | 3.0 |
| AUC (hr*ng/g) | 36.7 | 1692.2 | 782.7 | 231.8 |

Blood Brain Barrier Penetration and clogP Values:

The octanol/water partition coefficient (cLogP) values for several compounds of the invention were calculated using ACD/ChemSketch program available from Advanced Chemistry Development Inc. (Table G). The calculated cLogP values showed a correlation to effective crossing of the blood brain barrier. Based on the results, compounds of formula I with a clogP value of about 3.70 or more are considered effective in crossing the blood brain barrier. Preferred compounds have a cLogP value of at least 4.00 and most preferred compounds have a cLogP value of at least 4.20.

TABLE G

| cLogP values | |
|---|---|
| Compound No. | cLogP |
| 2 | 5.59 |
| 15 | 4.32 |
| 20 | 3.46 |
| 21 | 4.85 |
| 22 | 3.24 |
| 23 | 2.98 |

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

Activity of Compound-15 Against Erlotinib-Resistant NSCLC

H1993 and H1975 NSCLC cells were incubated with 1 µmol/L of Compound-15 for 7 hours and cultured in compound-free medium for an additional 0, 17 or 24 hours and analyzed by Western blot. (Results are shown in FIGS. 15A and B). Compound-15 treatment reduced the levels of phosphorylated-MET as well as total MET, the amplification of which is responsible for erlotinib resistance in NSCLC. In addition, Compound-15 treatment suppressed downstream PI3K/AKT and RAF/ERK signaling as shown by reduced p-AKT/AKT and p-ERK/ERK levels (FIGS. 15A and B).

HSP90/Compound-15 Binding Assay:

The ability of compound 15 to interact with HSP90 derived from erlotinib-resistant NSCLC cells, fluorescence polarization assay was conducted with geldanamycin competition using cell extracts prepared from cultured H1975 and H1993 NSCLC cell lines, which become resistant to erlotinib due to EGFRT790M mutation and c-MET amplification, respectively. Compound 15 strongly bind to cancer derived HSP90 complex with an $IC_{50}$ of 61.2 nmol/L in H1975 and 74.2 nmol/L in H1993, respectively (FIG. 16).

Inhibition of HSP90 Client Proteins by Compound-15:

A pharmacodynamic study in H1975 subcutaneous tumors showed potent inhibition of multiple HSP90 client proteins and induction of apoptosis following a single dose of Compound-15 at 160 mg/kg (FIG. 17). Most importantly, the compound induced degradation of mutant EGFR, the gene conferring oncogenicity and erlotinib resistance in the H1975 cell line. The degradation of EGFR was accompanied by inhibition of its downstream signaling molecules of the cell proliferation (RAF, p-ERK) and survival (p-AKT) pathways, with concurrent induction of HSP70, a marker of HSP90 inhibition. Furthermore, Compound-15 robustly induced apoptosis at both the 6- and 24-hour time points as measured by PARP and caspase-3 cleavages.

Efficacy Study in the H1975 Subcutaneous Tumor Model:

Cells (3.5×106) were implanted subcutaneously into nude mice. Treatment with vehicle control or Compound-15 at 80, 120, or 160 mg/kg (orally, once every 2 days) started when tumors reached an average volume of 118 mm$^3$. Dose-dependent inhibition of tumor growth was observed (FIG. 18A), without significant loss of body weight (FIG. 18B).

Efficacy Study in the H1975 Orthotopic Lung Tumor (NSCLC) Model:

H1975 cells (2×106) were implanted orthotopically to the left lung of nude mice. Starting four days after tumor implantation, mice were treated with Compound-15 (120 mg/kg, orally, once every two days), erlotinib (50 mg/kg, orally, once a day), or vehicle control. Compound-15 treatment for 5 wk significantly prolonged animal survival (P=0.001), whereas erlotinib displayed no therapeutic benefit (P>0.05) (FIG. 19A).

Dose-dependent efficacy study of Compound-15 in H1975 orthotopic lung tumor model (n=11): Mice were treated with Compound-15 (20, 40, 80, and 120 mg/kg) starting 4 day after tumor implantation. Compound-15 dose-dependently extended animal survival following a 5-wk dosing regimen (FIG. 19B).

Pharmacodynamic Study in H1975 Orthotopic Lung Tumors:

Animals bearing H1975 orthotopic lung tumors were treated with Compound-15 at 160 mg/kg once. Tumors were collected at various time points (n=2-3) and subjected to Western blot analysis. Sustained induction of HSP70 and apoptosis and inhibition of oncoprotein phosphorylated-AKT were observed (FIG. 19C).

Efficacy Study in H1975 Intracranial Metastasis Model (n=10):

H1975 cells (5×105) were implanted intracranially into nude mice. Starting 5 days after tumor implantation, mice were treated with Compound-15 (120 mg/kg, orally, once every two days), lapatinib (75 mg/kg, orally, twice a day), or vehicle control. Compound-15 treatment for 4 wk significantly prolonged animal survival (P=0.001) in contrast to the lack of lapatinib efficacy (P>0.05) (FIG. 19D).

Efficacy Study in Rat tMCAO Model:

Male Wistar rats were subjected to 90 min tMCAO followed by administration of single dose of Compound 2 at 4 hrs post-tMCAO onset by IV. Rats were euthanized 48 hrs post-tMCAO and size of infarct was analyzed by TTC staining (FIGS. 11 and 12).

Induction of HSP70 Up-Regulation in Primary Hippocampal Neuron Cultures:

Hippocampal neurons were cultured from E17 rats. Cultures at DIV 5 were treated with Compound 21 for 24 hrs. Compound 21 induced HSP70 level increase (FIG. 13). Effect of Compound 21 on PHF-tau Level in primary hippocampal neuron cultures: High endogenous PHF-tau level is due to the nature of embryonic culture Compound 21 and Aβ oligomer were co-administrated to the culture at DIV 5. Aβ oligomer treatment induces slight increase of PHF-tau level. Compound 21 significantly decreases the PHF-tau level (FIG. 14).

Pharmacodynamic Study in K-Ras-Mutated A549 (Human Lung Adenocarcinoma Epithelial Cell Line) Subcutaneous Tumors:

Compound-15 was dosed at 160 mg/kg, and tumors were collected at the 6- and 24-h time points (n=4) and subjected to Western blot analysis using antibodies as indicated. Potent inhibition of HER2 as well as key components of the PI3K/AKT and RAF/MEK/ERK signaling pathways, along with concurrent induction of HSP70 at both the 6- and 24-h time points, was observed (FIG. 20A).

Efficacy Study was Conducted in A549 Subcutaneous Tumor Model (n=7).

Cells (5×106) were implanted subcutaneously into nude mice. Treatment with vehicle or Compound-15 (160 mg/kg, orally, once every two days) started when tumors reached an average volume of 84 mm$^3$. Tumor stasis was observed in the treatment group (T/C 9.5%, P<0.001). Tumor volumes were expressed as mean±SE. (FIG. 20B) Efficacy study was conducted in A549 orthotopic lung tumor model (n=10). A549 cells (1×106) were implanted orthotopically to the left lung of nude mice. Beginning 4 d after tumor implantation, mice were treated with Compound-15 (120 mg/kg, orally, once every two days), erlotinib (50 mg/kg, orally, once a day), or vehicle control for 4 wk. Compound-15 treatment significantly prolonged animal survival (P=0.001), whereas erlotinib exhibited no antitumor effect (P>0.05) (FIG. 20C). Efficacy study of Compound-15 was conducted in combination with paclitaxel in H1975 subcutaneous tumor model (n=9). H1975 cells (4×106) were implanted subcutaneously into nude mice. When tumors reached an average volume of 150 mm$^3$, animals were treated with either Compound-15 (160 mg/kg, orally, once every two days), paclitaxel (12.5 mg/kg, i.p., twice weekly), or a combination of the two agents. An enhanced antitumor effect was observed in the combination group (P<0.05) (FIG. 20 D).

Efficacy Study of Compound-15 in MV4-11 (Human Lymphoblast Cell Line) S.C. Tumors:

After a single oral dosing of Compound-15 at 160 mg/kg, tumors were collected at 6 and 24 h (n=3), homogenized, and analyzed by Western blot (FIG. 22A). In an efficacy study using MV4-11 s.c. tumor model (n=8), MV4-11 AML tumor cells (20×10$^6$) were implanted s.c. into sever combined immunodeficient mice. Treatment with Compound-15 (160 mg/kg, orally, q2d) started when tumors reached an average volume of 146 mm$^3$. Compound-15 treatment for three weeks, q2d (every other day), showed complete tumor regression (FIG. 22B). Efficacy study was conducted in larger mice with larger sized tumors, with pretreatment volume of 380 and 835 mm$^3$, FIGS. 22C and 22D respectively.

PD Study after Single Oral Dosing of Compound-15 in H1975 (NSCLC) S.C. Tumors:

After a single oral dosing of CUDC-305 at 80 mg/kg, tumors were collected at 8 h (n=3), homogenized, and analyzed by Western blot using antibodies as indicated. EGFR and multiple signaling molecules were inhibited (FIG. 23A).

Efficacy Study in the H1975 S.C. Tumor Model (n=9):

H1975 NSCLC cells (5×10$^6$) were implanted s.c. into nude mice. Treatment with Compound-15 (160 mg/kg, orally, q2d) started when tumors reached an average volume of 160 mm$^3$. Dosing of Compound-15 for 3 wk significantly inhibited tumor growth compared with vehicle control (T/C, 15.4%; P<0.001) (FIG. 23B).

Efficacy Study in the MDA-MB-468 Orthotopic Tumor Model (n=8):

MDA-MB-468 breast cancer cells (20×10$^6$) were implanted orthotopically into nude mice. Treatment started when tumor size reached an average volume of 113 mm$^3$. Compound-15 was dosed at 120 mg/kg orally q2d; paclitaxel was dosed at 12.5 mg/kg i.p. twice weekly. Compound-15 delivered as a single agent induced tumor regression by 3.4% (P<0.001). An enhanced antitumor effect was observed when Compound-15 was combined with paclitaxel (tumor regression of 36.6%, P<0.001) (FIG. 23C).

Efficacy Study in the Colo205 S.C. Tumor Model (n=10):

Colo205 colorectal cancer cells (5×10$^6$) were implanted s.c. into nude mice. Treatment with Compound-15 started when tumors reached an average volume of 120 mm$^3$. Compound-15 was dosed at 120 mg/kg orally q2d. Camptothecin-11 was dosed at 15 mg/kg i.p. twice weekly. Compound-15 delivered as single agent significantly inhibited tumor growth (T/C, 14.2%; P<0.001). However, an enhanced antitumor activity was observed in the group treated with Compound-15 and Camptothecin-11 combination (P<0.05) (FIG. 23D). Brain penetration activity of Compounds 2 and 21 was compared to reference compounds VER-052296, Cmp42, SNX-2112 that are known for HSP90 inhibitory activity (FIGS. 9 and 10).

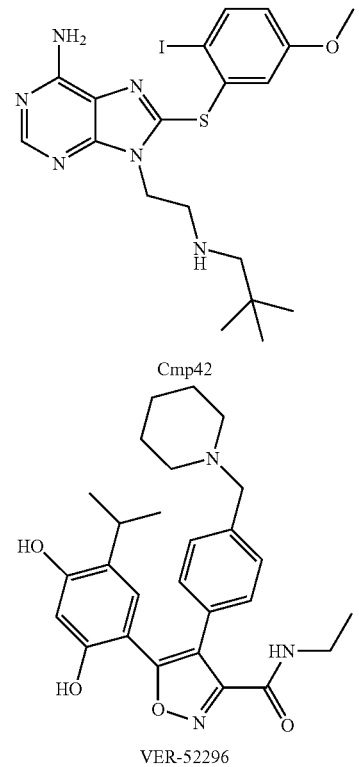

Cmp42

VER-52296

-continued

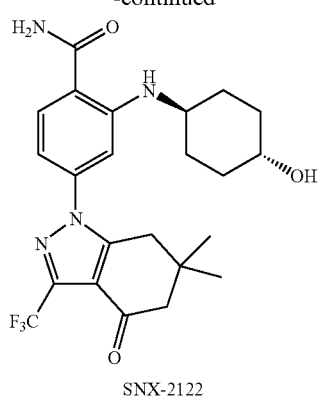

SNX-2122

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of treating a brain related disorder selected from glioblastoma multiforme and brain tumor, by the oral administration of a compound selected from:

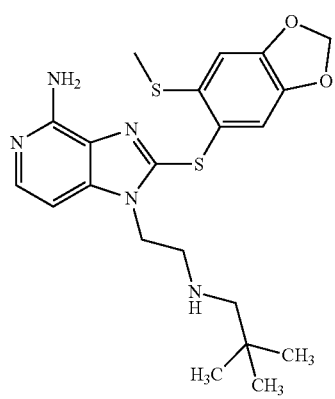

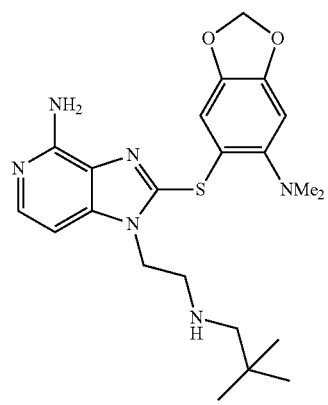 [SMILES: CN(C)c1cc2c(cc1Sc1nc3c(N)nccc3n1CCNCC(C)(C)C)OCO2]

-continued

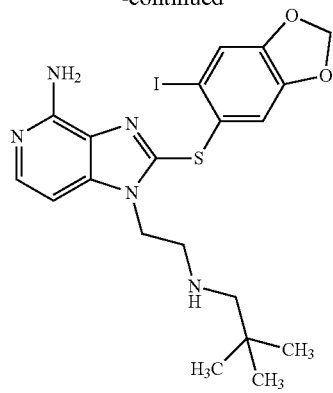

or a pharmaceutically acceptable salt thereof.

2. The method according to claim 1, wherein said compound is:

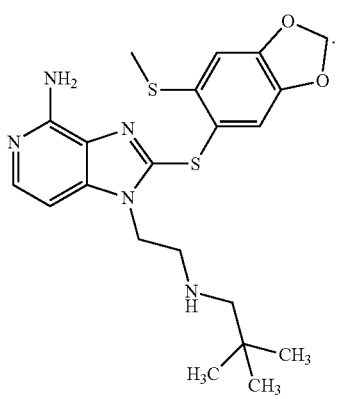 [SMILES: CSc1cc2c(cc1Sc1nc3c(N)nccc3n1CCNCC(C)(C)C)OCO2]

or a pharmaceutically acceptable salt thereof.

3. The method according to claim 1, wherein said compound is:

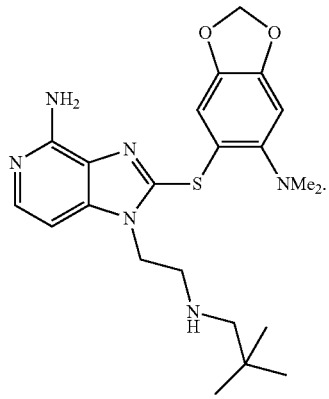 [SMILES: CN(C)c1cc2c(cc1Sc1nc3c(N)nccc3n1CCNCC(C)(C)C)OCO2]

or a pharmaceutically acceptable salt thereof.

4. The method according to claim 1, wherein said compound is:
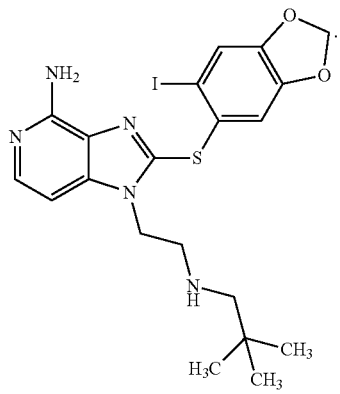 [SMILES: CC(C)(C)CNCCn1c(Sc2cc3c(cc2I)OCO3)nc2c(N)nccc21]
or a pharmaceutically acceptable salt thereof.
5. A method of treating a brain related disorder selected from metastases and secondary brain tumor, by the oral administration of a compound selected from:
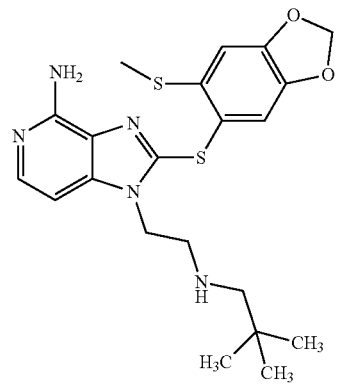
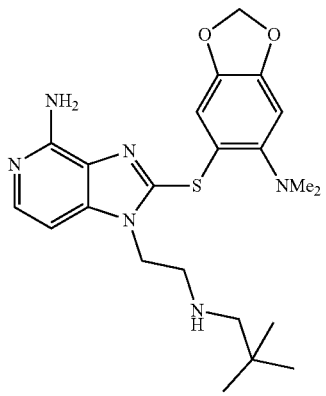
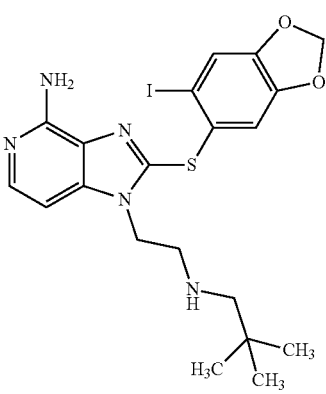
or a pharmaceutically acceptable salt thereof.
* * * * *

UNITED STATES PATENT AND TRADEMARK OFFICE
CERTIFICATE OF CORRECTION

Page 1 of 1

PATENT NO. : 8,722,703 B2
APPLICATION NO. : 12/688312
DATED : May 13, 2014
INVENTOR(S) : Cai et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 689 days.

Signed and Sealed this
Eleventh Day of November, 2014

Michelle K. Lee
*Deputy Director of the United States Patent and Trademark Office*